United States Patent [19]

Seki

[11] Patent Number: 5,734,692
[45] Date of Patent: Mar. 31, 1998

[54] RADIOTHERAPY SYSTEM

[75] Inventor: Yasuhiro Seki, Otawara, Japan

[73] Assignee: Kabushiki Kaisha Toshiba, Kanagawa-Ken, Japan

[21] Appl. No.: 655,852

[22] Filed: May 31, 1996

Related U.S. Application Data

[62] Division of Ser. No. 411,198, Mar. 27, 1995, Pat. No. 5,651,043.

[30] Foreign Application Priority Data

| Mar. 25, 1994 | [JP] | Japan | 6-056373 |
| Mar. 25, 1994 | [JP] | Japan | 6-056374 |
| Mar. 25, 1994 | [JP] | Japan | 6-056388 |

[51] Int. Cl.$^6$ .............................................. A61N 5/01
[52] U.S. Cl. ............................. 378/65; 364/413.26
[58] Field of Search ......................... 364/413.26; 378/65, 378/68, 69

[56] References Cited

U.S. PATENT DOCUMENTS

| 3,720,817 | 3/1973 | Dinwiddle | 364/413.26 |
| 5,329,567 | 7/1994 | Ikebe | 378/20 |
| 5,418,827 | 5/1995 | Deasy et al. | 378/65 |
| 5,528,650 | 6/1996 | Swerdloff et al. | 378/65 |

FOREIGN PATENT DOCUMENTS

| 3-26278 | 2/1991 | Japan |
| 3-224547 | 10/1991 | Japan |

*Primary Examiner*—David P. Porta
*Assistant Examiner*—David Vernon Bruce
*Attorney, Agent, or Firm*—Finnegan, Henderson, Farabow, Garrett & Dunner, L.L.P.

[57] ABSTRACT

There is provided a radiotherapy system comprising: radiotherapy planning CT system integratedly having an X-ray scanner member for acquiring image data of a diagnostic portion of a subject by irradiating X-rays to the subject, said diagnostic portion including a lesion, a radiotherapy planner member for displaying the image data and producing radiotherapy plan data including a position data of an isocenter and a contour data of a radiation field limiting radiations from a virtual radiation source irradiated into the diagnostic portion, and a positioning member for automatically pointing a marking position on the subject based on the position data of the isocenter; and a radiotherapy apparatus for carrying out radiotherapy on the basis of the therapy plan data.

3 Claims, 63 Drawing Sheets

(TOP VIEW)

(SIDE VIEW)

|  | SINGLE-PORT | OPPOSED DUAL-PORT |
|---|---|---|
| FRONTAL (TOP) VIEW | 0° OR 180° | 0° AND 180° |
| LATERAL (SIDE) VIEW | 90° OR 270° | 90° AND 270° |

FIG. 12

{ DEFINING RADIATION FIELD USING A POLYGON ROI }

{ DEFINING A LARGE RADIATION FIELD USING A RECTANGULAR ROI AND ARRANGING SHIELDING BLOCKS USING RECTANGLAR ROIS }

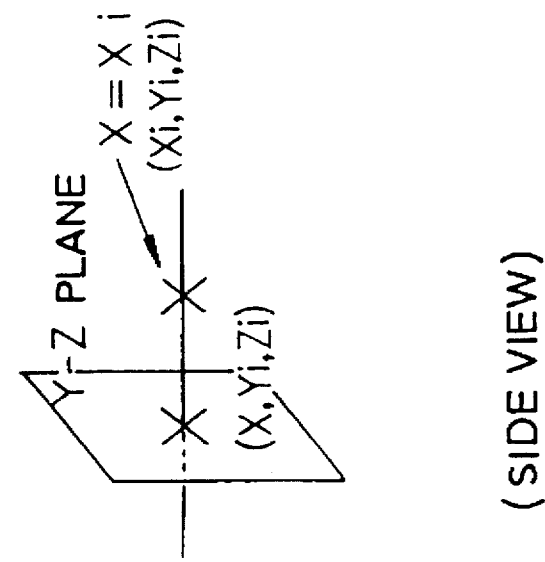
FIG. 15B (SIDE VIEW)
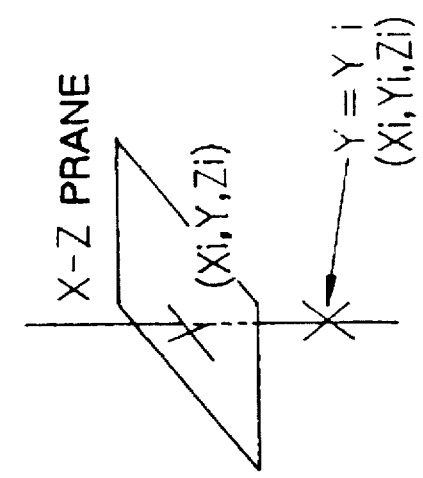
FIG. 15A (TOP VIEW)
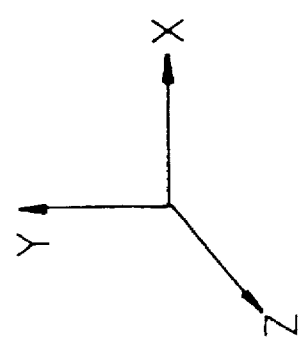

(OPPOSED DUAL-PORT)
IRRADIATION

- α : IRRADIATION START ANGLE
- β : STEP ANGLE
- γ : IRRADIATION END ANGLE
- ⊙ : IRRADIATION POINT

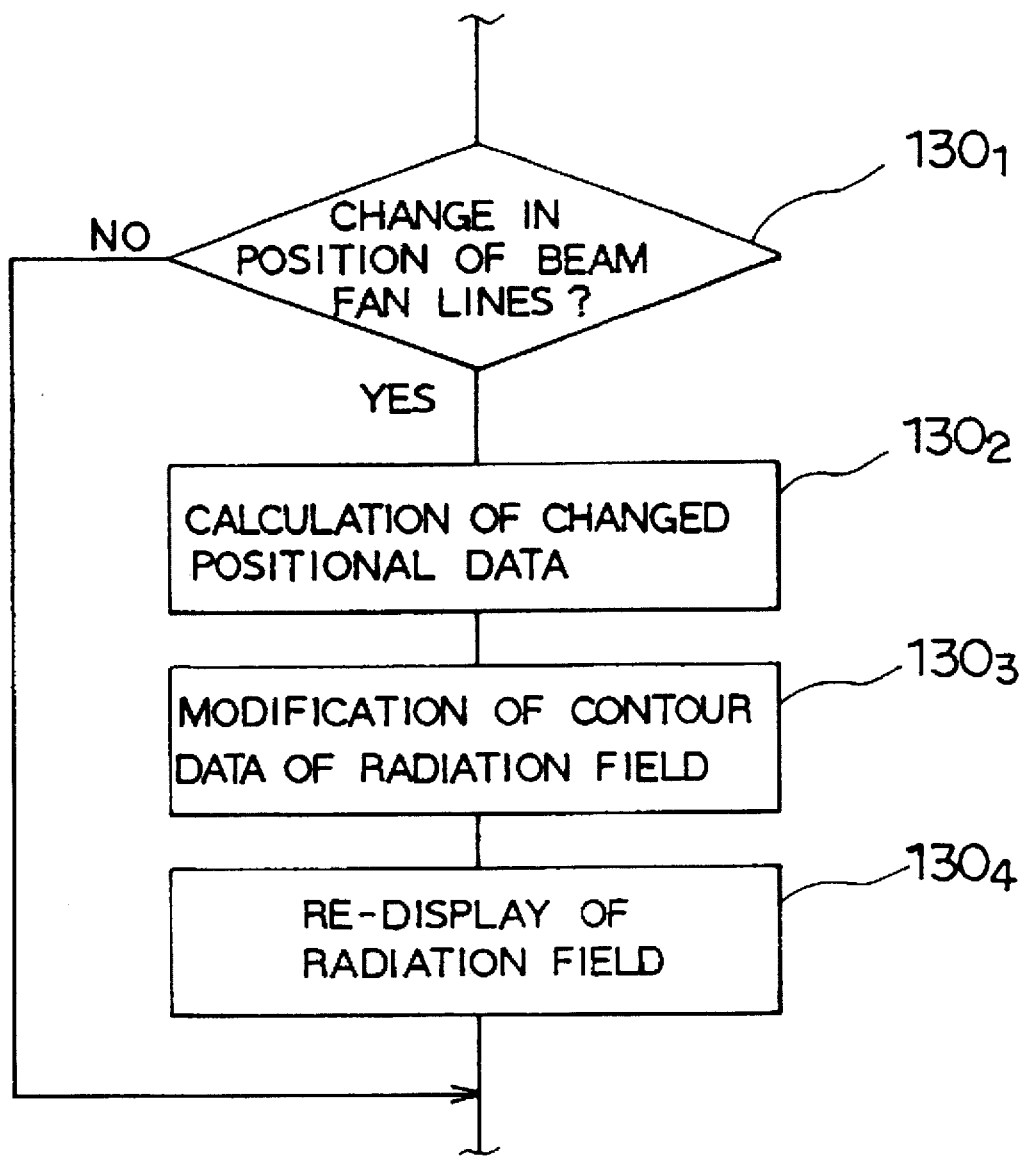
F I G. 34

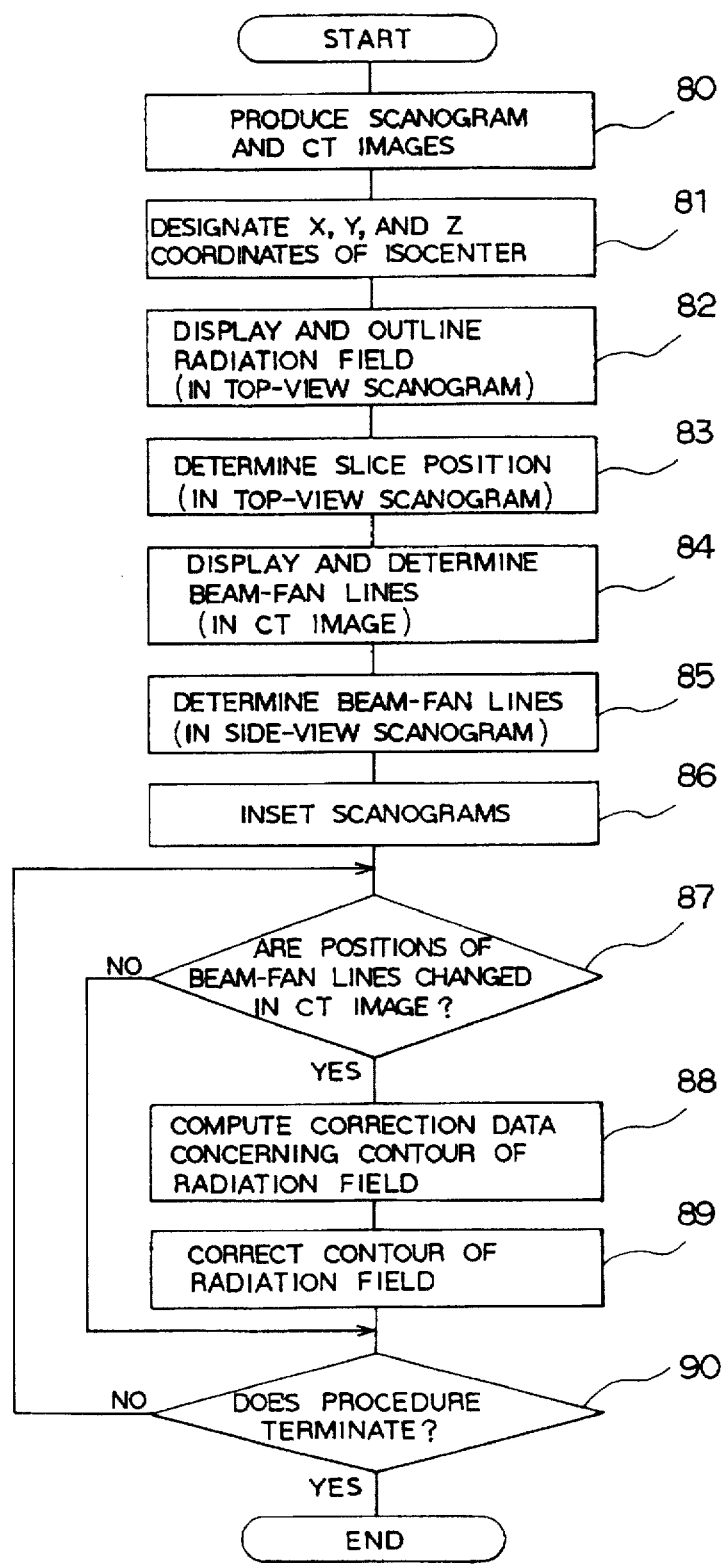
F I G. 46

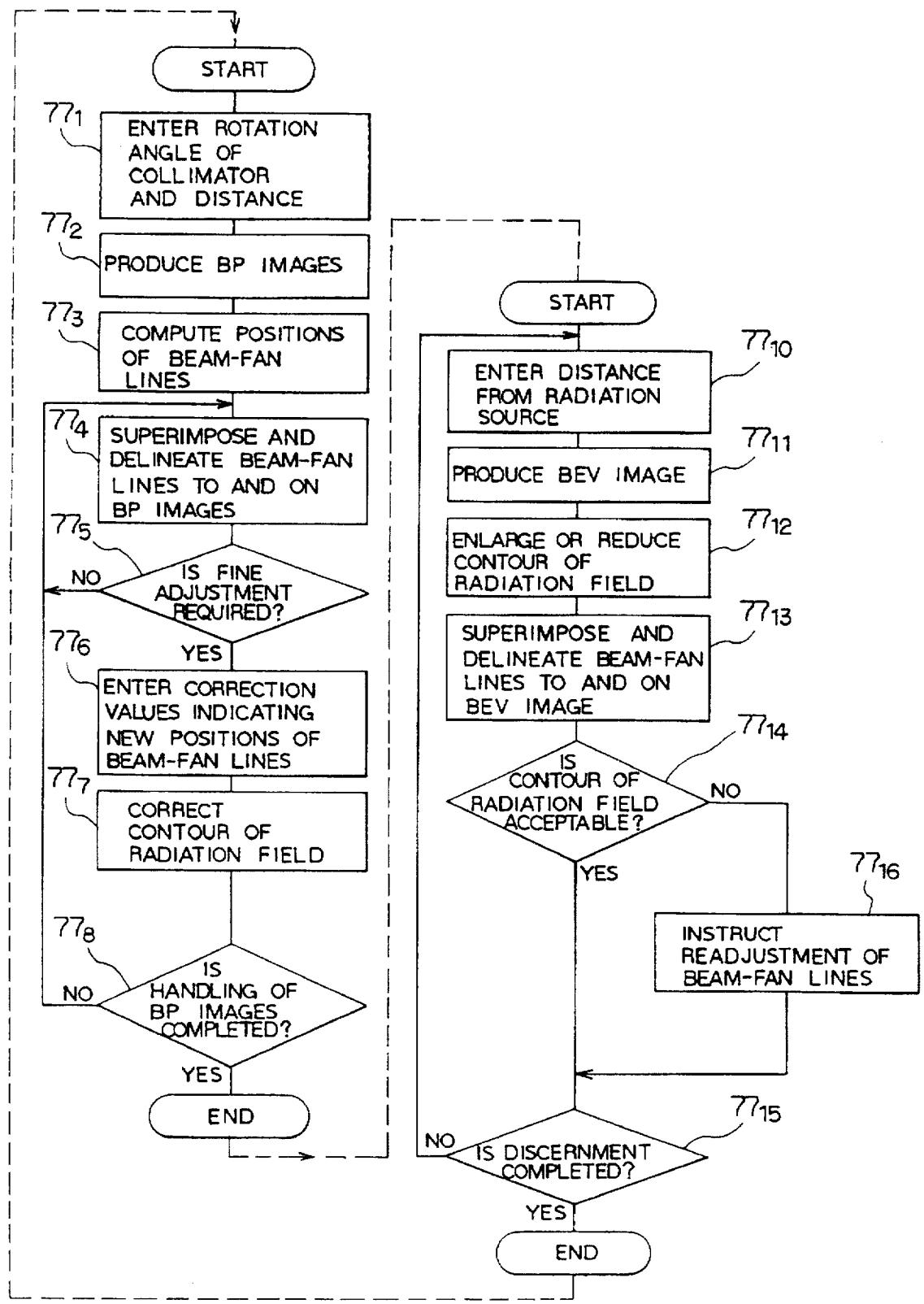
F I G. 55

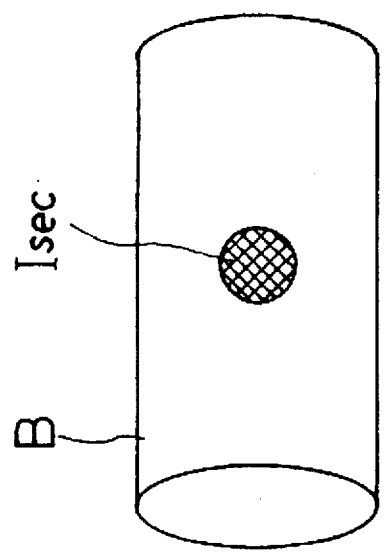
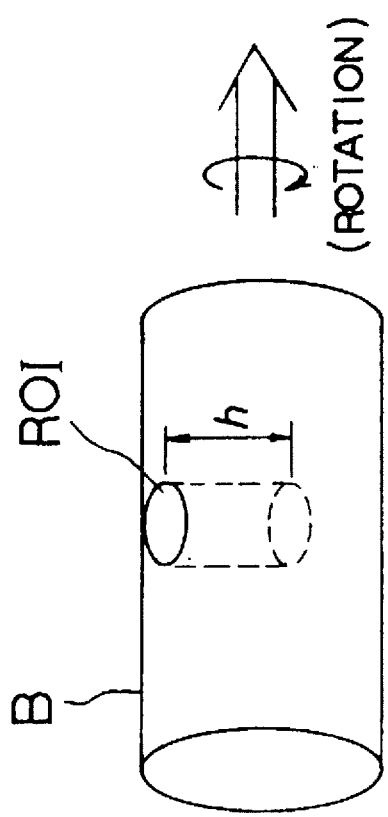
FIG. 60B
FIG. 60A

FIG. 63A
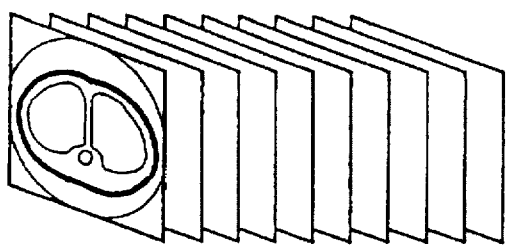
A PLURALITY OF CONSECUTIVE SLICE IMAGES
FIG. 63B
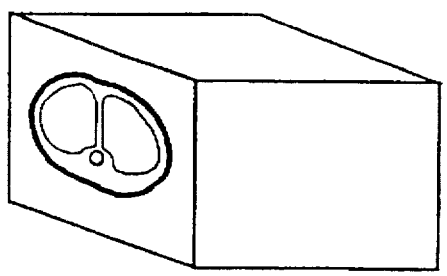
VOXEL IMAGE DATA
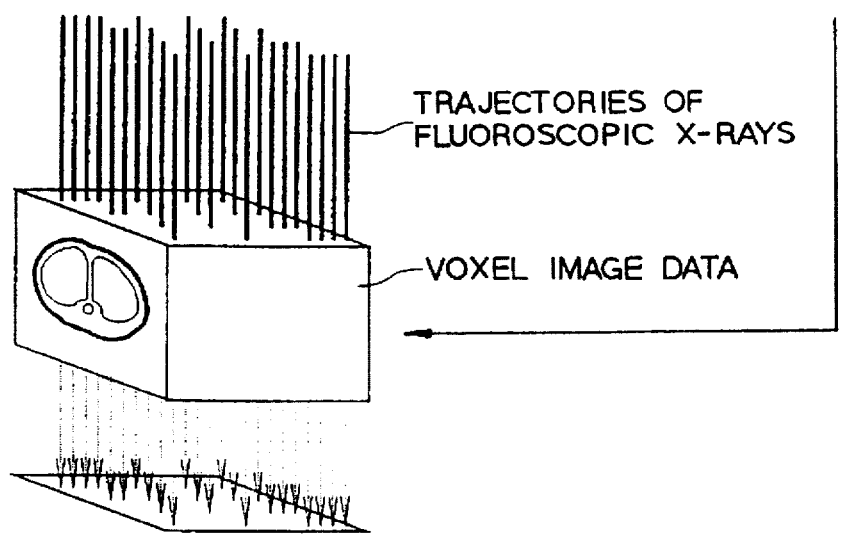
TRAJECTORIES OF FLUOROSCOPIC X-RAYS
VOXEL IMAGE DATA
FIG. 63C
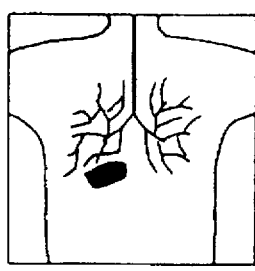
MIP IMAGE (MAXIMUM-VALUE PROJECTION IMAGE)
FIG. 63D

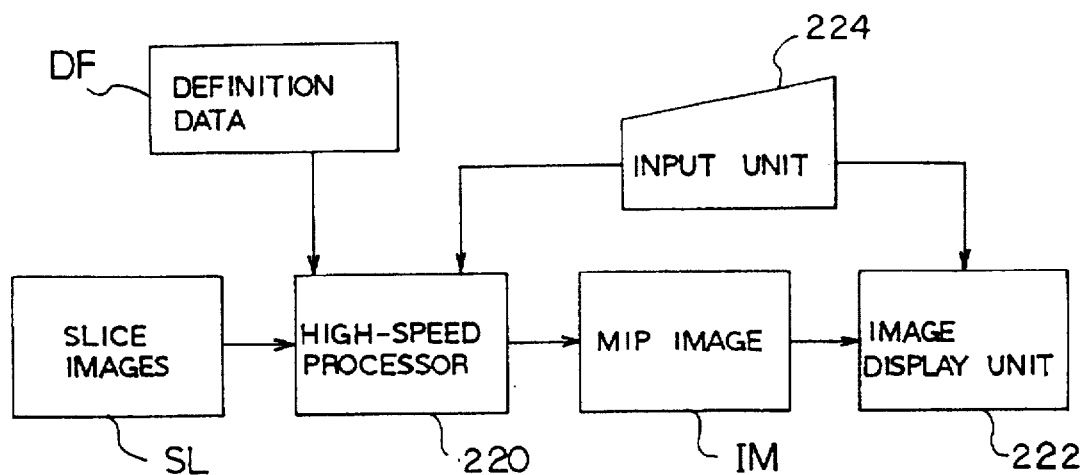
F I G. 67
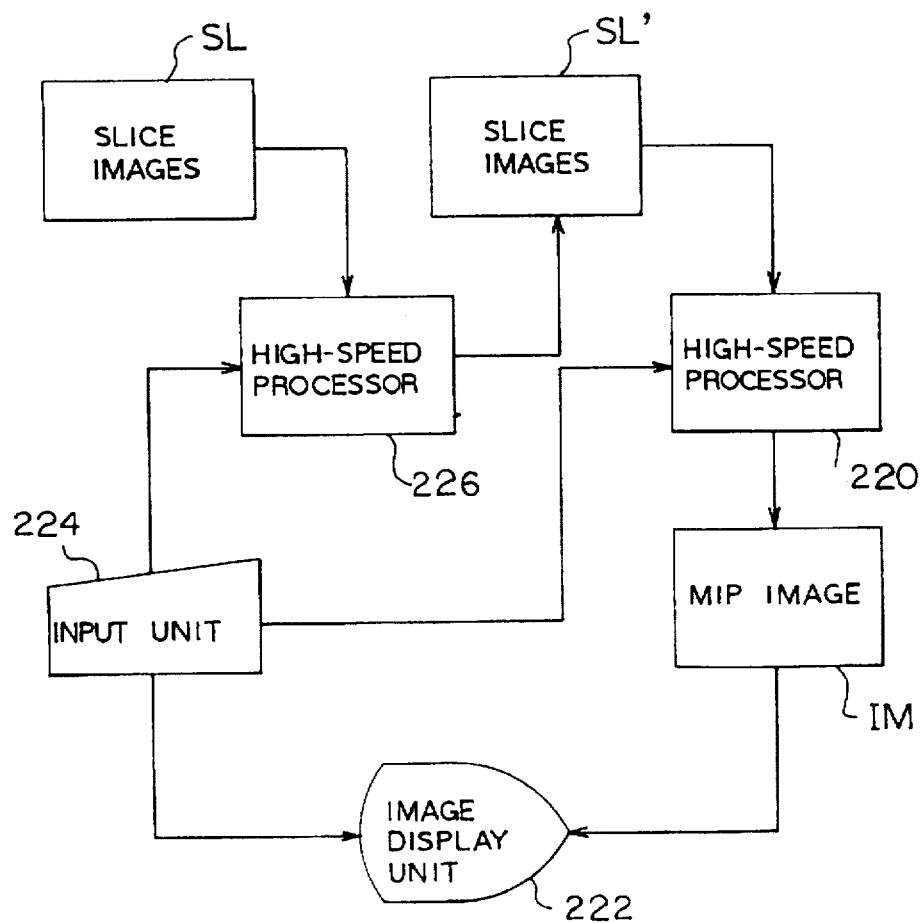
F I G. 68

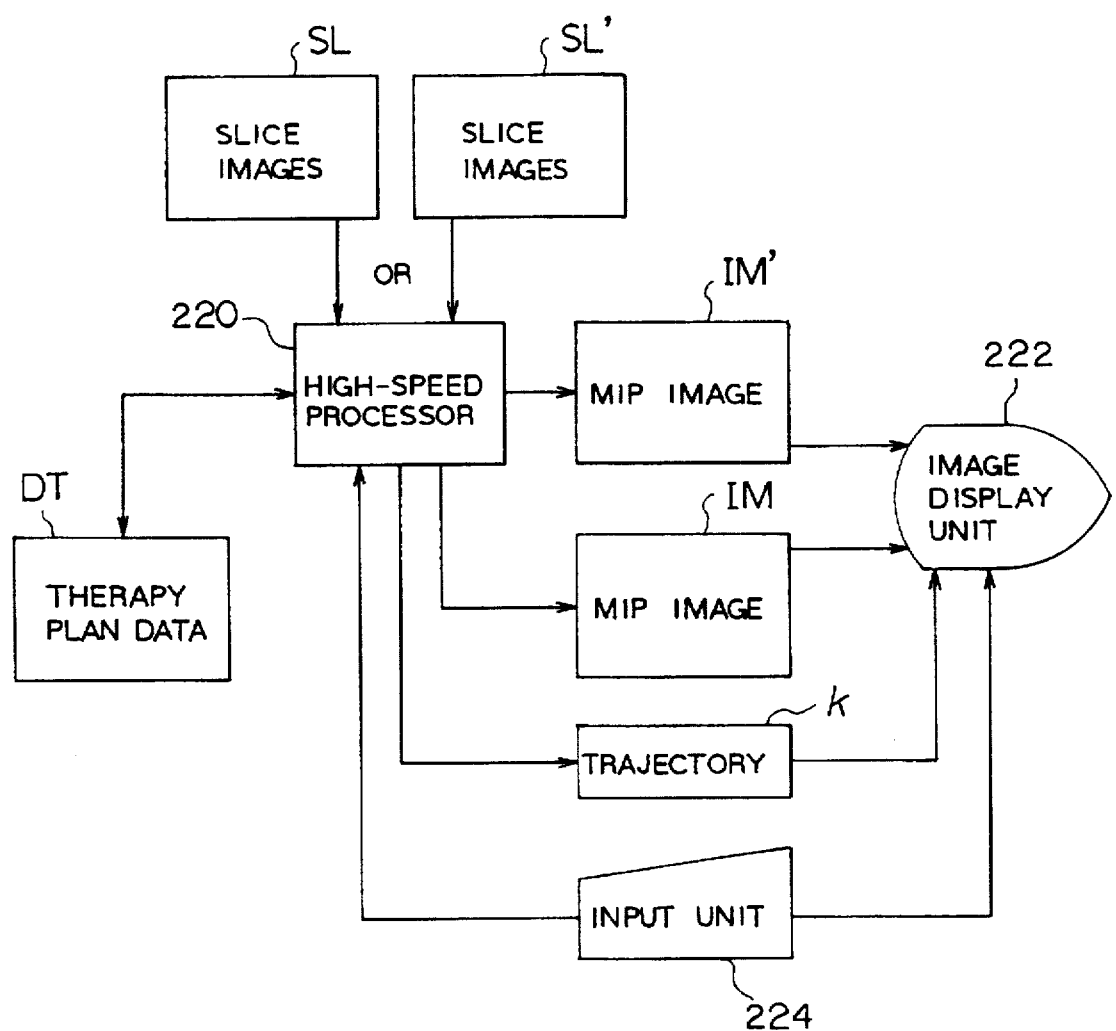
F I G. 69

RADIOTHERAPY SYSTEM

This is a division of application Ser. No. 08/411,198, filed Mar. 27, 1995, now U.S. Pat. No. 5,651,043.

BACKGROUND OF THE INVENTION

1. Field of the Invention

The present invention relates to a radiotherapy system. More particularly, this invention is concerned with a radiotherapy system that includes a radiotherapy planning CT system having an X-ray CT scanner and capable of achieving a whole procedure ranging from imaging of a subject to radiotherapy planning based on the images, and a radiotherapy apparatus for irradiating a subject to accomplish radiotherapy, and that is effective for treatment of carcinoma or the like. The present invention is also concerned with a radiotherapy planner for determining radiotherapy planning data, which comprises part of a radiotherapy system.

2. Description of the Related Art

In the past, radiotherapy in which a lesion such as a carcinoma is irradiated has been put to clinical use. The usefulness has been highly appreciated.

A linear accelerator is generally used as a radiotherapy apparatus for accomplishing radiotherapy. The linear accelerator generates radiation (X-rays) by shooting an accelerated electron beam at a target and the radiation a lesion of a patient lying down on a patient couch.

For treatments using the radiotherapy apparatus, various preparations must be made in advance. In the first stage, an X-ray CT scanner or the like is used to acquire images of a lesion. In the second stage, the images are used to accurately measure the location, size and contour of each lesion and the number of lesions. It is then determined what are the position of an isocenter, a dose distribution, and irradiation parameters (radiation field, angle, number of ports) enabling accurate irradiation of a lesion alone. In the third stage, an X-ray simulator is used to finalize an isocenter, position a patient through fluoroscopy, and draw markers on a body surface (isocenter markers or radiation field markers) on the basis of the determined position of an isocenter, dose distribution and irradiation parameters, and then the simulator performs simulation using the determined irradiation parameters.

When simulation is completed, after a certain period of time has elapsed, treatment is commenced using the radiotherapy apparatus. Prior to the treatment, verification-oriented fluoroscopic images are used to verify the radiation field. The isocenter markers of all the markers drawn on the patient's body surface are used to position the patient, and then the radiation field markers are used to define the opening of a collimator. Thereafter, radiotherapy is actually carried out using the determined irradiation parameters.

In recent years, various approaches have been made to the treatment of carcinoma. The significance of radiotherapy has been reassessed as a means for radical or palliative treatment. There is an increasing demand for more accurate locating of a lesion, more elaborate therapy planning, and more precise therapy.

Under these circumstances, a conventionally-known radiotherapy system comprises an X-ray CT scanner for producing tomographic images or scanograms, a radiotherapy planner used by an operator for making a therapy plan suitable for a lesion on the basis of the images, an X-ray simulator for use in positioning a patient on the assumption of actual treatment according to the plan data, and a radiotherapy apparatus for actually undertaking treatment. In integrated systems, the X-ray CT scanner and X-ray simulator of the four apparatuses share the same patient couch. Proposals for a radiotherapy planning procedure or a positioning procedure have been made in, for example, Japanese Patent Laid-Open No.3-26278 (entitled "A method of controlling a positioning apparatus for radiotherapy planning") and Japanese Patent Laid-Open No.3-224547 (entitled "A method of setting irradiation parameters for a CT scanner").

In the positioning apparatus described in the Japanese Patent Laid-Open No.3-26278, three pointers (mounted in arm modules) for projecting light beams as an isocenter mark on the body surface of a subject are disposed at the upper part (ceiling), and right- and left-hand walls of an examination room. The arm modules are individually actuated using a driver. A misalignment between projected light beams emanating from the pointers on the right- and left-hand walls due to the mechanical strains of the pointers is compensated for in order to match the positions of the cross marks provided by the right and left pointers.

In the method of setting irradiation parameters described in the Japanese Patent Laid-Open No.3-224547, a tomographic image rendering a target region of irradiation of a patient concerned, a multiplane reconstruction (MPR) image formed from the tomographic image with respect to a cross section containing a body axis parallel to an irradiation direction, and an MPR image rendering a cross section with respect to a body axis perpendicular to the irradiation direction are displayed in a screen of a display unit, so that irradiation parameters can be determined with the help of the displayed images showing the relationships between the target region and adjacent tissues.

As seen from the aforesaid prior art, when pointers for projecting crosslight marks are disposed on the walls and ceiling of a room, it is conceivable that the reference position of the positioning apparatus for projecting marks relative to a building may be displaced due to influences such as disturbances including indoor and outdoor vibrations, which are negligible but propagated to the building in the long run, and earthquakes. When such a displacement has occurred, the accuracy of marking an isocenter deteriorates. Every time the site of installing the positioning apparatus is changed, the positions of the pointers must be altered. Moreover, it is required to align the positioning apparatus and pointers. Uncountable labor and time must be consumed for maintenance.

As for the aforesaid procedure of setting irradiation parameters while displaying a tomographic image and two kinds of MPR images at the same time, the MPR images render parallel and vertical planes passing through a target region that is a lesion. For defining a radiation field suitable for the three-dimensional lesion, since the tomographic image does not necessarily provide a projection image rendering the target region with the longest contour, the position of a vertical plane cannot always be specified accurately. The MPR images or especially MPR image rendering the vertical plane must therefore be displayed and observed on a trial-and-error basis. This is a nuisance. It takes too much time for planning. However, when the operational procedure is simplified, the accuracy in setting irradiation parameters may deteriorate.

Aside from the aforesaid method of setting irradiation parameters using a tomographic image and MPR images, a method using axial (tomographic) images and a scanogram (fluoroscopic image) is also well known. However, this method has a drawback in that since the images do not render a plane opposed to a certain irradiation angle of radiation, the opening of a collimator cannot be defined accurately for each irradiation direction during rotation irradiation. Because of this drawback and others, the method cannot keep up with the recent trend toward higher-precision therapy planning.

In any of the aforesaid methods of setting irradiation parameters, when a radiation field is defined and the beam fan lines of a radiation path is checked in an axial image, even if the positions of the beam fan lines are altered, the contour or size of the radiation field does not change. When the positions of the beam fan lines are found inappropriate, another radiation field must be specified by restarting the procedure from the beginning.

Further, a scanogram (a transmission image reconstructed from an X-ray image or a CT image) of a subject and reconstructed axial images (CT images) are usually used for therapy planning. That is to say, the scanogram or something equivalent is used to define a radiation field covering a lesion (target volume), and the axial images are used to identify beam-fan lines. The axial images are also used for plotting energy distribution on a slice.

The foregoing prior art has difficulty in coping with an ongoing demand for higher-precision therapy planning because of the drawbacks described below.

For example, when axial images are used to delineate beam-fan lines, as shown in FIG. 1, although a radiation path vertically transverses an axial plane (that is, an axial image) lying immediately below a radiation source, another radiation path T pierces an axial plane (axial image) $PL_{AX}$ lying away from an isocenter along a body axis. Thus, depending on the location of an axial plane, beam-fan lines (border lines of a radiation path) may not be delineated. Even if the beam-fan lines are delineated, the trajectory of the delineated beam fan is often hard to understand.

In conventional therapy planning, even if beam-fan lines can be identified in an axial image, a transmission image (scanogram or X-ray image) must be used to correct the contour of a radiation field. The beam-fan lines cannot be delineated in any image other than an image rendering a plane (axial plane) perpendicular to a longitudinal axis. Screens must therefore be changed depending on types of images. This is quite inconvenient, deteriorating operational efficiency.

For defining a radiation field, a scanogram or an X-ray image is used. In this case, only a radiation field in a direction of acquiring image data can be defined. For determining an irradiation direction, axial images are used. However, when some organs must not be exposed to radiation, a radiation field must be defined for each axial image.

Furthermore, according to a conventional therapy planning procedure based on a scanogram and axial images, since (axial) images produced during previous scanning are used for therapy planning, a CT image rendering an appropriate portion of a lesion at which an isocenter should be see may not be included in the images produced during previous scanning. In this case, re-scanning is a must. It therefore takes too much time for therapy planning. In addition, a load to an operator or a patient increases.

Even if the CT image rendering an appropriate portion of a lesion is included in the images produced during previous scanning, the reconstruction center of the image is not always consistent with a position at which an isocenter should be set. Moreover, slice thickness seldom agrees with the width of each leaf of a multileaf collimator. Thus, high-quality images rendering planes aligned with radiation paths and assisting in therapy planning can hardly be provided.

SUMMARY OF THE INVENTION

The present invention attempts to solve the aforesaid problems underlying in the prior art. An object of the present invention is to provide a radiotherapy system enabling a reduction in the number of apparatuses constituting a radiotherapy system, realizing a simple and compact hardware configuration for the system, and contributing to higher-precision therapy planning and shorter planning time.

Another object of the present invention is to provide a radiotherapy system capable of feeding contour data concerning a radiation field, which is produced during therapy planning, directly to a radiotherapy apparatus, automatically controlling the opening of a collimator in the radiotherapy apparatus, thus permitting efficient therapy planning and shorter planning time.

Still another object of the present invention is to provide a radiotherapy planning CT system including a light projection facility capable of optimizing the positions of positioning projectors for projecting an isocenter point determined during therapy planning on a body surface, and stabilizing and improving marking accuracy.

Still another object of the present invention is to shorten time required for therapy planning by automating a therapy planning procedure ranging from determination of an isocenter to light projection for marking.

Still another object of the present invention is to provide a radiotherapy planning CT system enabling high-precision therapy planning including defining of an optimal radiation field according to an irradiation angle, realizing easy correction of a therapy plan on a monitor screen, and facilitating simplicity and efficiency of planning work.

Further, another object of the present invention is to delineate easy-to-see beam-fan lines and thus enable higher-precision therapy planning.

Still another object of the present invention is to enable efficient viewing of images through the same screen, permit easy and effortless correction of the contour of a radiation field, and thus realize quick therapy planning with higher precision.

Still another object of the present invention is to enable preferable execution of drilling for synthesizing any cross-sectional image with a frontal-view image in the course of therapy planning, and realize quick therapy planning with higher precision.

Still another object of the present invention is to realize therapy planning in which a radiation field can be defined in any direction, an irradiation direction can be determined easily, and higher precision and excellent operational efficiency are ensured.

Another object of the present invention is to enable higher-precision therapy planning on the basis of images produced by putting great emphasis on a position at which an isocenter should be set.

A further object of the present invention is to enable higher-precision therapy planning on the basis of images produced by putting emphasis on a position at which an isocenter should be set and a thickness of each leaf of a multileaf collimator.

According to one aspect of the present invention, there is provided a radiotherapy system comprising: a radiotherapy planning CT system integratedly having an X-ray scanner means for acquiring image data of a diagnostic portion of a subject by irradiating the subject with X rays, said diagnostic portion including a lesion, a radiotherapy planner means for displaying the image data and producing radiotherapy plan data including a position data of an isocenter and a contour data of a radiation field limiting radiations from a virtual radiation source irradiated into the diagnostic portion, and a positioning means for automatically pointing a marking position on the subject based on the position data of the isocenter; and a radiotherapy apparatus for carrying out radiotherapy on the basis of the therapy plan data.

Preferably, the X-ray scanner means and positioning means have a common-use couch on which the subject lies. Preferably, the X-ray scanner means has a gantry) having a diagnostic opening into which the couch is inserted and said positioning means comprises a light projector for pointing the marking position, said gantry having said light projector. It is preferred that the radiotherapy apparatus has a multileaf-type collimator having a pair of leaf groups each consisting of a plurality of leaves, said pair of leaf groups being oppositely disposed in a path of the radiations and each leaf of said leaf groups being movable toward and away from the radiations independently from each other.

According to another aspect of the present invention, there is provided a radiotherapy planning CT system for planning radiotherapy planning of a lesion of a subject using an X-ray image, the system comprising: an X-ray CT scanner body having a gantry, in which an X-ray tube and an X-ray detector are disposed and a diagnostic opening having an axial direction is formed therethrough, for irradiating the subject inserted into the diagnostic opening with X rays emanating from the X ray tube, and a couch having a tabletop on which the subject lies, said tabletop being inserted into the diagnostic opening, wherein the gantry has three projectors each having movable light-projecting end each projecting a light mark at a point on the subject, said three light projectors being individually disposed at side portions and an upper portion of the diagnostic opening, said three portions existing in a same plane perpendicular to the axial direction, and three moving units arranged correspondingly to the three light projectors, two of said moving units independently moving the light-projecting end of the projector disposed at each of the side portions along in a vertical direction perpendicular to the axial direction and the remaining moving unit moving the light-projecting end of the projector disposed at the upper portion along a lateral direction perpendicular to the axial direction; means for three-dimensionally pointing a position of an isocenter of the lesion on the X-ray image; and means for automatically controlling the light-projecting ends of the three projectors and the tabletop in order to make positions of the three light marks coincide with the positions of the isocenter.

There is also provided a radiotherapy system comprising: a radiotherapy planning CT system for producing data including a contour data of a radiation field required for radiotherapy of a lesion of a subject using an image formed by irradiating the subject with X rays; a radiotherapy apparatus incorporating a radiation source producing radiation and a multileaf-type collimator for limiting a path of the radiation in conformity with the radiation field, said collimator having a plurality of leaves independently movable from each other and forming an opening corresponding to the radiation field; means for producing data of the opening; and means for controlling limiting positions of the plurality of leaves in accordance with the data of the opening, wherein said opening data producing means includes an element for selecting any of a circumscription mode, a inscription mode, and a middle-point mode, said circumscription mode being a state in which limiting ends of the plurality of leaves circumscribe a border of the radiation field, said inscription mode being a state in which the limiting ends inscribe the border, and said middle-point mode being a state in which each middle-point of the limiting ends intersects the border, and an element for calculating the data of the opening in compliance with the selected mode.

There is also provided a radiotherapy planning CT system for producing radiotherapy planning data required for radiotherapy of a lesion of a subject using an image formed based on X rays transmitted through the subject, the system comprising: first planning means for producing the radiotherapy planning data using a scanogram and an axial image of the subject obtained from the transmitted X rays; second planning means for producing the radiotherapy planning data using images of the subject obtained from the transmitted X rays, said images consisting of not only a plurality of axial images and either one of at least one scanogram and an alternative image of the scanogram but also images obtained by processing the plurality of axial images; and means for selectively designating either one of the first and second planning means.

There is further provided a radiotherapy planning CT system, wherein said second planning means includes means for defining an isocenter of a target volume enclosing the lesion on the basis of both at least one of the plurality of axial images and either one of the scanogram and the alternative image, means for producing a transmission image of the target volume of the subject using the plurality of axial images, said the transmission image being viewed through from a virtual radiation source virtually positioned, means for defining a contour of a radiation field on the subject on the basis of a contour of the target volume using the transmission image, means producing a target image whose plane is parallel with a cross section including the isocenter, is perpendicular to an axis from the virtual radiation source, and is defined according to a distance from the virtual radiation source using the plurality of axial images, means for confirming the radiation field using the target image, and means for confirming beam fan lines of radiations emanating from the virtual radiation source through the radiation field using the plurality of axial images.

According to another aspect, a radiotherapy planning CT system for producing radiotherapy planning data required for radiotherapy of a lesion of a subject using an image formed based on X rays transmitted through the subject, said image including a plurality of axial images and either one of a scanogram and an alternative image of the scanogram, said system comprising: means for defining an isocenter of a target volume enclosing the lesion on the basis of both of at least one of the plurality of axial images and either one of the scanogram and the alternative image, means for producing a transmission image of the target volume of the subject using the plurality of axial images, said the transmission image being viewed through from a virtual radiation source virtually positioned, means for defining a contour of a radiation field on the subject on the basis of a contour of the target volume using the transmission image, means producing a target image whose plane is parallel with a cross section including the isocenter, is perpendicular to an axis from the virtual radiation source, and is defined according to a distance from the virtual radiation source using the plurality of axial images, means for confirming the radiation field using the target image, and means for confirming beam fan lines of radiation from the virtual radiation source through the radiation field using the plurality of axial images.

Further, a radiotherapy planning CT system for producing radiotherapy planning data required for radiotherapy of a lesion of a subject using an image formed based on X rays transmitted through the subject, said system comprising: means for producing the radiotherapy planning data including data of a radiation field of the subject and beam fan lines of radiations emanating from a virtual radiation source using images obtained based on the transmitted X-rays, said images including a plurality of axial images of the subject, either one of a scanogram of the subject and an alternative image of the scanogram, and images processed from the plurality of axial images; means for displaying the produced beam fan lines of radiations on a monitor; means for manually changing positions of the beam fan lines displayed on the monitor; and means for correcting data of the contour of the radiation field corresponding to a changed positional value of the beam fan lines.

According to another aspect, of the present invention a radiotherapy apparatus in which radiation from a radiation source are limited into a given size of a radiation field by an adjustable opening of a multileaf-type collimator and the limited radiations is directed onto a subject laid on a slewing couch, the apparatus comprising: means for receiving at least one of a control data of the opening and a control data of a slewing angle of the couch, the control data being produced outside the radiotherapy apparatus; and means for controlling at least one of the multileaf collimator and the couch on the basis of the received control data.

According to another aspect, there is provided a radiotherapy for planning radiotherapy of a subject using a monitor, comprising: means for producing a side-view scanogram and a three-dimensional image data of the subject with a procedure including irradiating X-rays to the subject; means for displaying the side-view scanogram on the monitor; means for use in designating a slice position along a given axis of the subject on the monitor; means for setting a position of a virtual radiation source; means for computing data a projection image projected to a cross section within the subject using the three-dimensional image data, said cross section being determined in accordance with the slice position and the position of the virtual radiation source; means for determining beam fan lines of radiation from the radiation source; and means for displaying the projection image together with the beam fan lines on the monitor.

As a result, an image rendering a cross section defined with a radiation source and a slice position designated in a side-view scanogram can be displayed together with beam-fan lines. Beam-fan lines will therefore not be inconsistent with an image but can be understood easily. This results in higher-precision therapy planning.

There is also provided a radiotherapy planner for planning radiotherapy of a subject using a monitor, comprising: means for producing a transmission image of the subject along a given axis of the subject and an axial image of the subject; first means for displaying the transmission image on the monitor; means for use in designating a contour of a radiation field on the transmission image; second means for displaying the axial image on the monitor; means for use in designating positions of beam fan lines of radiation from a virtual radiation source according to the contour of the radiation field; and third means for displaying on the monitor the transmission image superimposing the radiation field thereon together with the axial image superimposing the beam fan lines thereon.

Beam-fan lines are delineated in an image other than an image rendering a plane perpendicular to a body axis of a subject. Plan information and image information can be viewed through the same screen simultaneously. Moreover, when the positions of beam-fan lines are changed in the screen, the contour of a radiation field is soon corrected accordingly. This contributes to improvement of planning operability and leads to more accurate planning.

Furthermore, there is provided a radiotherapy planner for planning radiotherapy of a subject using a monitor, in which image data acquired through directing X rays into a lesion of the subject are given, the planner comprising: first means for producing a three-dimensional image data of a region including the lesion on the basis of the image data; means for defining a position of a virtual radiation source for the radiotherapy; second means for producing image data of a beam's path plane using the three-dimensional image data, said beam's path plane passing through the position of the virtual radiation source and being parallel with beam fan lines emanating from the virtual radiation source; and means for displaying on the monitor the image data of the beam's path plane superimposed with data of the beam's fan lines.

Further, a radiotherapy planner for planning radiotherapy of a subject, in which opening data required to control an opening formed by a collimator are produced for limiting radiation from a virtual radiation source and a three-dimensional image data of the subject is given, the planner comprising: means for producing and displaying three-dimensional surface image of the subject using the three-dimensional image data; means for accepting the opening data as a contour of a region of interest; means for correcting a size of the contour of the region of interest in conformity with both a distance from the virtual radiation source to a position of the surface image and a specified distance below the surface image; and means for producing and displaying a drilling image corresponding to the corrected contour of the region of interest.

A ROI is defined in line with the opening of a collimator. The contour of the ROI is corrected according to a distance from a radiation source and a designated depth from a body surface. A drilling image is produced on the basis of the corrected contour of the ROI and then displayed. This is effective in visualizing a deep-seated lesion of a subject.

A radiotherapy planner for planning radiotherapy of a subject using a monitor, in which a three-dimensional image data of a subject is given by a procedure including directing X rays into the subject, the planner comprising: means for producing a maximum-value projection image viewed from a given radiation source position through the three-dimensional image data; means for displaying the maximum-value projection image on the monitor; and means for making radiotherapy planning information including a radiation field and an irradiation direction of radiation carrying out the radiotherapy.

As a result, a maximum-value projection image, which corresponds to a fluoroscopic image projected from a desired position of a radiation source and is produced by processing voxel data concerning a subject, is displayed and used for therapy planning including defining of a radiation field and determination of an irradiation direction. A radiation field can therefore be defined in any direction irrespectively of a direction of acquiring image data. In addition, an irradiation direction can be identified easily.

As further aspects of the present invention, a radiotherapy planner for planning radiotherapy of a subject based on an image of the subject and having a monitor, the planner comprising: means for acquiring and displaying a scanogram of the subject; means for use in designating a radiation field and an isocenter in the displayed scanogram; means for aligning a reconstruction center for constructing said image with a plane containing the isocenter; and means for commanding an X-ray scan for acquiring said image in conformity with the reconstruction center.

Further, a radiotherapy planner for planning radiotherapy of a subject, in which a monitor is arranged, the planner comprising: means for acquiring and displaying a scanogram of the subject; means for use in designating a radiation field and an isocenter in the displayed scanogram; means for aligning a reconstruction center with a plane containing the isocenter; and means for helical-reconstructing a helical scan data into a radiotherapy planning image in conformity with the reconstruction center.

Furthermore, a radiotherapy planner for planning radiotherapy of a subject based on an image acquired by irradiating the subject with X rays, said radiotherapy being carried out by a radiotherapy apparatus arranged separately from the radiotherapy planner, said radiotherapy apparatus incorporating a multileaf-type collimator having a plurality of pairs of leaves, the radiotherapy planner comprising: means for computing a projection data projected on a cross section contained in every volume along a direction of a radiation path using image data contained in the volume, said volume being shadowed by each of the plurality of pairs of leaves; means for superimposing beam fan lines of the radiation path on the projection data; and means for displaying, including a monitor, the projection data superimposed with the beam fan lines on the monitor.

In consequence, for producing images employed in therapy planning, scan planning is performed in consideration of an isocenter and a reconstruction center and then X-ray scanning is carried out according to the scan plan. Alternatively, scanning is performed so that a CT image rendering an isocenter can be acquired, that the isocenter will be consistent with the reconstruction center, and that for the gantry will be tilted to have the same angles as radiation paths in order to visualize regions away from the isocenter. This leads to more accurate radiotherapy planning.

Further, an image rendering a volume that is exposed to radiation by a pair of leaves of a multileaf collimator can be displayed. The opening defined by the pair of leaves that is an interleaf opening can be adjusted through a screen. This is very useful and contributes to quicker and higher-precision therapy planning.

BRIEF DESCRIPTION OF THE DRAWINGS

In the drawings:

FIG. 12 is an explanatory diagram concerning scanoscopic planning;

FIGS. 15A and 15B are explanatory diagrams concerning scanoscopic planning;

FIG. 34 is a flowchart partially showing automatic correction of a radiation field;

FIG. 46 is a flowchart describing therapy planning in the third embodiment;

FIG. 55 is a flowchart of a sub-program showing confirmation and/or correction of beam fan lines and a radiation field;

FIGS. 60A and 60B are explanatory diagrams concerning drilling;

FIGS. 63A to 63D are explanatory diagrams concerning a procedure of producing a normal maximum-value projection image;

FIG. 67 shows the configuration of a facility for producing maximum-value projection images in the first example of the sixth embodiment;

FIG. 68 shows the configuration of a facility for producing maximum-value projection images in the second example of the sixth embodiment;

FIG. 69 shows the configuration of a facility for producing maximum-value projection images in the third example of the sixth embodiment;

DETAILED DESCRIPTION OF THE PREFERRED EMBODIMENTS

Referring to FIGS. 2 to 36, an embodiment of a radiotherapy system in accordance with the present invention will be described.

Figure 1:
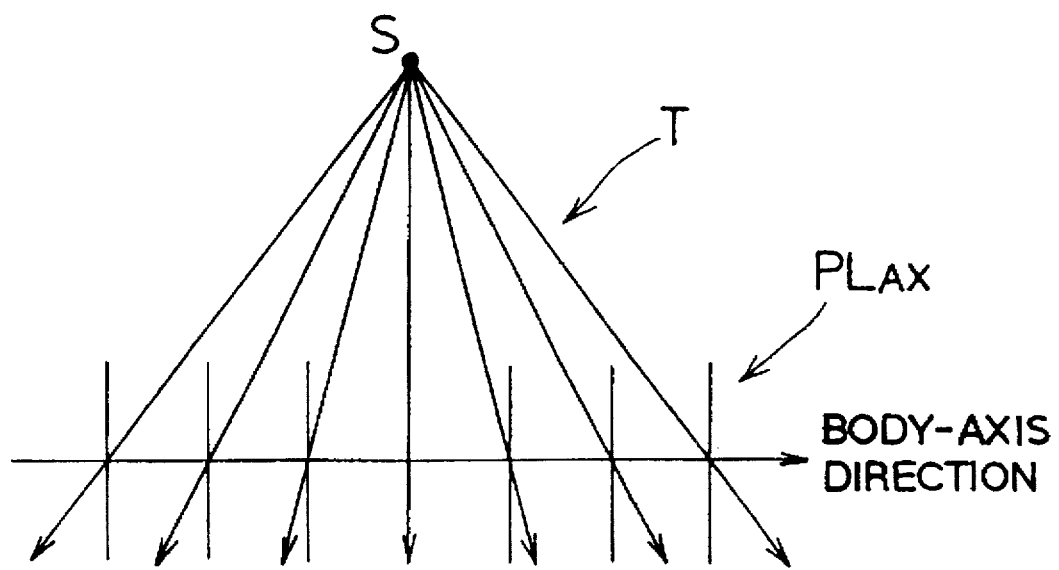
FIG. 1 is an explanatory diagram concerning an example of a problem underlying prior art.
Figure 2:
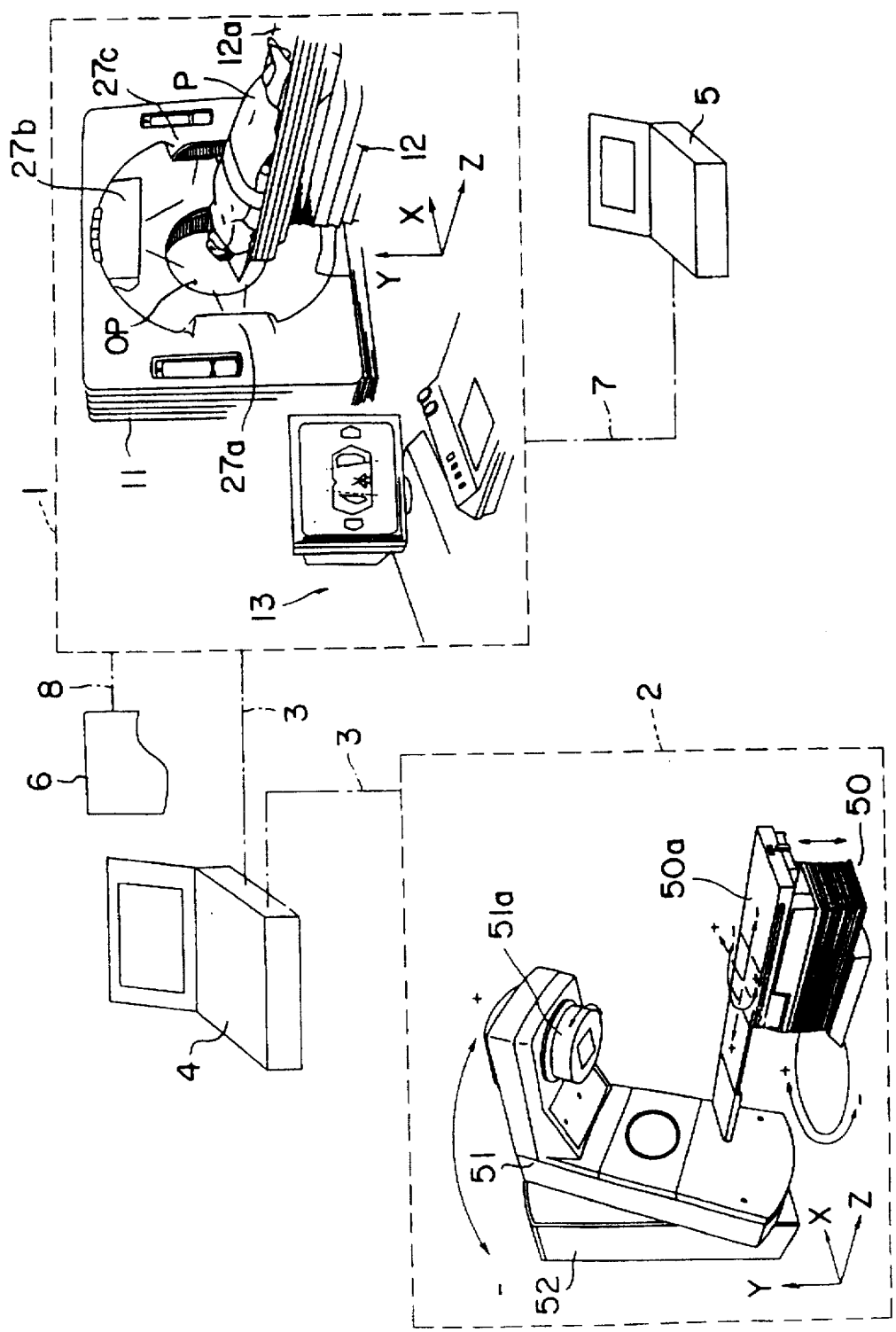
FIG. 2 is a schematic view showing the overall configuration of a radiotherapy system in accordance with the first embodiment of the present invention.
Figure 3:
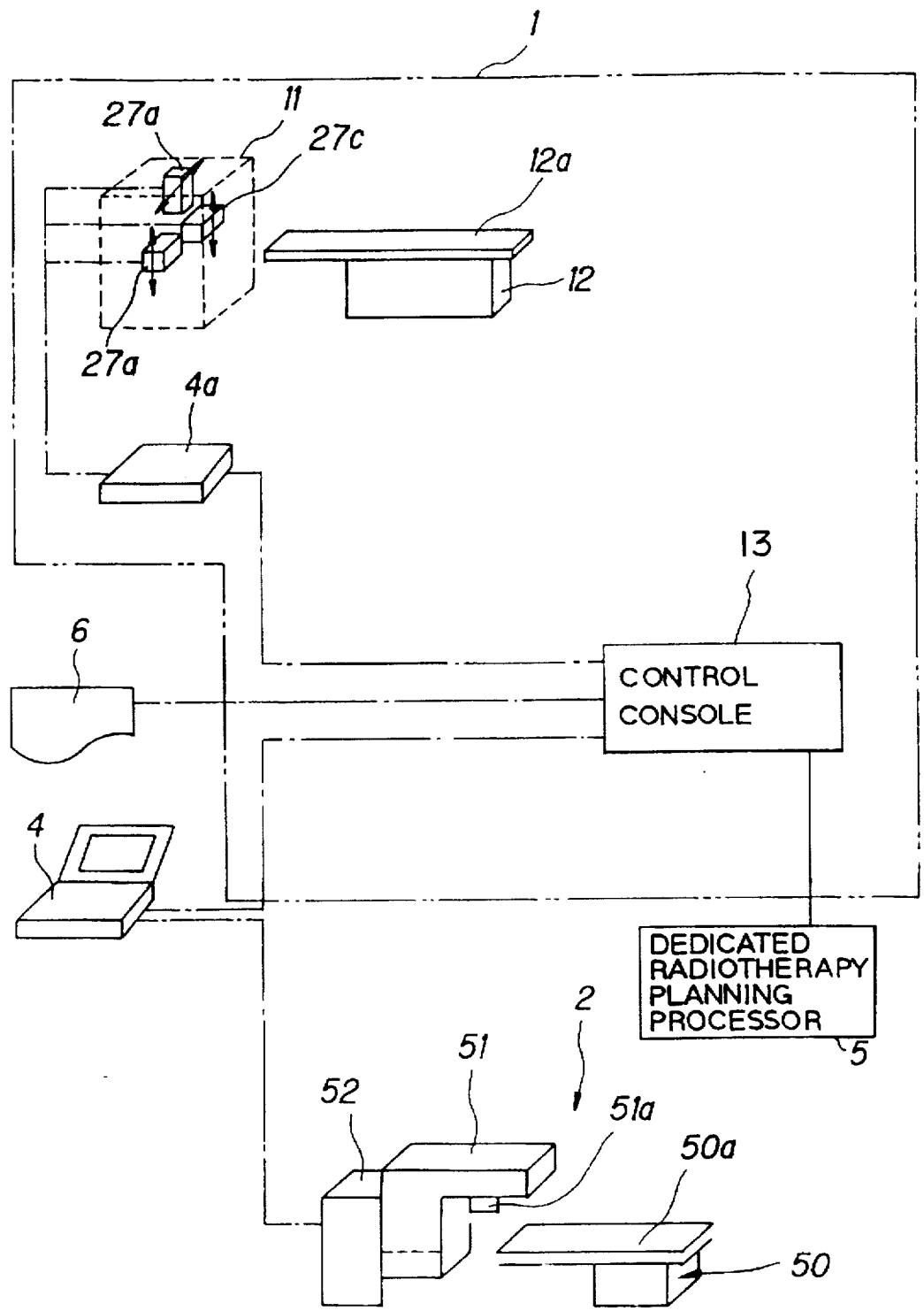
FIG. 3 is a block diagram showing overall electrical connections.

FIGS. 2 and 3 show the overview of a radiotherapy system. The radiotherapy system comprises a radiotherapy planning CT system 1 for achieving a radiotherapeutic procedure ranging from image acquisition through therapy planning to positioning (simulation), and a radiotherapy apparatus 2 for accomplishing radiotherapy on the basis of the therapy plan data resulting from planning and simulation performed by the radiotherapy planning CT system 1. For automatically controlling a collimator, which will be described later, incorporated in the radiotherapy apparatus 2, a coaxial cable 3 serving as a signal transmission line is used to link the radiotherapy planning CT system 1 and radiotherapy apparatus 2. In the middle of the coaxial cable 3, a verification recorder 4 is placed so that an operator can finely adjust the opening of the collimator optimally for actual radiotherapy. A dedicated therapy planning processor 5 responsible for expert computations including calculation of radiation dose distribution and a laser printer 6 for outputting plan data are connected to the radiotherapy planning CT system 1 by way of transmission lines 7 and 8.

Among the above component elements, the radiotherapy planning CT system 1 (hereinafter, CT system) will be described.

Figure 4:
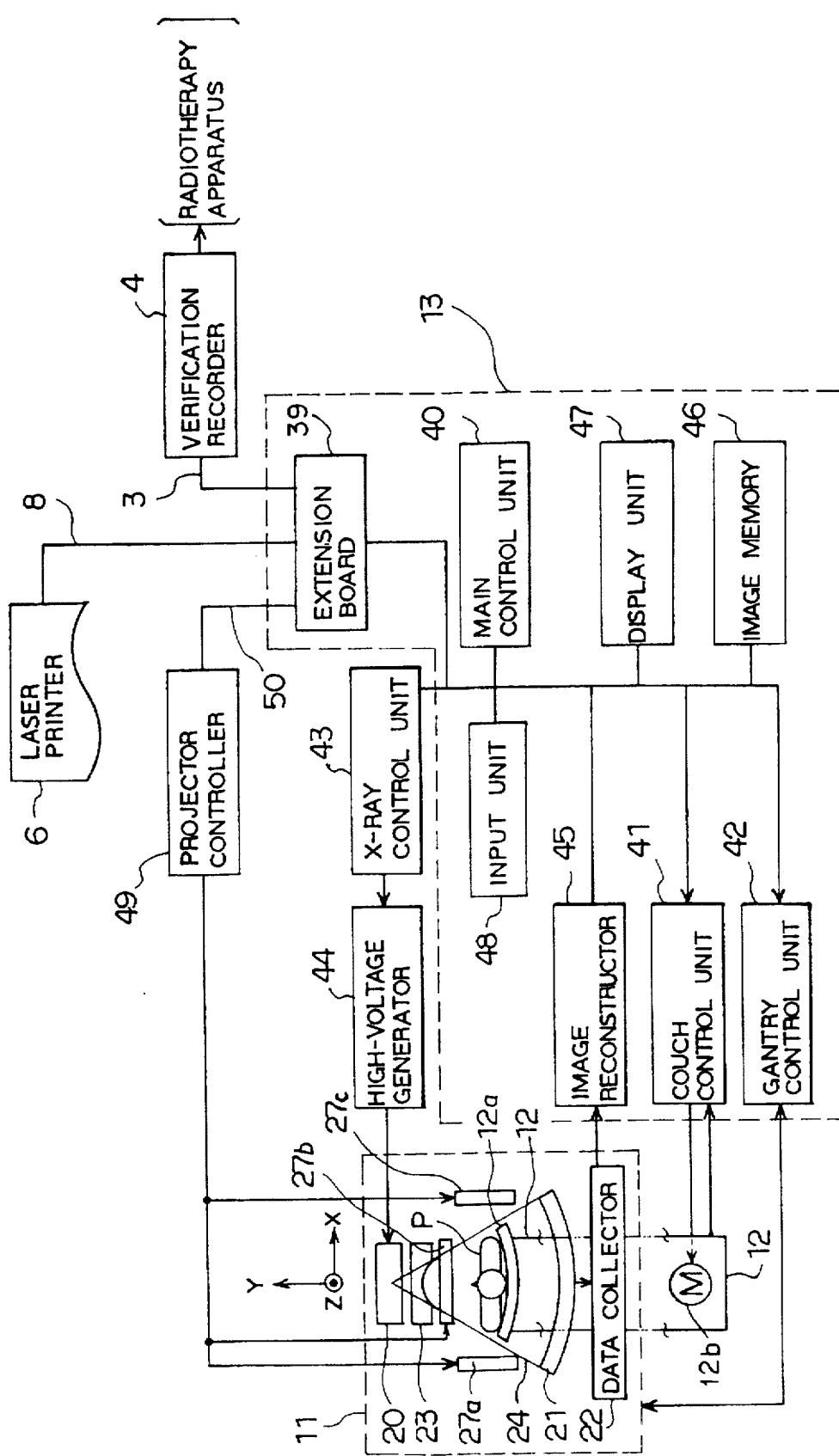
FIG. 4 is a block diagram schematically showing a radiotherapy planning CT system.

The CT system 1 is configured using an ordinary X-ray CT scanner. As shown in FIGS. 2 and 4, the CT system 1 comprises a gantry 11, a patient couch 12, and a control console 13, and is driven according to, for example, a rotate-rotate method. A couchtop 12a is placed on the top of the couch 12 and supported so that it can slide in the longitudinal (z (body) axis) direction. A subject P lies down on the top of the couchtop 12a. The couchtop 12a is driven by a sliding mechanism represented by an electric motor 12b and thus inserted to a diagnostic opening OP of the gantry 11 so that it can advance or withdraw freely.

An X-ray tube 20 and an X-ray detector 21 that are opposed to each other with the subject P inserted to the opening OP between them are, as shown in FIG. 4, incorporated in the gantry 11. A weak electric current that is comparable to transmitted X rays detected by the X-ray detector 21 is converted into a digital signal by a data collector 22. The digital signal is then sent to the console 13. In FIG. 4, reference numeral 23 denotes a collimator and a filter in the gantry 11, and reference numeral 24 denotes an X-ray fan.

Three positioning projectors 27a, 27b, and 27c are placed inside a front cover 11a that is the front surface of the gantry 11 and facing the patient couch 12. The positioning projectors 27a to 27c are located at positions of a given height by the right and left sides of the diagnostic opening OP and at a center position above the diagnostic opening OP. The emission ports of the projectors 27a to 27c are directed to the subject P advancing to the diagnostic opening OP.

Figure 5:
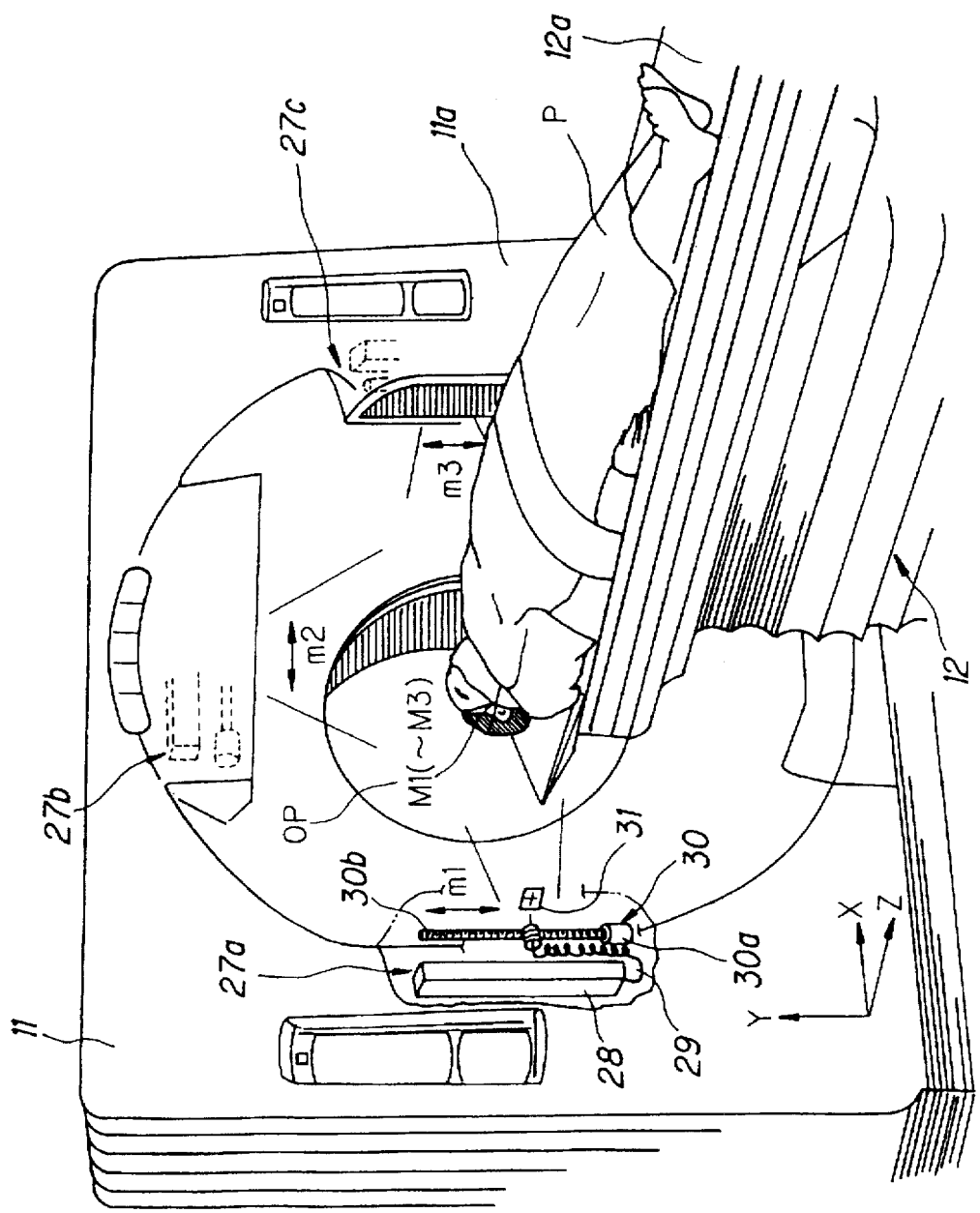
FIG. 5 is a perspective view showing a gantry and the states of mounted positioning projectors for marking an isocenter.

Each of the positioning projectors 27a to 27c in this embodiment is of a laser type and essentially composed, as shown in FIG. 5, of a laser source 28 using, for example, helium and neon, an optical fiber 29 for routing an output beam of the laser source 28, a moving mechanism 30 for moving the distal end of the optical fiber 29 in a direction predetermined in line with the position of a positioning projector (that is to say, in an y-axis direction for the right and left positioning projectors 27a and 27c, and in an x-axis direction for the upper center positioning projector 27b), and a light emitter 31 for creating a cross mark using the output beam of the optical fiber 29 and emitting it toward the subject P. The moving mechanism 30 includes, for example, a step motor 30a and a lead screw 30b to be rotated by the motor 30a. With the forward or reverse rotation of the step motor 30a, the distal end of the optical fiber 29 that is the light emitter 31 moves in the y- or x-axis direction (See arrows m1 to m3 in FIG. 5). As a result, the positioning projectors 27a to 27c emit cross laser beams to the subject P through the light emitters 31, and thus form cross shades of marks M1 to M3 on the sides and top of the body surface.

The rotations of the step motors 30a of the positioning projectors 27a to 27c and the movement of the couchtop 12a are automatically controlled at the control console 13. The marks M1 and M3 formed by the right and left positioning projectors 27a and 27c are controlled so that they will be located at vertically identical positions.

Figure 6:
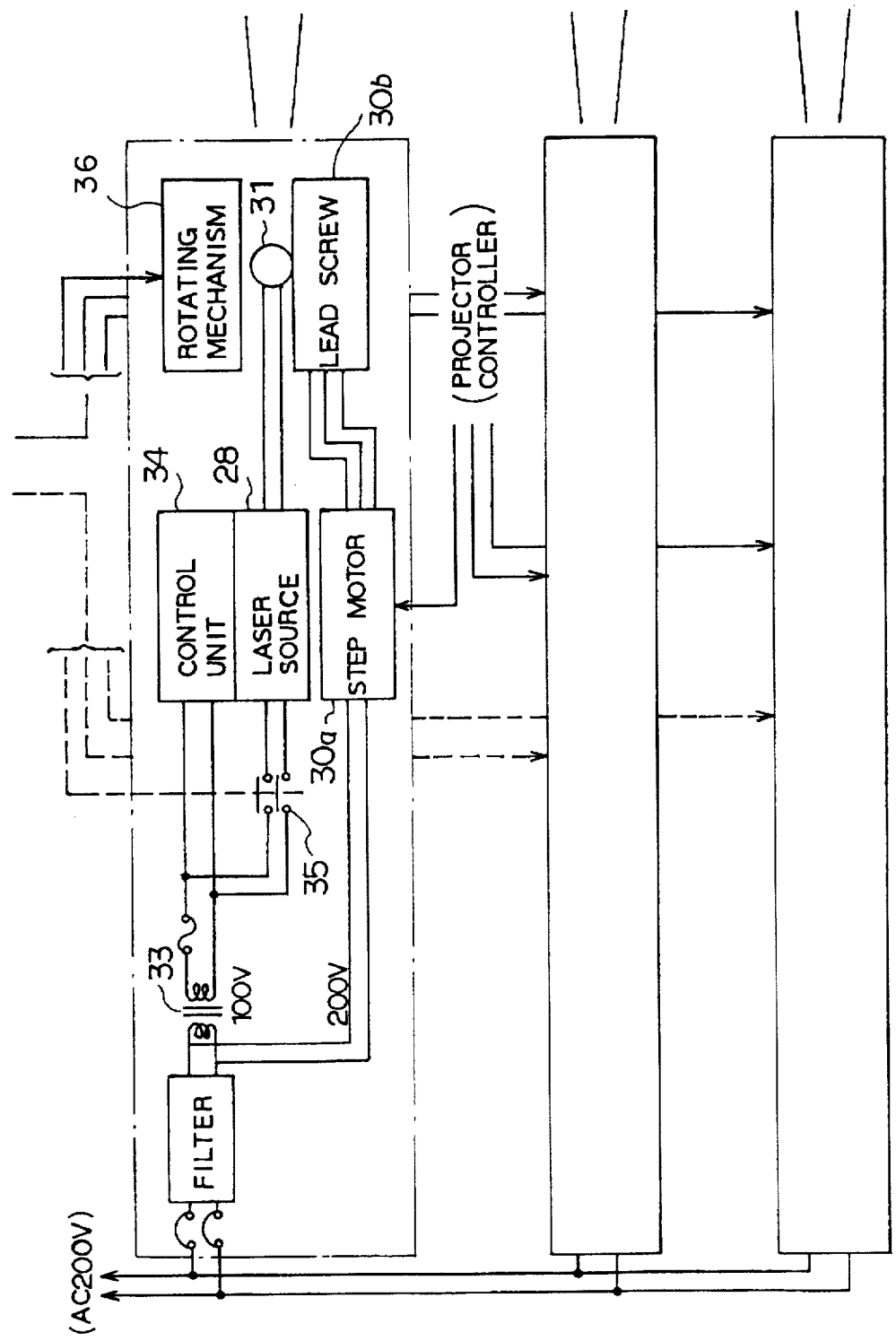
FIG. 6 is a block diagram showing an electric circuit in a positioning projector.

Each of electric circuits to the positioning projectors 27a to 27c has circuitry shown in FIG. 6. Specifically, a supply voltage of AC 200 V is stepped down to AC 100 V by means of a transformer 33, and fed to a control unit 34 for controlling the laser source 28. The stepped-down supply voltage is also fed to the laser source via an on/off switch 35. On the other hand, the supply voltage of AC 200 V is fed to the step motor 30a in the moving mechanism 30 as it is. A rotating mechanism 36 (See FIG. 6), which is not particularly shown in FIG. 5, is included to rotate the moving mechanism 30 and light emitter 31 in a united fashion with an irradiation direction as a rotation axis. The rotating mechanisms 36 are used to tile the gantry, whereby the mark emitting functions in the positioning projectors 27a to 27c can be used hot only for isocenter setting but also for patient positioning in normal operation mode. The CT system 1 in this embodiment can therefore be used not only as a radiotherapy planning CT system but also as a normal X-ray CT scanner. The rotating mechanism 36 and on/off switch 35 are controlled by a main control unit 40 when needed.

Returning to FIG. 4, it is seen that the control console 13 includes the main control unit 40 for controlling the whole of the CT system as well as a patient couch control unit 41 and a gantry control unit 42 which operate in response to a command sent from the main control unit 40. These control units are interconnected over an internal bus. The main control unit 40 is connected to an X-ray controller 43 installed outside the console. A high-voltage generator 44 operates in response to a drive signal sent from the X-ray controller 43. High voltage generated by the high-voltage generator 44 is fed to the X-ray tube 20, whereby X rays are generated. The console 13 further includes an image reconstructor 45 for reconstructing image data in response to a collection signal sent from the data collector 22, an image memory 46 for storing image data, a display unit 47 for displaying reconstructed images, and an input unit 48 allowing an operator to enter a command to be sent to the main control unit 40. Each of the control units and controller 40 to 43 has a computer and operates according to programs stored in a memory in the computer.

The internal bus of the console 13 is joined with an extension board 39 of coaxial cables. A projector controller 49 for controlling the positions at which the positioning projectors 27a to 27c project marks is connected to the extension board 39 by way of a coaxial cable 50. The laser printer 6 and verification recorder 4 are connected to the extension board 39 by way of coaxial cables 8 and 3. Position data concerning an isocenter to be placed on a subject is supplied from the main control unit 40 to the projector controller 49. In response to the data, the projector controller 49 automatically controls the positions of the light emitters 31 in the positioning projectors 27a to 27c.

The verification recorder 4 is realized with, for example, a personal computer. For radiotherapy, an operator uses the verification recorder 4 to re-verify the opening of the collimator in the radiotherapy apparatus 2 and finely adjust the opening if necessary. Moreover, an irradiation dose and irradiation information can be set or modified by means of the verification recorder 4.

Next, the radiotherapy apparatus 2 will be described.

Figure 7:
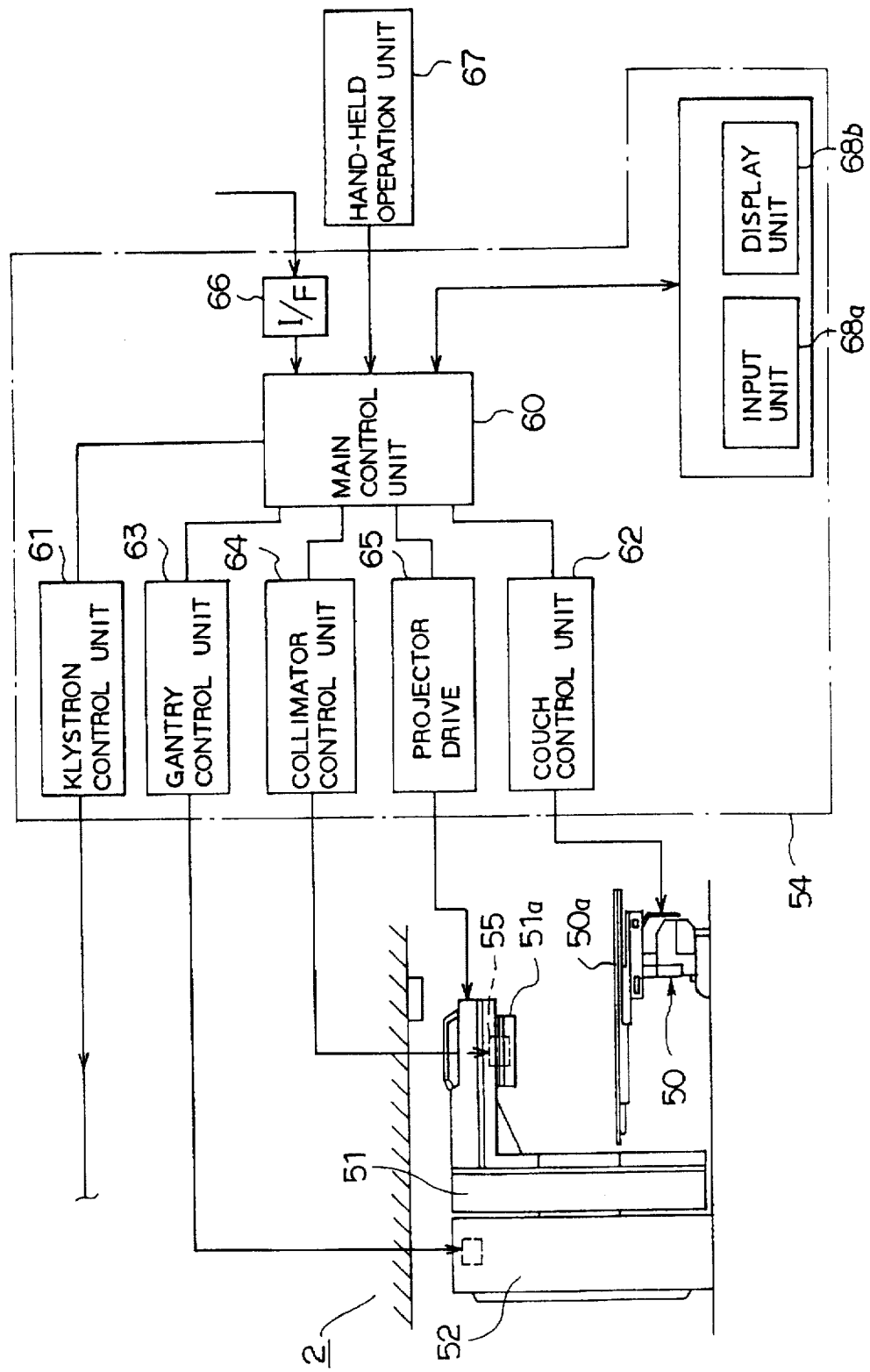
FIG. 7 is a block diagram schematically showing a radiotherapy apparatus.

The radiotherapy apparatus 2 in this embodiment uses X rays for treatment, and comprises, as shown in FIGS. 2 and 7, a patient couch 50 on which a subject P lies down, a gantry 51 rotatable with a body axis (z-direction) of the subject P as a rotation axis, a gantry support column 52 for supporting the gantry 51 so that the gantry 51 can rotate, and a console 54 (See FIG. 7).

The patient couch 50 has a couchtop 50a placed thereon. The height of the patient couch 50 is adjustable by means of an internal driving mechanism, whereby the couchtop 50a can be moved vertically (in the y-axis direction). With a drive given by another internal driving mechanism, the patient couch 50 causes the couchtop 50a to move within a given range in the longitudinal (z-axis) direction or lateral (x-axis) direction. Actuated by yet another driving mechanism, the patient couch 50 causes the couchtop 50a to turn around a couchtop support or an isocenter. These operations of the patient couch 50 are required for positioning of the subject P on the couchtop 50a or for irradiation, and are controlled with a control signal sent from the console 54.

Figure 8:
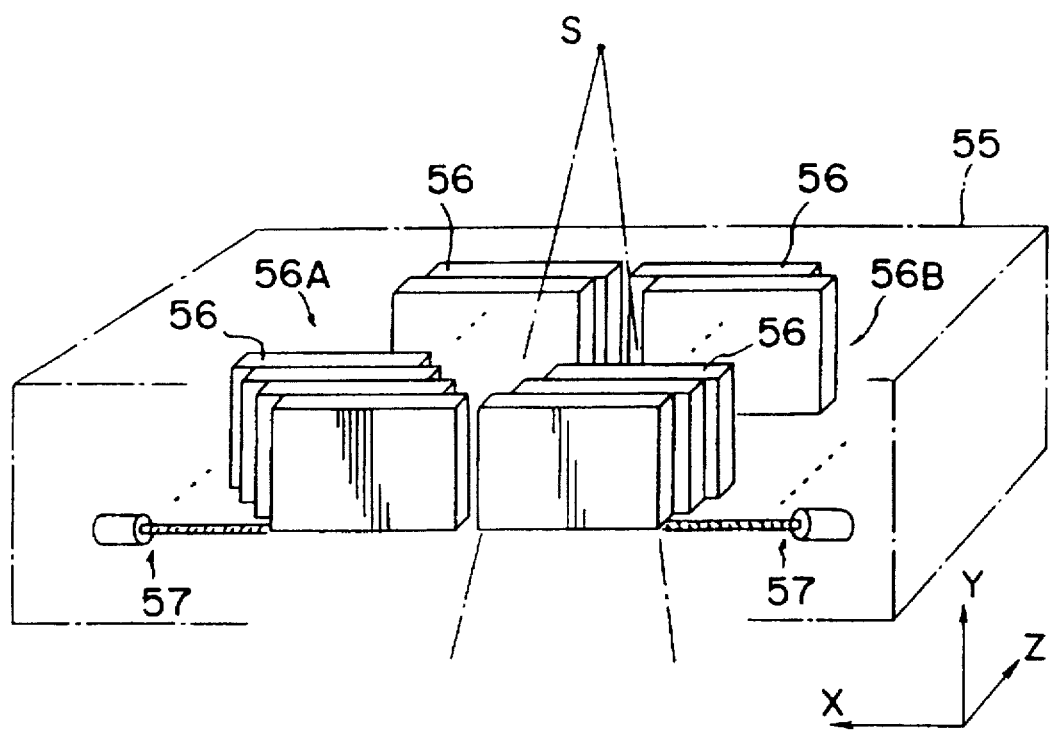
FIG. 8 is an explanatory diagram concerning a multileaf collimator.

The gantry 51 includes an irradiation head 51 a which deflects accelerated electrons emanating from a Klystron tube so that the electrons will hit a target therein to generate X rays and which then uses the X rays to irradiate the subject P. The irradiation head 51a has a collimator 55, which defines a radiation field on the body surface of the subject P. interposed between the target that is a radiation source and an irradiation port. In this embodiment, the collimator 55 is a multileaf collimator having the structure of a multileaf diaphragm. That is to say, as shown in FIG. 8, two groups of leaves 56A and 56B each consisting of a plurality of plate-like tungsten leaves 56 (for example, 29 leaves) are upright and opposed to each other with an X-ray path originating from a radiation source S between them. The leaves 56 can be driven independently in the longitudinal (x-axis) direction thereof by means of moving mechanisms 57 each including a lead screw. The moving mechanisms 57 are driven according to a control signal sent from the console 54, thus changing the size or contour of an aperture defined with the two groups of leaves 56A and 56B (corresponding to the size or contour of a radiation field on a body surface) in real time.

Using a built-in driving mechanism, the gantry support column 52 causes the whole gantry 51 to rotate clockwise or counterclockwise. The actuation of the driving mechanism is based on a control signal sent from the console 54.

The console 54 includes, as illustrated, not only a main control unit 60 for controlling the whole of the radiotherapy apparatus 2 but also a Klystron control unit 61, patient couch control unit 62, gantry control unit 63, collimator control unit 64 and a projector drive 65 each of which processes an assigned job in response to an instruction sent from the main control unit 60. The projector drive 65 drives three positioning projectors (not shown) mounted favorably in the gantry 51. The subject P on the couchtop 50a is positioned so that the positions indicated by the three positioning projectors will become consistent with cross markers M1 to M3 already drawn on the subject P. Thus, an isocenter of the subject P coincides with the rotation center of the radiotherapy apparatus 2.

The control units 60 to 64, for example, share the same single computer and operate according to programs stored in a memory in the computer. The main control unit 60 is connected to the verification recorder 4 via an interface circuit 66, so that the main control unit 60 can receive opening data (a rotation angle data of the collimator and position data of each leaf) concerning the collimator 55. The main control unit 60 is connected to an input unit 68a such as a keyboard and a display unit 68b including a CRT, and also connected to a hand-held operation unit 67. The hand-held operation unit 67 is hung in the vicinity of the patient couch 50, thus realizing improved operational convenience.

Next, the operation of the present invention will be described in conjunction with flowcharts.

Figure 9:
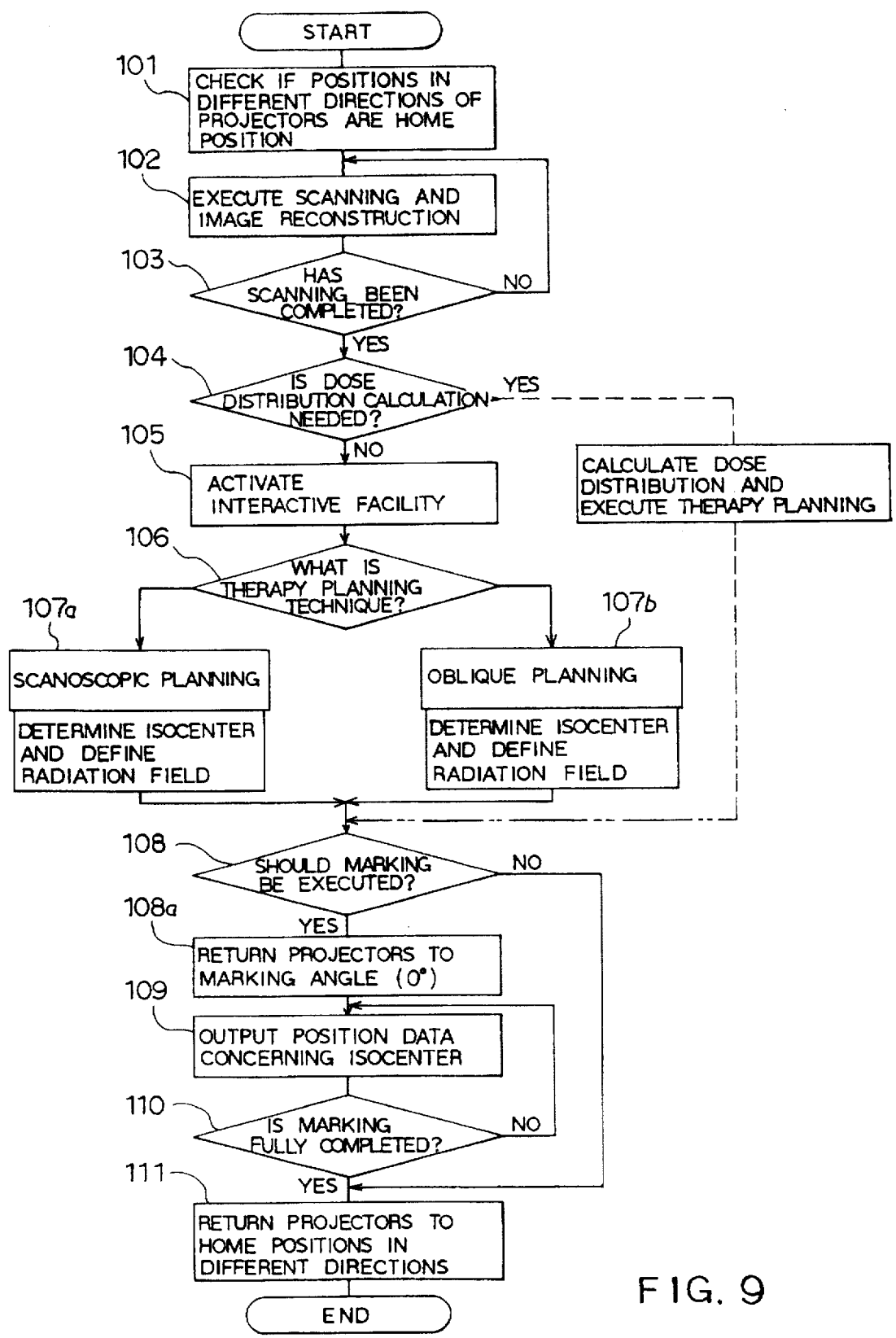
FIG. 9 is a flowchart describing the whole of a therapy planning procedure.

FIG. 9 shows an overall procedure ranging from scanning for acquiring images of a region to be treated to therapy planning. The procedure mainly involves the console 13 in the CT system 1.

At step 101 in FIG. 9, it is checked if the positions in different directions of the positioning projectors 27a to 27c are home positions. At step 102 and thereafter, control is passed to therapy planning. First, at step 102, the main control unit 40 issues, for example, a helical scan command to each of the patient couch control unit 41, gantry control unit 42, and X-ray control unit 43 so that helical scanning will be executed. Based on the collected data provided by the data collector 22, the main control unit 40 issues an image reconstruction command to the image reconstructor 45. Thus, image data representing a volume containing a region to be treated is provided as data concerning a plurality of axial images. Prior to the helical scanning, a scanogram (fluoroscopic image) of the region to be treated is produced.

When it is determined at step 103 that the scanning sequence and image reconstruction have been completed, control is passed to step 104. It is then determined whether calculation for dose distribution is needed. The calculation for dose distribution is often performed for the sake of confirmation when a region to be treated is an unprecedented one that is excluded from a clinical routine. The main control unit 40 determines based on command information entered by an operator at the input unit 48 whether the calculation is requested. If the result of determination is in the affirmative, image data is transferred online to the dedicated processor 5 and thus calculation for dose distribution is requested. In this case, the dedicated processor 5 performs the requested calculation for dose distribution and assists in determining an isocenter and an irradiation technique. The determinant data is retrieved by the CT system 1 for laser marking which will be described later.

If the result of determination made at step 104 is in the negative, calculation for dose distribution is not performed but therapy planning is commenced. Specifically, an interactive facility in the CT system is activated at step 105, and a therapy planning technique is selected at step 106. In this embodiment, two therapy planning techniques of "scanoscopic planning" and "oblique planning" are available. Either of the techniques can be selected at step 107a or 107b, respectively.

Next, scanoscopic planning that is the foregoing first therapy planning technique will be described with reference to FIGS. 10 to 20.

In the scanoscopic planning, an isocenter is determined using either or both of top(frontal)- or side(lateral)-view scanograms (when one scanogram is available, at least one axial image is needed to determine a vertical position of an isocenter). This technique is preferable for fixed irradiation (single-port or opposed dual-port irradiation) applied to the carcinoma at the uterus or pharynx. Control information concerning the multileaf collimator 55 in the radiotherapy apparatus 2 is provided.

Figure 10:
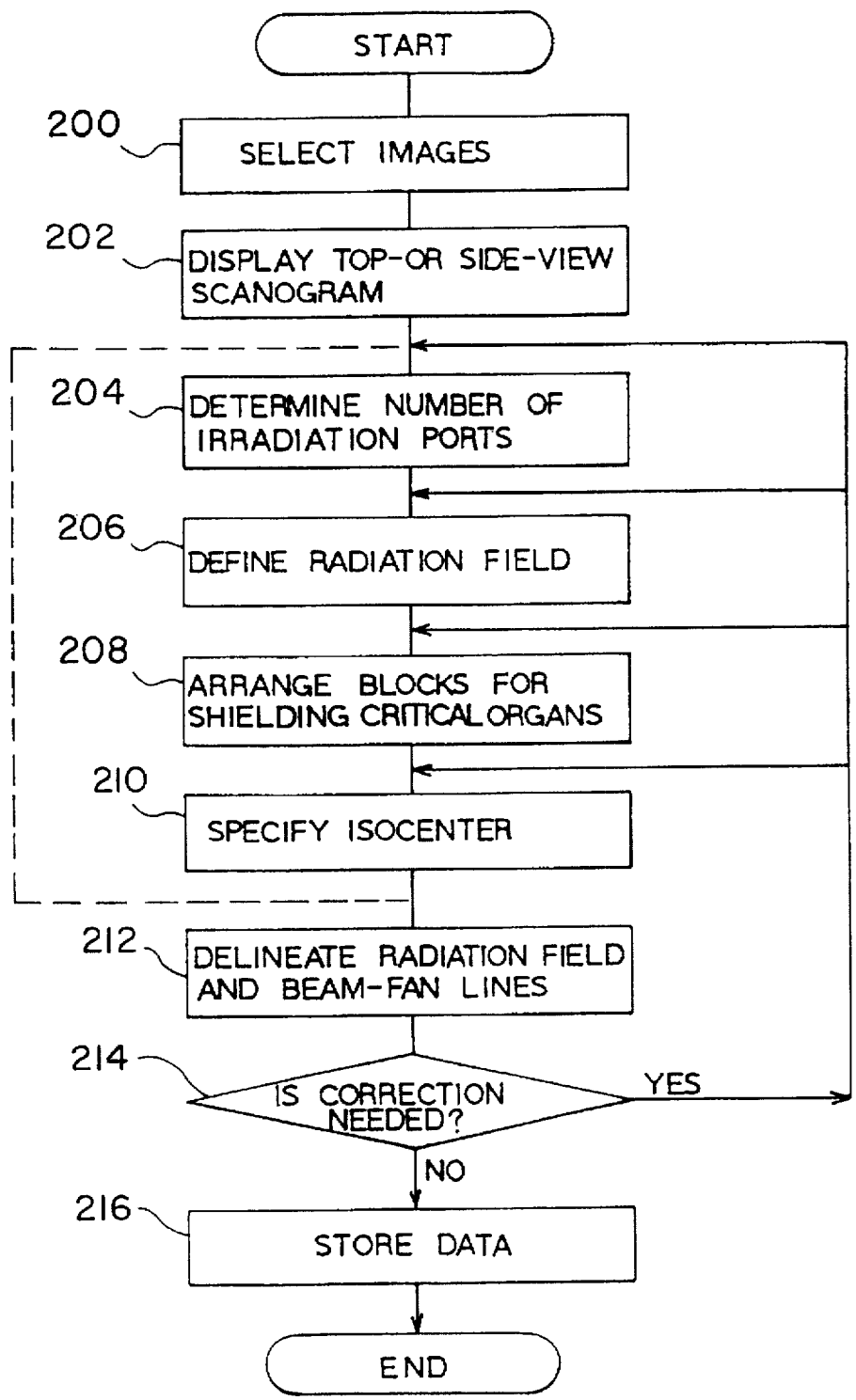
FIG. 10 is a flowchart describing a sequence of scanoscopic planning.

To be more specific, at step 200 in FIG. 10, a patient directory is used to select images of a specific patient required for planning or an image directory is used to select scanograms and axial images required for planning. In scanoscopic planning, one scanogram is used to determine a radiation field.

Figure 11A:
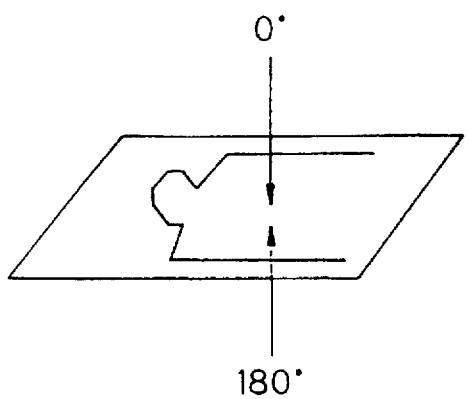
FIGS. 11A and 11B are explanatory diagrams concerning scanoscopic planning.
Figure 11B:
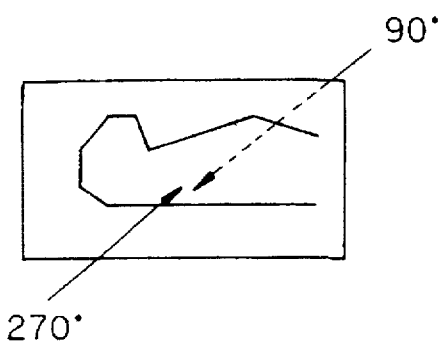

Next, at steps 202 and 204, a scanogram is displayed and the number of irradiation ports is designated. In other words, one scanogram required for scanoscopic planning is finally selected from among the group of selected scanograms and then displayed. The finally selected scanogram renders either a top view or a side view. An irradiation angle is then determined as shown in FIG. 11A or 11B. Finally, an irradiation direction and the number of irradiation ports (See FIG. 12) are determined.

Figure 13A:
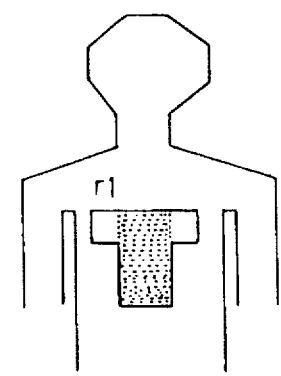
FIGS. 13A and 13B are explanatory diagrams concerning scanoscopic planning.
Figure 13B:
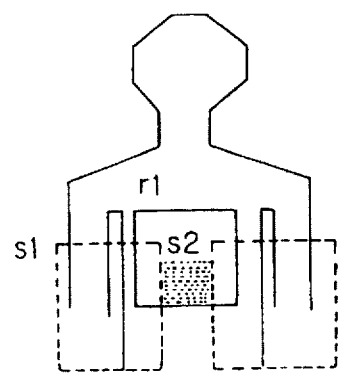

A radiation field is defined at step 206. Blocks for shielding critical organs are arranged at step 208. That is to say, the blocks for shielding critical organs are arranged in the scanogram. At this time, a polygon ROI or a rectangular ROI is selected with the contour of the radiation field. FIGS. 13A and 13B show examples of defining a radiation field for the same lesion. In FIG. 13A, one polygon ROI r1 is used. In FIG. 13B, one rectangular ROI r1 and two shielding blocks using rectangular ROIs s1 and s2 are used in combination. For the thus defined radiation field, positional and angular data concerning the leaves 56 of the collimator 55 is produced.

During the scanoscopic planning, similar to interaction for scanning, a scanogram is enlarged or reduced if necessary. A plurality of scanograms are processed, so that the contour of a radiation field can be displayed as it is during image feed (forward or backward) and a respiratory motion can be checked or corrected (however, the contour of a radiation field can be cleared if necessary). During image feed, if scanograms result from irradiation in different directions, the contour of a radiation field is deleted.

Figure 14:
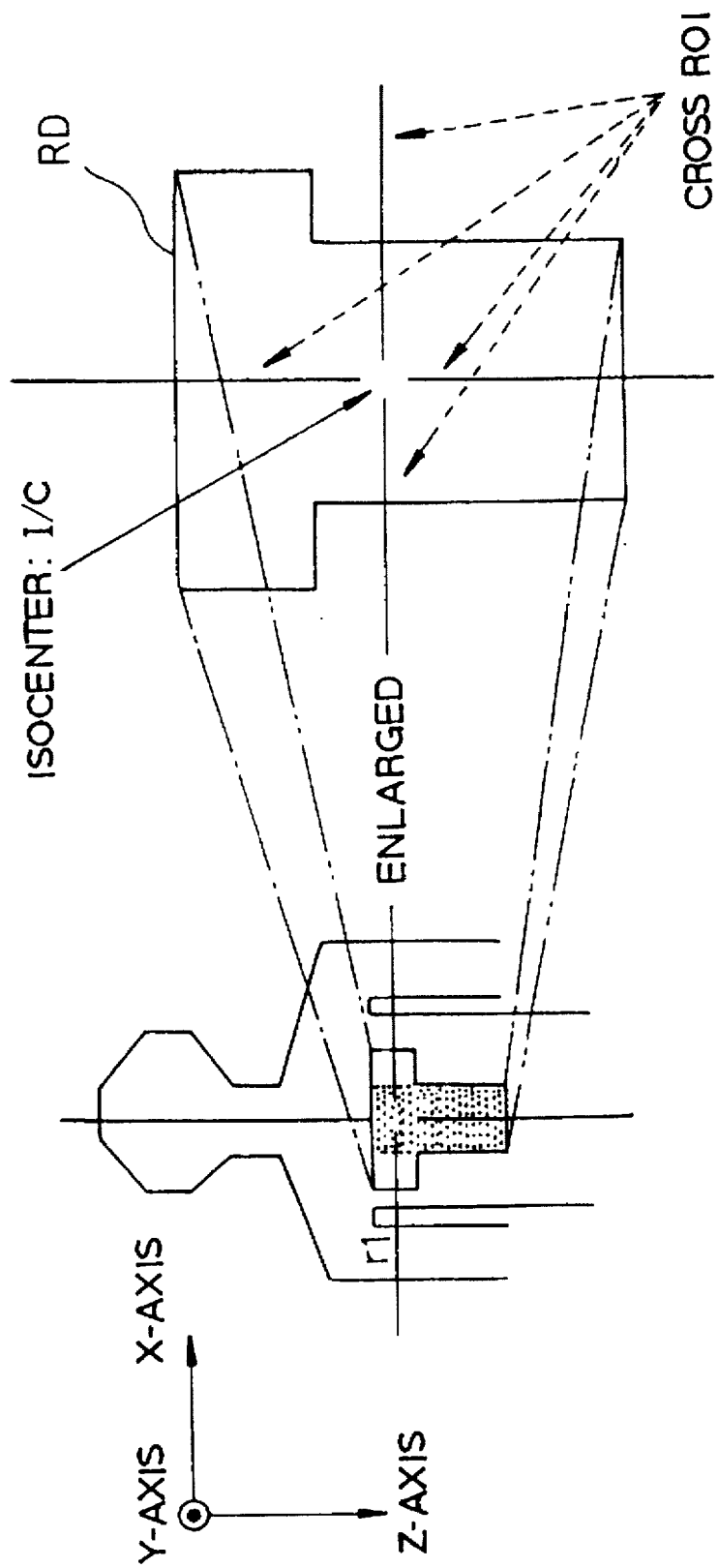
FIG. 14 is an explanatory diagram concerning scanoscopic planning.
Figure 16:
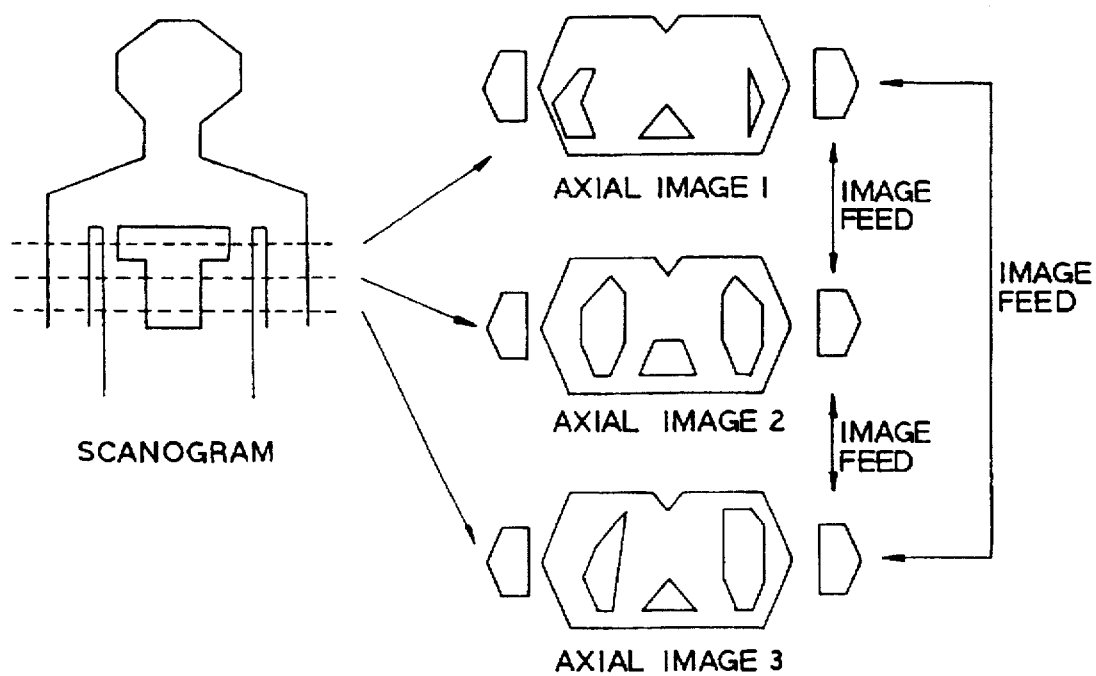
FIG. 16 is an explanatory diagram concerning scanoscopic planning.
Figure 17:
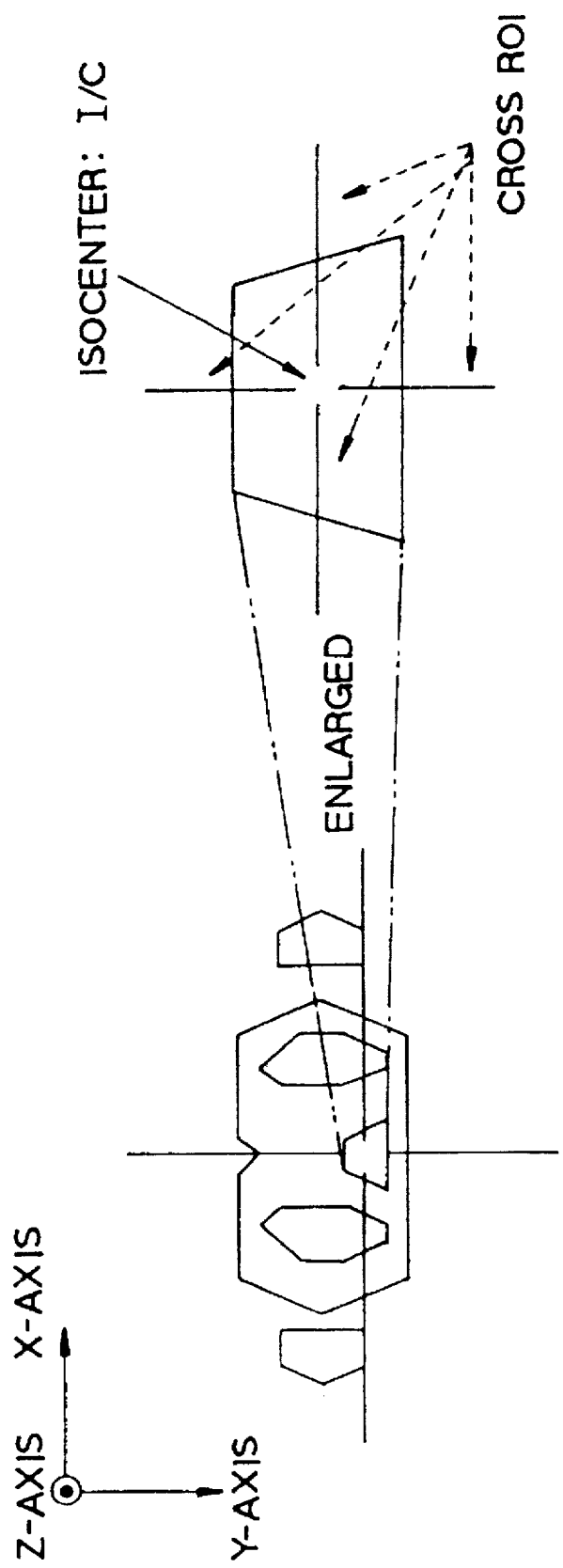
FIG. 17 is an explanatory diagram concerning scanoscopic planning.

Control is then passed to step 210. An isocenter (rotation center) I/C is set to any unique position. For this setting, first, an isocenter point on an x-z plane is specified in a scanogram displayed. A user uses a mouse to move a cross ROI (with its center vacated) displayed in the scanogram to a desired isocenter point as shown in FIG. 14 and then to finalize the point. The cross ROI is initially set to the center of a radiation field RD. At this time, the scanogram may be enlarged or reduced. Correction must be achieved easily.

When a scanogram renders a top view as shown in FIG. 15A, an x-z plane is used. When the scanogram renders a side view as shown in FIG. 15B, an y-z plane is used to specify an isocenter.

When the center of the cross ROI is vacated, candidate isocenter points can be identified with ease. Preferably, a scale in millimeters or inches should be drawn on the cross ROI.

An isocenter is specified in axial images. Specifically, any axial image is selected from among selected images (See FIG. 16), and an isocenter I/C is specified in the axial image using a mouse (See FIG. 17). Since an isocenter point on the x-z (or y-z) plane has been determined, one remaining point should fundamentally be specified. An isocenter can be corrected. Thus, x, y, and z coordinates of an isocenter are finalized.

When a scanogram renders a top (side) view, coordinates other than an y (x) coordinate have already been determined. It is convenient if determined coordinates are fixed unless otherwise designated by a user. When a top-view scanogram is used to specify an isocenter point, the y axis of a cross ROI in an axial image should be fixed and only the x axis thereof should be movable using a mouse. The same applies to the use of a side-view scanogram where the x axis would be fixed.

Figure 18:
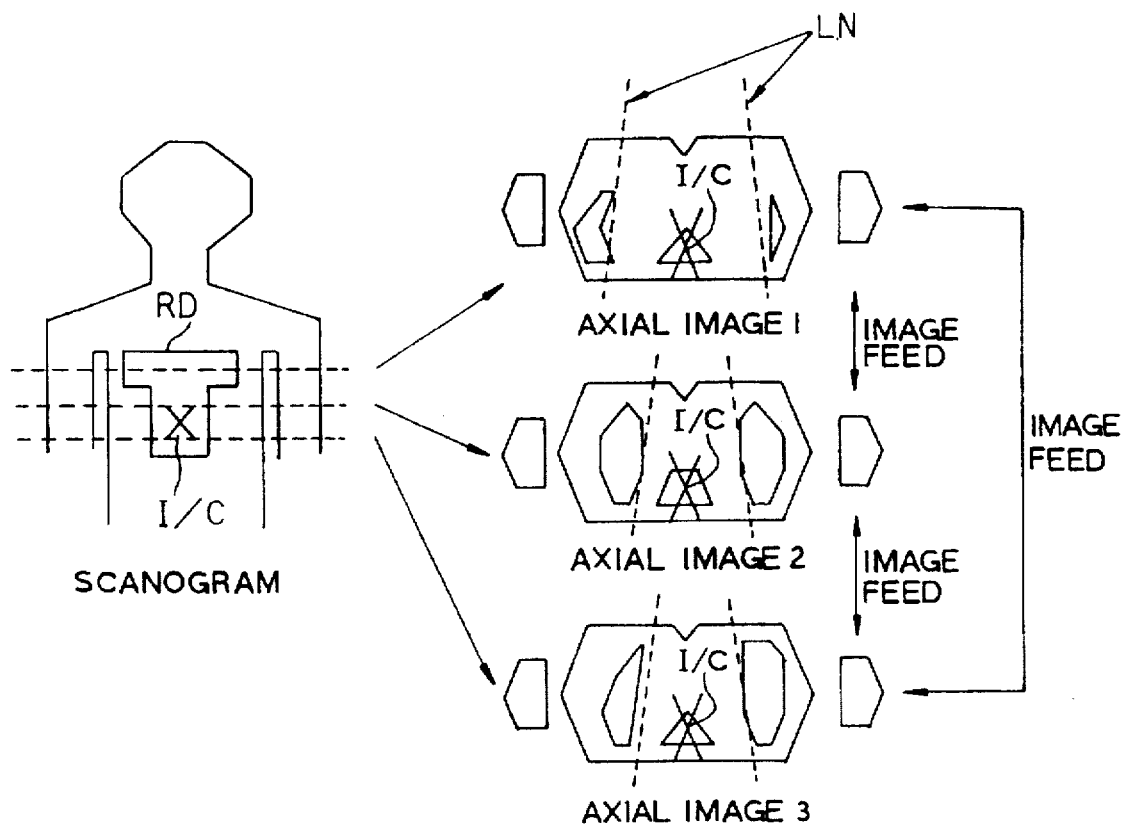
FIG. 18 is an explanatory diagram concerning scanoscopic planning.
Figure 19:
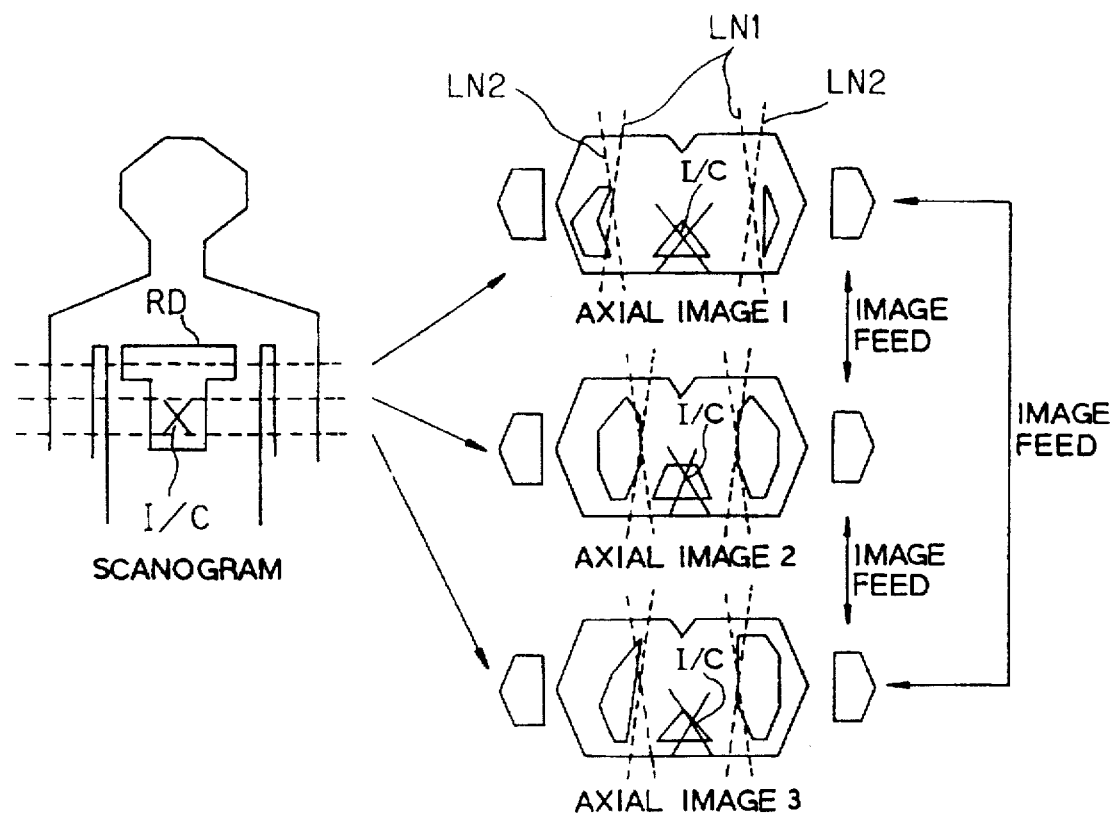
FIG. 19 is an explanatory diagram concerning scanoscopic planning.

At step 212, a radiation field RD and beam-fan lines LN are displayed. FIG. 18 shows an example of single-port irradiation. As illustrated, a radiation field RD and an isocenter I/C (indicated with X) are delineated in a scanogram. The borders of a radiation path (referred to as beam-fan lines LN) virtually originating from a radiation source via a collimator (multileaf collimator) is indicated with dashed lines in axial images. FIG. 19 shows an example of opposed dual-port irradiation. In FIG. 19, LN1 and LN2 denote beam-fan lines relevant to the two opposed ports.

The display form available should include not only a "one image per screen" form but also a multiframe (1 by 2, 2 by 2, or 2 by 2) form.

Figure 20:
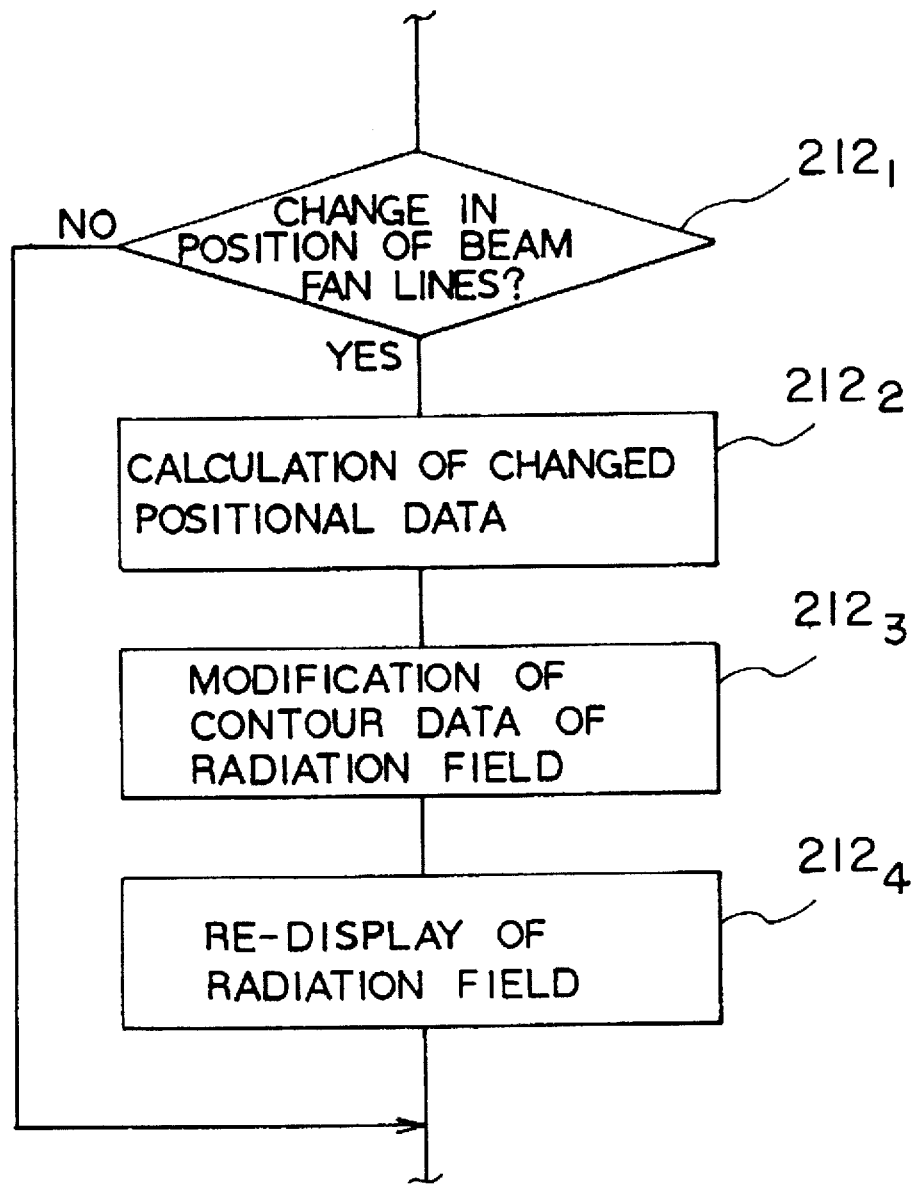
FIG. 20 is a flowchart partially showing automatic correction of a radiation field.

During displaying at step 212, when the positions of drawn beam-fan lines are changed using a pointing device (for example, a mouse), modification data concerning the contour of a radiation field is computed according to the change in positions (steps $212_1$ to $212_3$ in FIG. 20). The drawn radiation field is reformed in real time and displayed again (step $212_4$). Thus, a radiation field is automatically corrected responsively to the fine adjustment of beam-fan lines. This results in drastically improved operability. This fine adjustment and automatic correction facility at step 212 may be removed, if unnecessary.

When a radiation field RD and beam-fan lines LN have been displayed, at step 214, an operator finally and totally checks them in the screen and determines whether the radiation field or beam-fan lines should be corrected. If the result of determination is in the negative (correction is not needed), the data concerning the radiation field RD, isocenter I/C, and irradiation parameters are stored at step 216. If the result of determination made at step 214 is affirmative (correction is needed), control is returned to any required step of steps 204 to 210. The aforesaid sequence is repeated. Steps 204 to 210 need not be carried out in the same order as the one illustrated but may be reordered arbitrarily.

Oblique planning is the second therapy planning technique and will be described in conjunction with FIGS. 21 to 34. Oblique planning is employed when the employment of the aforesaid scanoscopic planning technique does not enable planning. A plurality of target volumes or critical organs can be traced accurately using ROIs. A plurality of axial images are used to produce and display transmission and target-volume images relative to virtual radiation sources (angled arbitrarily, wherein each axial plane shall contain the center of rotation of a source). It can therefore be understood accurately whether beam irradiation or a safety margin is appropriate. Moreover, information concerning multiport irradiation and control of a collimator can be provided.

Figure 21:
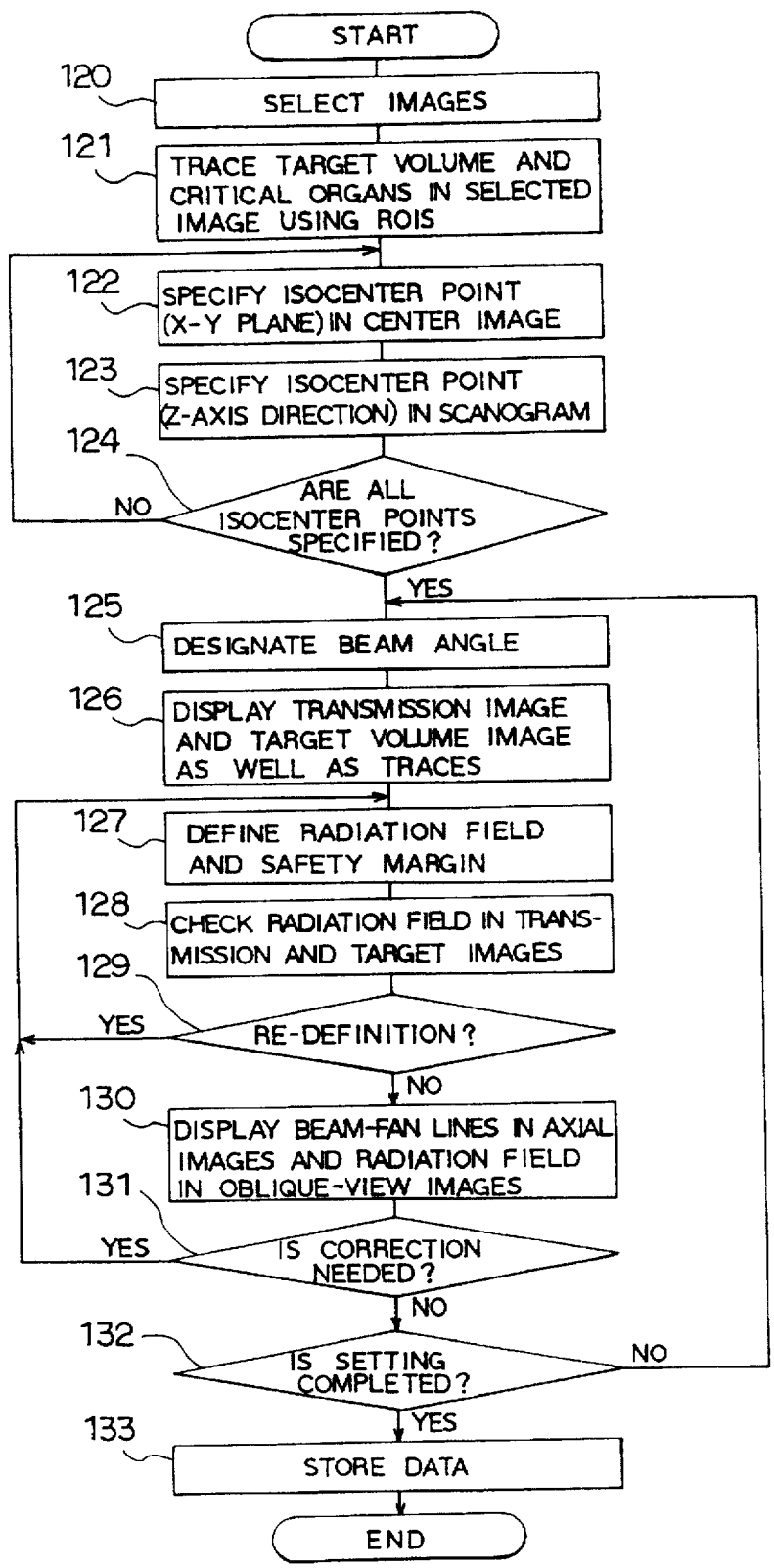
FIG. 21 is a flowchart describing a sequence of oblique planning.

FIG. 21 shows an outline procedure of oblique planning.

At step 120 in FIG. 21, the main control unit 40 selects images required for planning. A patient is identified using a patient directory, or axial images and a scanogram required for planning are selected or designated using an image directory.

In the oblique planning, a scanogram is used to specify an isocenter point along a body axis. If no scanogram is included in selected images, a plurality of axial images may be used to produce and display a top- or side-view image (a MultiPlanar Reconstruction (MPR) image rendering a thickness). The MPR image substitutes for a scanogram.

Figure 22:
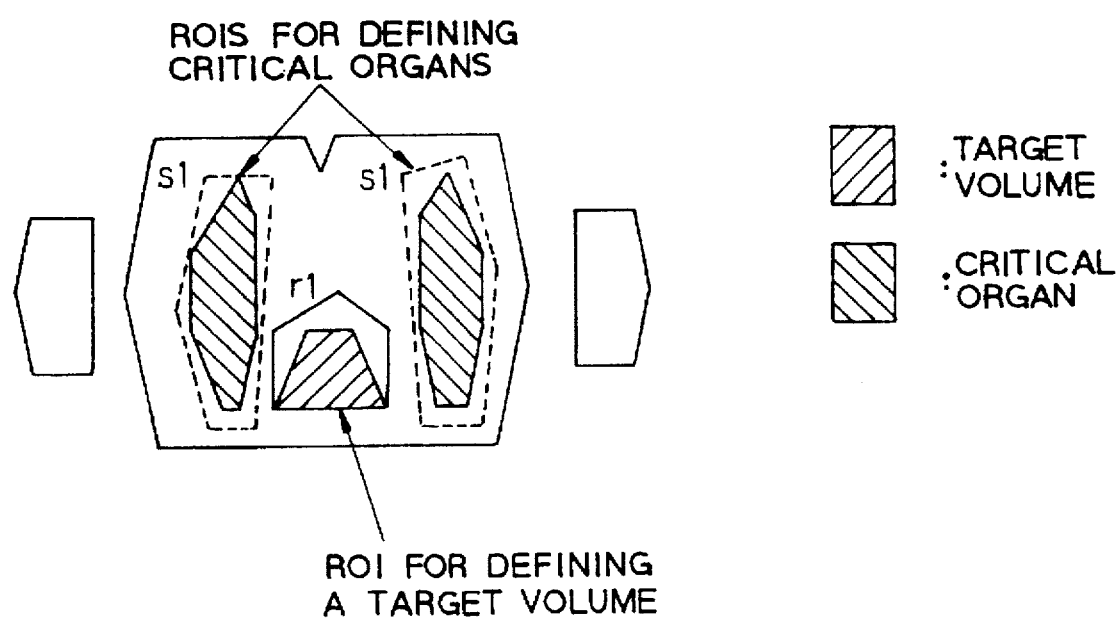
FIG. 22 is an explanatory diagram concerning oblique planning.

Control is then passed to step 121. A target volume and critical organs are traced with ROIs. As shown in FIG. 22, the positions and contours of a target volume and critical organs are traced in a selected image using ROIs manipulated with a mouse. The contours of ROIs include a polygon, a rectangle, a circle, and a free shape.

(1) Specifically, first, selected images are sorted in ascending (descending) order of couch positions. At this time, a scanogram is excluded.

(2) The first image is displayed.

(3) A target volume and critical organs are defined. ROIs are numbered and grouped according to the numbers (along the diameter of a body) at the time of determining an isocenter (See FIG. 22).

ROIs are numbered automatically in principle. If necessary, a user can modify the ROI numbers.

Figure 23:
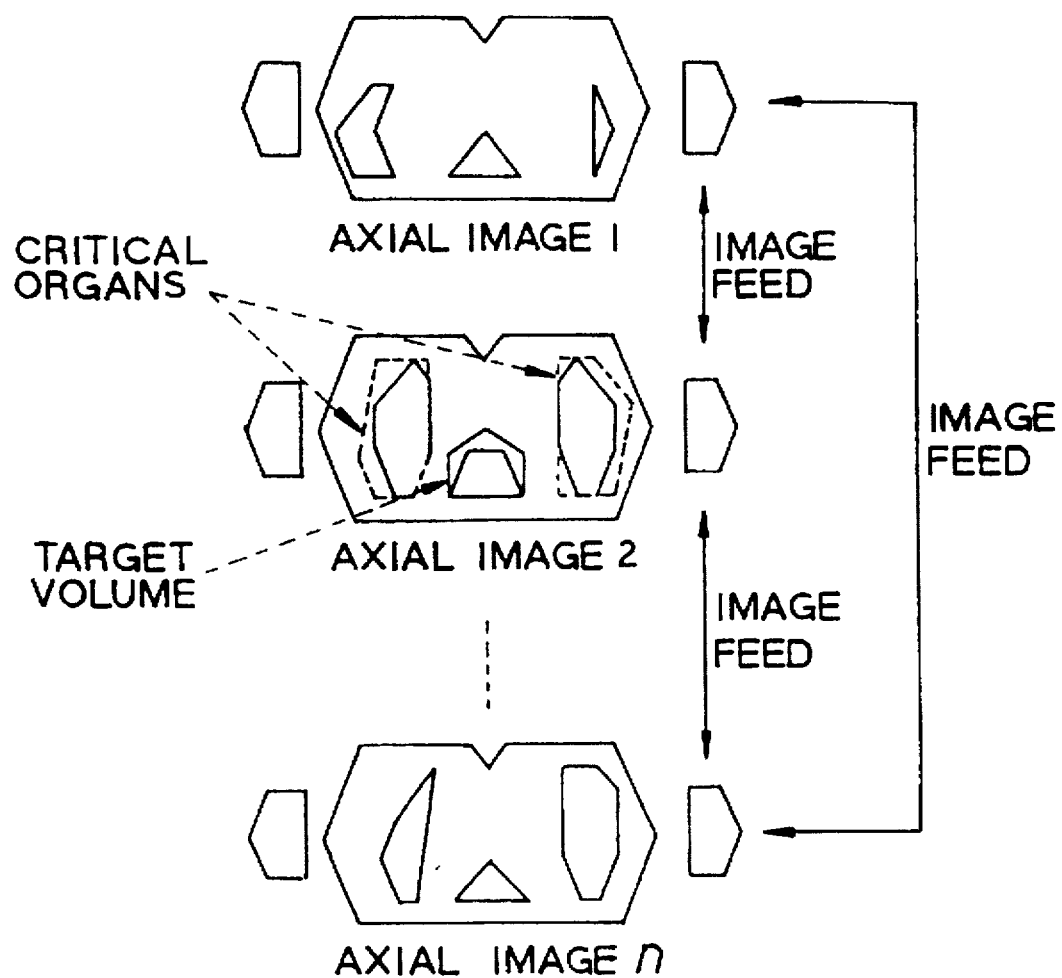
FIG. 23 is an explanatory diagram concerning oblique planning.
Figure 24:
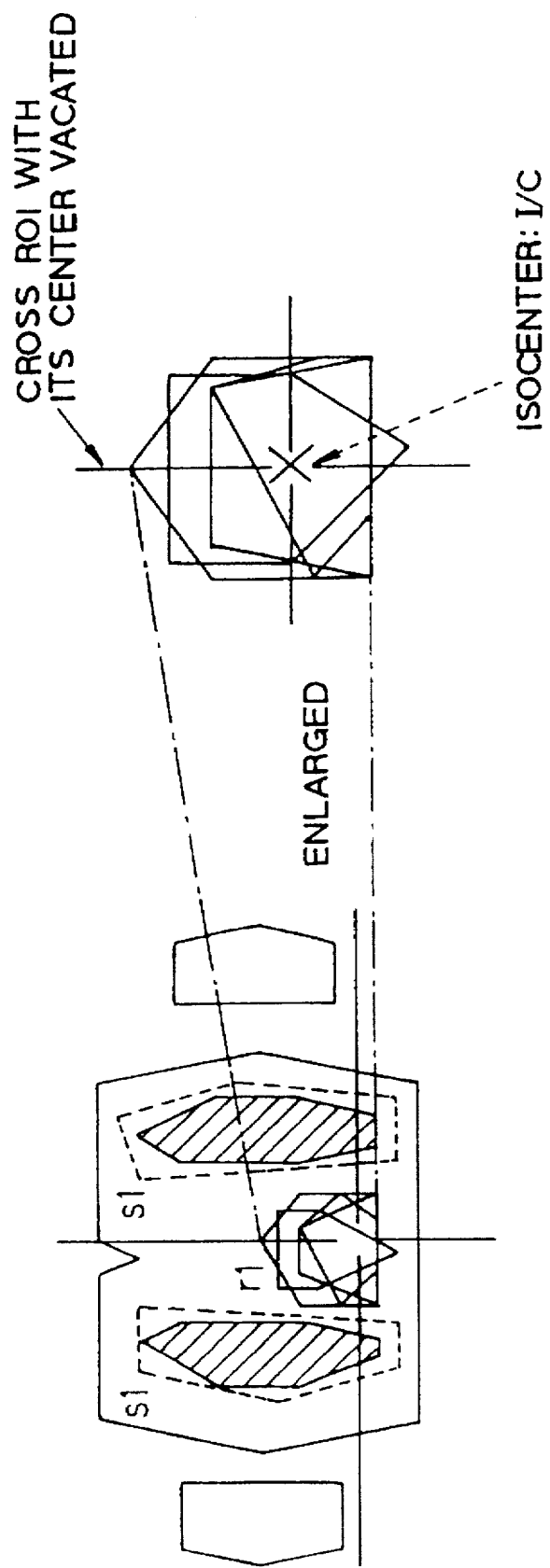
FIG. 24 is an explanatory diagram concerning oblique planning.
Figure 25:
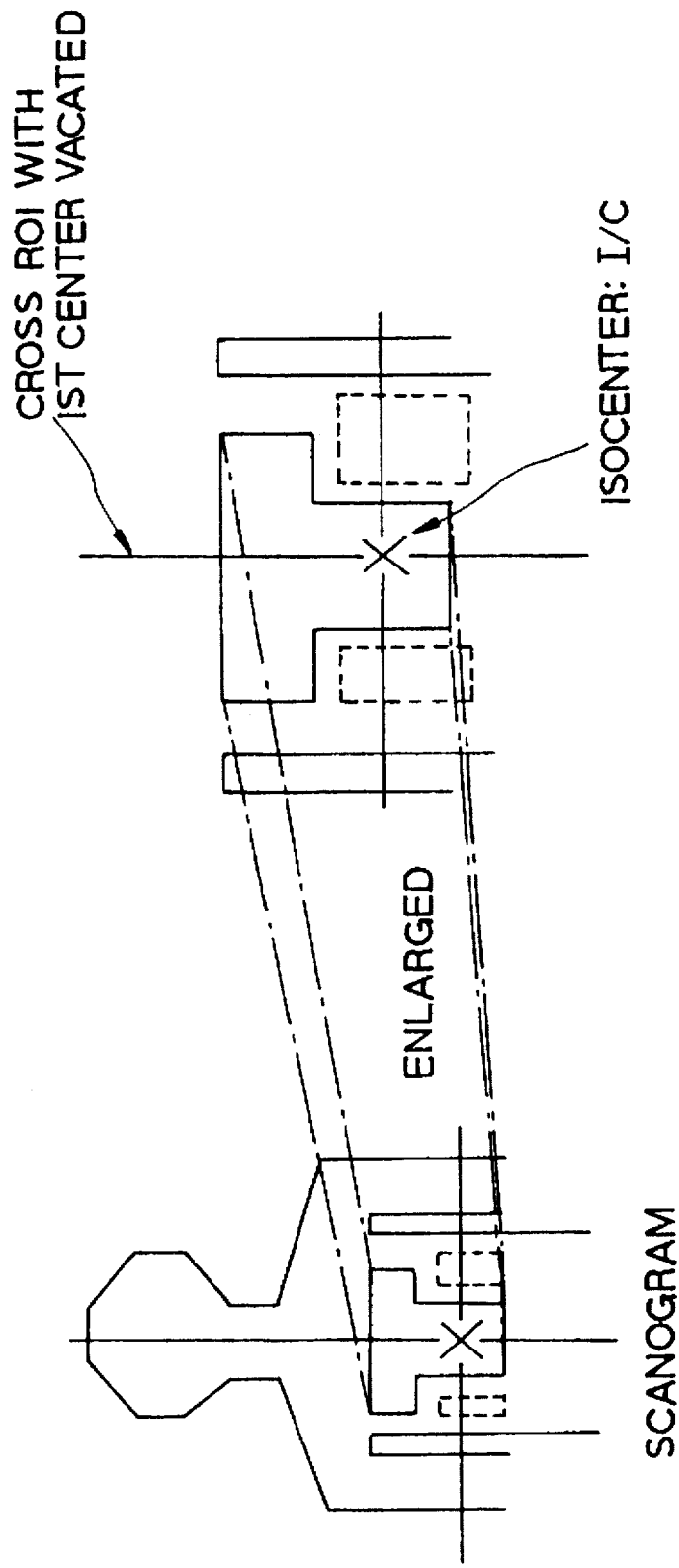
FIG. 25 is an explanatory diagram concerning oblique planning.

(4) Unless input of ROIs is in progress, image feed involving selected images can be executed (See FIG. 23).

(5) If necessary, multiframe display can be executed (a finalized target volume or critical organs are synthesized and displayed if any).

At step 122, an isocenter point on an x-y plane is specified. For specifying an isocenter point on an x-y (axial) plane, all ROIs whose numbers indicate a designated target volume and critical organs are superposed on user-designated images (by performing image feed). Based on the ROIs superposed, the user estimates the isocenter point (See FIG. 24). The isocenter point is stored together with the target volume number in the system.

At step 123, an isocenter point on an x-z plane is specified. For specifying an isocenter point on an x-z plane, a scanogram is displayed. The contours of a target volume and critical organs are superposed on the scanogram. Referencing the scanogram, the user sets a large cross ROI at the isocenter point (See FIG. 25). The isocenter point is stored together with the target volume number in the system.

At step 124, it is determined whether an isocenter i/C has been specified in all images. If there are images on which an isocenter I/C has not been specified, steps 123 and 124 are repeated. If an isocenter I/C is specified in all images, control is passed to step 125. A beam angle is then designated. In this embodiment, such irradiation techniques as single-port irradiation, opposed dual-port irradiation, perpendicular dual-port irradiation, and multi-port irradiation are supported.

Designation of a beam angle will be described for each irradiation technique.

(1) Single-port irradiation

Figure 26:
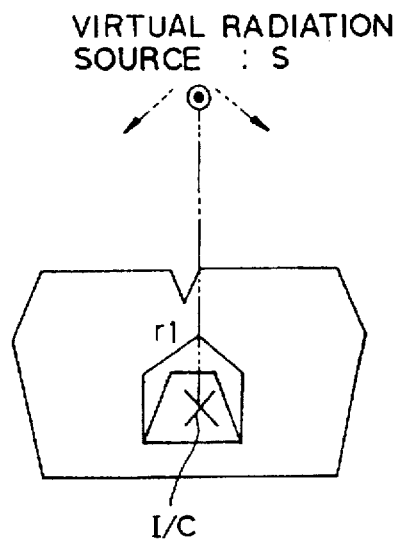
FIG. 26 is an explanatory diagram concerning oblique planning.

A beam angle of a virtual radiation source is determined with input values and an angle of a linear ROI with respect to an isocenter serving as a rotation axis. The operating procedure is as follows:

1) An image is displayed.
2) A target volume number is designated.
3) A virtual radiation source is placed at a position, for example as shown in FIG. 26.
4) A beam angle is determined with input values and an angle of a linear ROI with respect to an isocenter serving as a rotation axis.
5) The target volume number is stored in association with the beam angle of the virtual radiation source.
6) This operation can be performed on all target volumes. An already-designated beam angle can be corrected.

(2) Opposed dual-port irradiation

Figure 27:
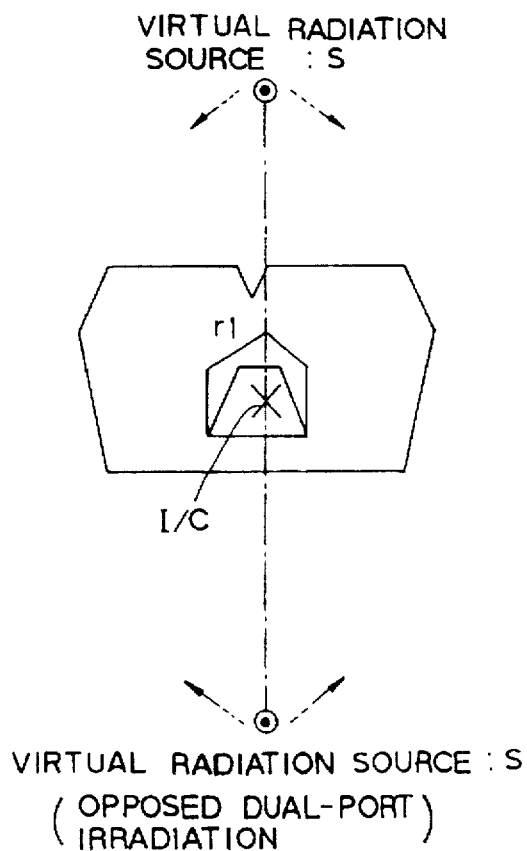
FIG. 27 is an explanatory diagram concerning oblique planning.

In principle, a beam angle of a virtual radiation source is designated according to the same procedure as that for single-port irradiation. The difference is, as shown in FIG. 27, that two virtual radiation sources are used for a single target volume and spaced apart by an angle of 180°. For storing data, one target volume number is associated with two beam angles. Similarly to scanoscopic planning, the same contour of a radiation field is defined for each of two ports in opposed dual-port irradiation.

(3) Perpendicular dual-port irradiation

Figure 28:
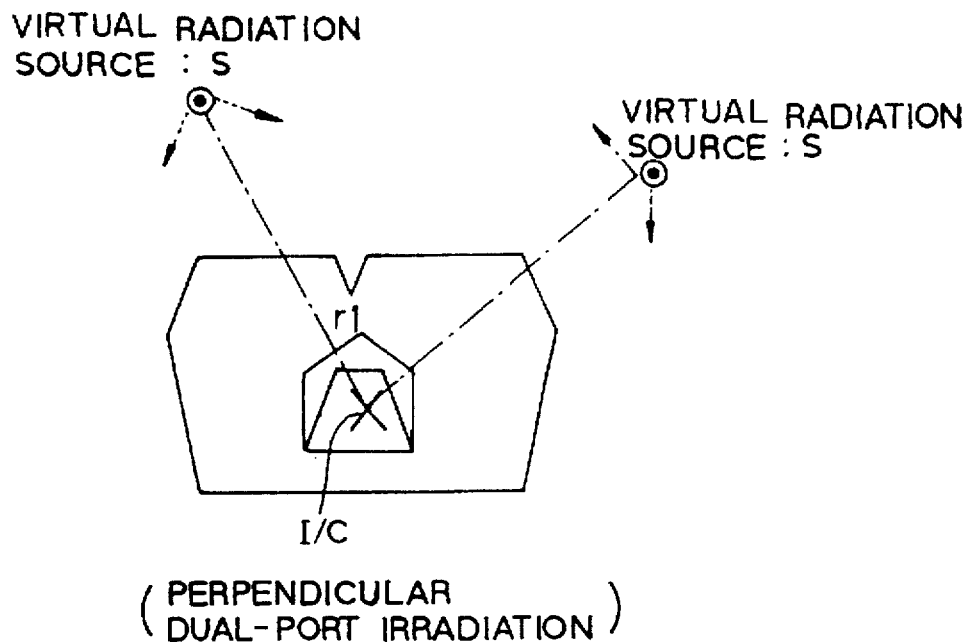
FIG. 28 is explanatory diagram concerning oblique planning.

In principle, a beam angle of a virtual radiation source is designated according to the same procedure as that for single-port irradiation. The difference is, as shown in FIG. 28, that two virtual radiation sources are used for a single target volume and spaced apart by an angle of 90°. For storing data, a target volume number is associated with two beam angles.

(4) Multi-port irradiation

Figure 29:
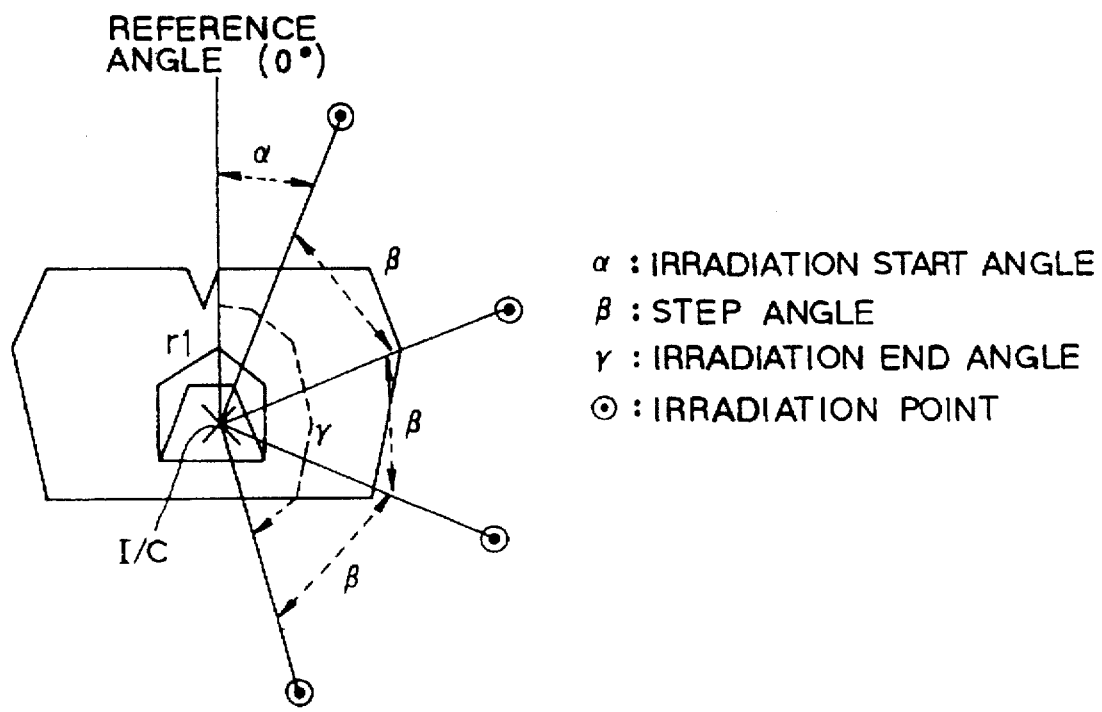
FIG. 29 is an explanatory diagram concerning oblique planning.
Figure 30B:
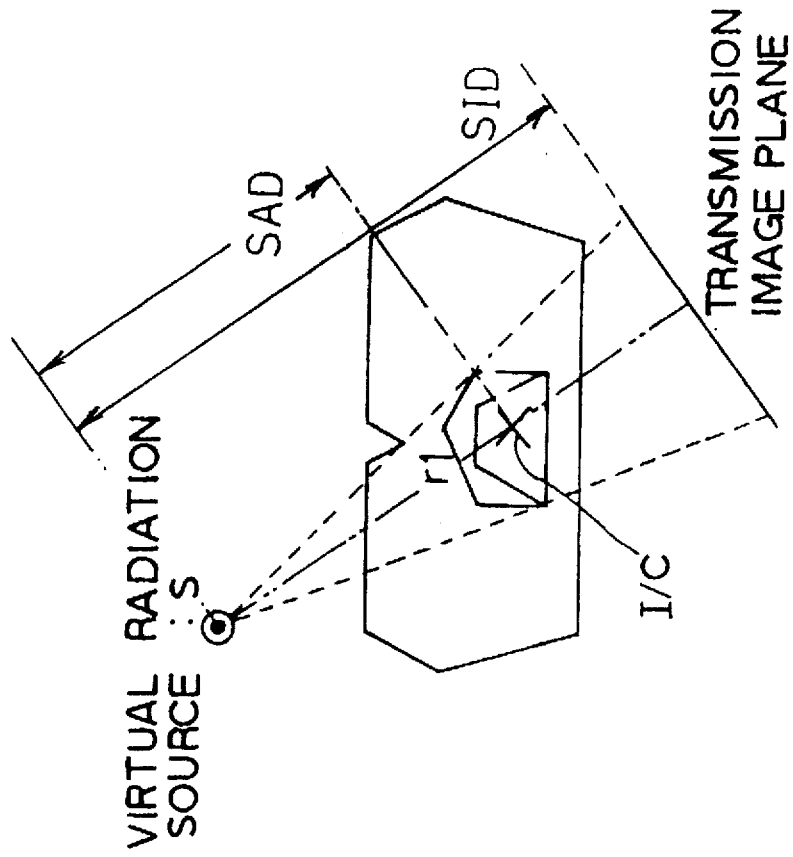
FIGS. 30A and 30B are explanatory diagrams concerning oblique planning.
Figure 30A:
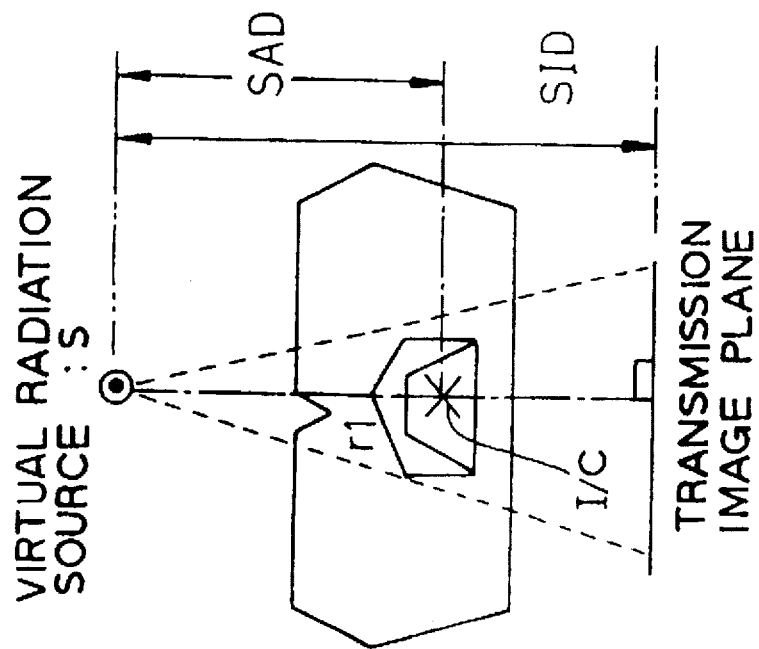

For multi-port irradiation, two procedures are available in designating a beam angle of a virtual radiation source. One procedure is the same as the one for single-port irradiation. In the other procedure, as shown in FIG. 29, an irradiation start angle, an irradiation end angle, and a step angle (at intervals of what angle irradiation is carried out) or the number of irradiation points are designated. As for the former, the procedure for single-port irradiation is carried out. The latter procedure is as follows:

1) A user displays any axial image.
2) A target volume number is entered.
3) An irradiation start angle α and an irradiation end angle γ are entered relative to a reference angle.
4) A step angle β or the number of irradiation points is entered.
5) A screen similar to the one shown in FIG. 29 appears.
6) A beam angle can be designated for each of the target volumes.

At step 126, data concerning a transmission image and a target volume image in an arbitrary direction is produced by performing MPR (multiplanar reconstruction) on three-dimensional tomographic image data, and then displayed.

A transmission image (See FIGS. 30A and 30B) is an image made by converting an image projected with parallel rays into an image projected with X-ray beams emanating from a virtual radiation source. The transmission image renders the same geometry as therapeutic irradiation. If only geometric distances of a radiotherapy apparatus such as a source-to-axis-of-radiation distance (hereinafter, SAD) and a source-to-image-receptor distance (hereinafter, SID) are available (these distances are set as environmental parameters), a transmission image can be produced.

When a user designates a position of a virtual radiation source, a transmission image relative to any radiation source is produced. Moreover, traces of a target volume and critical organs are synthesized with the transmission image.

Figures 31A, 31B:
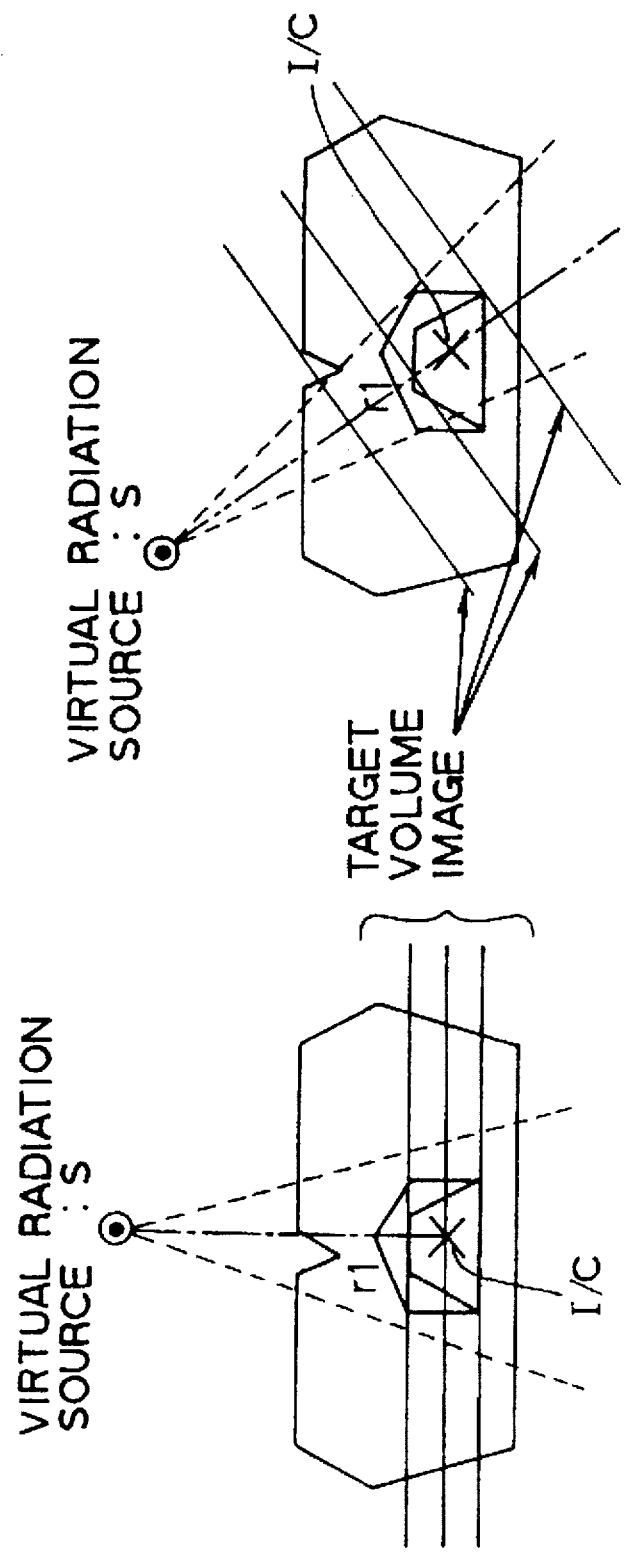
FIGS. 31A and 31B are explanatory diagrams concerning oblique planning.

On the other hand, a target volume image is an image projected on a beam's eyes (BE) plane parallel to a plane containing an isocenter (See FIGS. 31A and 31B). The target volume image provides accurate understanding of an irradiated state of a cross section parallel to the isocenter plane. Since the target volume image is an image projected on a plane parallel with the isocenter plane, similar to the transmission image, the direction of a cross section is determined depending on which position a virtual radiation source lies. A user uses a mouse or enters values (for example, a distance from a virtual radiation source) to specify a depth specified. Thus, an image of a target volume at the depth can be produced. In addition, traces of a target volume and critical organs are synthesized with the target volume image. The contour and size of a radiation field can be checked easily.

The transmission image or target volume image is produced by performing MPR on three-dimensional tomographic image data. When a virtual radiation source lies askew with respect to an x, y, or z axis, the transmission image or target volume image renders an oblique view.

Figure 32:
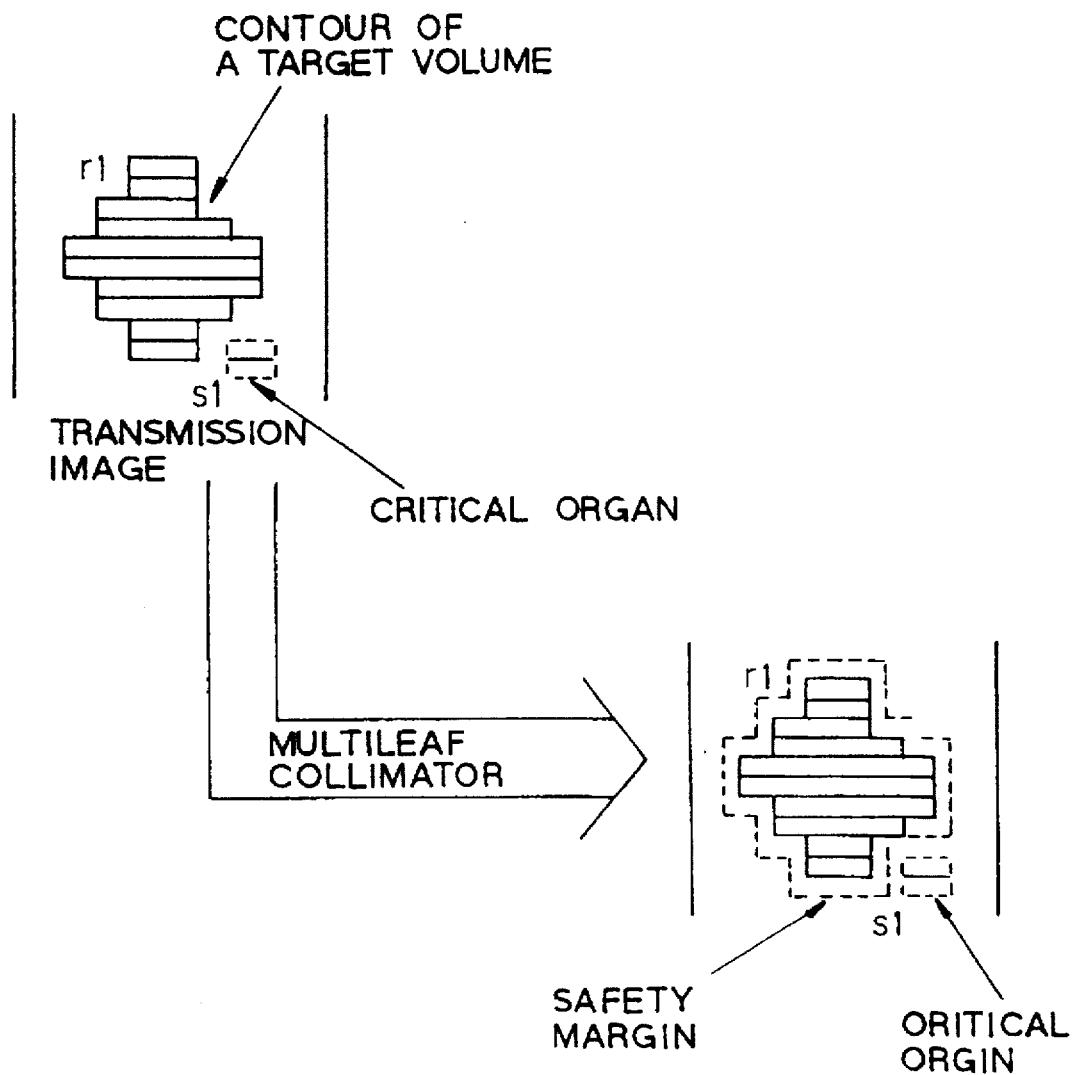
FIG. 32 is an explanatory diagram concerning oblique planning.

At step 127, a radiation field and a safety margin are defined. Since the radiotherapy apparatus 2 has a multileaf collimator 65, as shown in FIG. 32, a radiation field has the same contour as a target volume and a safety margin is similar to the contour of the radiation field. For irradiation through two or more ports, irradiation points (port numbers) are entered selectively so that the contour of a radiation field can be checked in a desired transmission image.

For defining the contour of a radiation field, the polygon ROI and rectangular ROI can be used.

Figure 33:
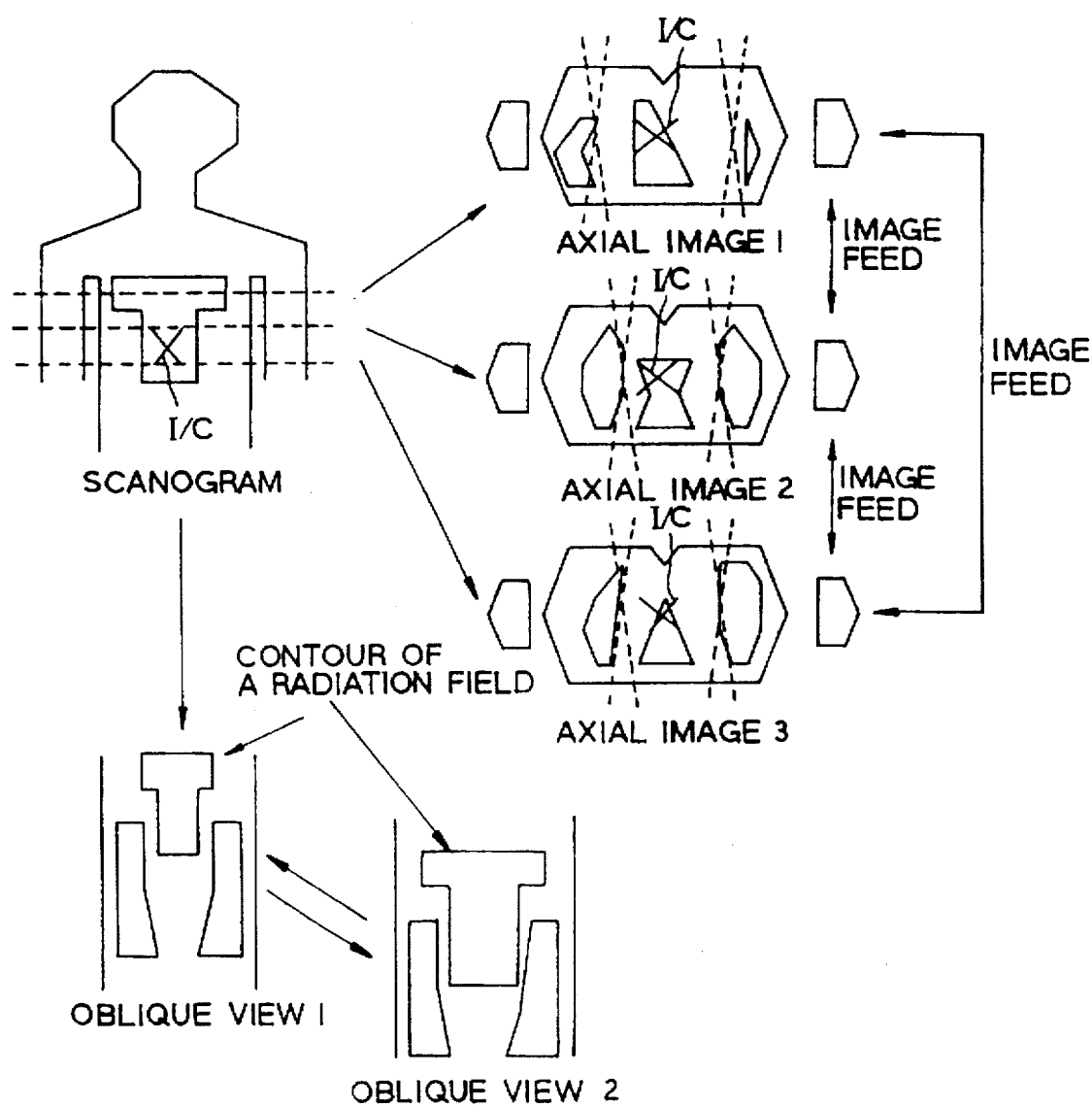
FIG. 33 is an explanatory diagram concerning oblique planning.

At step 128, the radiation field is identified in the transmission image and target volume image. At step 129, it is determined whether defining of another radiation field is needed. If it is needed, control is returned to step 127. If it is not needed, control is passed to step 130. Beam-fan lines are delineated in axial images, and the radiation field is delineated in the oblique-view images. The radiation field, beam angle, irradiation parameters, etc. are checked, as is shown in FIG. 33. The beam-fan lines or radiation field can be delineated in the axial images or oblique-view images by designating a target volume number and a virtual radiation source. One or more target volume numbers or virtual radiation sources can be designated.

At step 130, similar to step 212 in FIG. 10, when the positions of beam-fan lines delineated are changed using a mouse or the like, the contour of a radiation field delineated is corrected automatically in conformity with the change in position (See steps $130_1$ to $130_4$ in FIG. 34).

When any step of the aforesaid procedure should be re-executed, the result of determination made at step 131 (correction is needed ?) is affirmative. Thus, the procedure is restarted from step 127.

If the result of determination made at step 132 to see if setting is completed is affirmative, control is passed to step 133. Data of set parameters is stored in a memory.

As mentioned above, scanoscopic planning or oblique planning is performed to set the position of an isocenter (three-dimensional position data) and the contour of a radiation field on a body surface (two-dimensional contour data).

Control is then returned to the sequence of steps 108 to 110 in FIG. 9. The laser positioning projectors 27a to 27c are used to carry out marking. During the marking, the positions of the positioning projectors 27a to 27c and the position of the couchtop 12a of the patient couch 12 are controlled so that the cross marks M1 to M3 will automatically pinpoint the isocenter specified. Positioning control for marking may not necessarily be carried out after therapy planning but may be carried out immediately after the position of an isocenter I/C is determined. For example, for scanoscopic planning, positioning control may be executed after step 214. For oblique planning, it may be executed between steps 124 and 125 or after step 133.

The main control unit 40 determines, based on a command entered at the input unit 48 at step 108, whether marking should be executed. If the result of determination is affirmative (marking should be executed), the right and left positioning projectors 27a and 27c are returned to a marking angle (0°) at step 108a. Control is then passed to step 109. At step 109, the position data concerning the isocenter I/C is supplied to the positioning projector controller 49 and patient couch control unit 41. The position in z-axis (body axis) direction of the couchtop 12a is then controlled automatically, so that the positions on mark projection plane of the positioning projectors 27a to 27c will become consistent with the z coordinate of the position data concerning the isocenter I/C. The positions in y-axis direction of the right and left positioning projectors 27a and 27c are then controlled automatically, so that the positions of the marks M1 and M3 will become consistent with the y coordinate of the position data concerning the isocenter I/C. Likewise, the position in z-axis direction of the center positioning projector 27b is controlled automatically, so that the position of the mark M2 will become consistent with the x coordinate of the position data concerning the isocenter I/C.

Since the three marks M1 to M3 are projected on the body surface of a subject P, an operator traces the marks M1 to M3 with a Magic Marker or the like. Thus, the subject is ready to undergo radiotherapy to be undertaken days later.

A plurality of isocenters I/C may be specified for a plurality of lesions. It is therefore determined at step 110 if positioning control has been executed for all isocenters. If there is an isocenter for which positioning control has not been executed, step 109 is repeated. At step 111, the positioning projectors 27a to 27c are reset to the home positions in different x, y and z directions.

Next, collimator control for radiotherapy performed by the radiotherapy apparatus 2 will be described in conjunction with FIG. 35. In this embodiment, the CT system 1 for use in therapy planning directly controls the opening of the collimator 55 in the radiotherapy apparatus 2.

Figure 35:
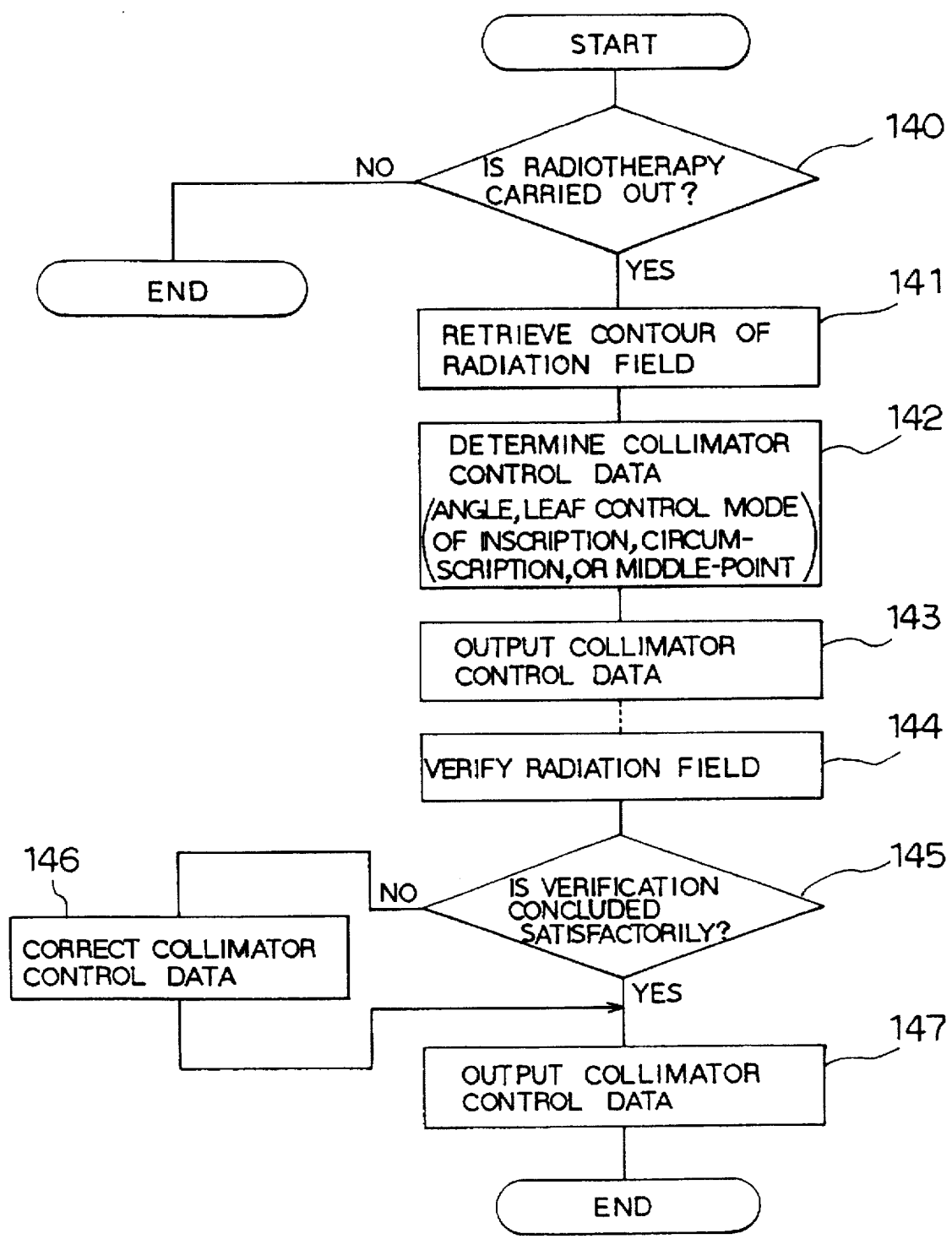
FIG. 35 is a flowchart describing collimator opening control for treatment.

At step 140 in FIG. 35, the main control unit 40 in the CT system 1 determines, based on operational information entered at the input unit 48, whether radiotherapy should be carried out. If radiotherapy is carried out (the result of determination is affirmative), steps 141 to 143 are executed sequentially.

Figures 36A, 36B, 36C:
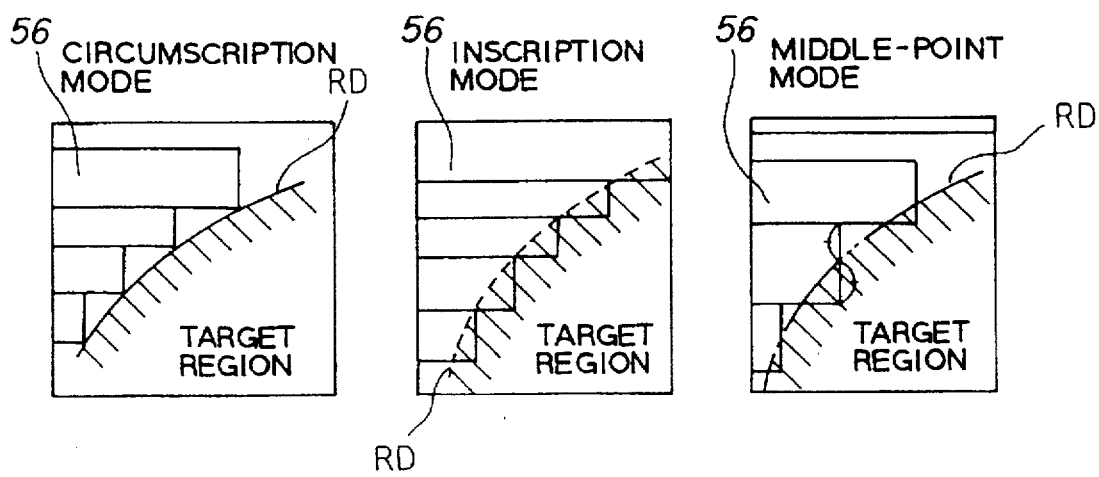
FIGS. 36A to 36C are explanatory diagrams concerning control modes for collimator opening control.

At step 141, the contour data concerning an already-defined radiation field is retrieved from the image memory 46. At step 142, an angle of the whole collimator 55 and a leaf control mode are determined. The angle is set to an appropriate value in conformity with the inclination in, for example, longitudinal direction of the radiation field. The system of this embodiment offers three leaf control modes; inscription mode, circumscription mode, and middle-point mode. In the circumscription mode, the edges of the leaves 56 are, as shown in FIG. 36A, circumscribed the contour of a radiation field (target volume) RD. In the inscription mode, the edges of the leaves 56 are inscribed as shown in FIG. 36B. In the middle-point mode that is an intermediate mode of the circumscription and inscription modes, the contour of a radiation field intersects the short sides of the leaves 56; that is, the edges of the leaves 56, as shown in FIG. 36C. Mode selection is dependent on whether critical organs are adjoining or what is an error in irradiation.

When data required for controlling the collimator 55 is determined, control is passed to step 143. The data is supplied to the verification recorder 4.

The verification recorder 4 is designed mainly to finely adjust a radiation field according to the passage of time since the radiation field may vary until radiotherapy is actually carried out. For example, the fluoroscopic facility included in the radiotherapy apparatus 2 is used to superpose a previously-defined radiation field on a fluoroscopic image produced immediately before radiotherapy. Thus, an operator is asked to verify the radiation field.

As a result of verification, if it is found that the lesion has shrunk, the result of determination made at step 145 to see if verification is concluded satisfactorily is negative. In this case, the positions of the leaves 56 are finely adjusted at step 146. The verification recorder 4 then prepares new corrected data.

When collimator control data is finalized, control is passed to step 147. The data is then transmitted to the main control unit 60 in the radiotherapy apparatus 2. When receiving the data, the main control unit 60 transfers the data to the collimator control unit 64. The collimator control unit 64 independently actuates the individual driving mechanisms 57 coupled with the leaves 56 according to the contents of the control data.

The size and contour of an opening defined with two groups of leaves 56A and 56B are substantially consistent with those of the radiation field RD on the body surface. The range of X-ray irradiation to be performed later on a deep-seated lesion will be substantially consistent with the opening. The radiotherapy apparatus 2 carries out radiotherapy according to the planned therapeutic procedure. When a plurality of regions to be treated (pluralities of isocenters and radiation fields) are designated, the aforesaid determination of collimator control data, verification, and automatic collimator control are executed for each region. Radiotherapy is then carried out.

The aforesaid determination of collimator control data (step 142) may be assigned to the main control unit 60 in the radiotherapy apparatus 2.

As mentioned above, in the radiotherapy system of this embodiment, the radiotherapy planning CT system, into which almost all of the capabilities of an image acquisition scanner, a radiotherapy planner, and a simulator are integrated, substitutes for a plurality of apparatuses such as an X-ray CT scanner, a radiotherapy planner, and an X-ray CT simulator. Unlike a conventional radiotherapy system, the system of this embodiment enjoys a compact and simple hardware configuration. This results in marked space saving. Transport of apparatuses due to installation or a layout change of a room can be achieved effortlessly.

In the aforesaid embodiment, the positions of the cross marks projected by the three positioning projectors 27a to 27c in the simulator capability are automatically controlled according to the position of an isocenter determined during therapy planning. The operational procedure ending with a process of tracing the isocenter marks on a body surface can therefore be simplified. This results in quick and easy marking.

Unlike those in a conventional system, the positioning projectors 27a to 27c are mounted directly in the gantry 11. The concern about a shift of a reference position resulting from a long-term external vibration propagated to a building can be eliminated. When the gantry 11 must be displaced in order to change the layout of a radiotherapy system, the conventional time-consuming work of aligning the positioning projectors mounted on the wall and ceiling and the gantry becomes unnecessary.

During radiotherapy, the contour data concerning a radiation field which is produced during therapy planning is fed automatically to the radiotherapy apparatus 2 over a transmission line. Thus, the opening of a multileaf collimator can be controlled automatically. Compared with a system in which opening data must be manually input to a radiotherapy apparatus and the opening of a collimator must be adjusted manually, the system of this embodiment realizes a drastic reduction in time required for setting the opening of the collimator. Consequently, the overall operability improves.

The system of this embodiment offers two therapy planning techniques; scanoscopic planning and oblique planning. A therapy planning technique suitable for a case can be selected. The system proves very useful.

Scanoscopic planning makes it possible to designate either single-port irradiation or opposed dual-port irradiation. A radiation field and an isocenter are set in a scanogram. The radiation field and beam-fan lines can be delineated in the scanogram and axial images respectively. This delineation enables easy and intuitive assessment of the validity of an irradiation plan. By contrast, oblique planning makes it possible to designate single-port irradiation, opposed dual-port irradiation, perpendicular dual-port irradiation, rotation irradiation, or conformation irradiation. A target volume such as a tumor can be accurately specified in a plurality of axial images. Transmission and target volume images projected on planes opposed to a radiation source at arbitrary irradiation angles or in arbitrary irradiation directions are used to make a therapy plan. The contour of the radiation field and the beam-fan lines can be identified quickly in any target volume image and axial image.

In the oblique planning, the transmission image rendering a geometric equivalent to that employed in therapy is used in combination with the target volume image. Compared with the exclusive use of the target image, the combined use makes it possible to make a higher-precision plan for treatment of a target volume according to an irradiation angle permitted by a radiotherapy apparatus.

Since a fine adjustment facility is included, when the positions of beam-fan lines are changed in the course of either scanoscopic planning or oblique planning, the contour of a radiation field is corrected. Therefore planning procedure need not be restarted from the beginning in order to re-set the contour of a radiation field. This will be very convenient.

While oblique planning is under way in the CT system 1, oblique angle information including a set irradiation angle of radiation is transferred from the CT system 1 to the radiotherapy apparatus 2. For treatment, the main control unit 60 and patient couch control unit 62 in the radiotherapy apparatus 2 may be designed to automatically control a slewing angle of the patient couch 50 according to the oblique angle information. Thereby, radiation can be irradiated obliquely to a patient, relative to the body axis. The irradiation direction that is the slewing angle can be determined depending on the position and contour of a region to be treated. This will prove very effective in avoiding exposure of a certain region.

In the aforesaid embodiment, the radiotherapy planning CT system offers both oblique planning and simpler scanoscopic planning. In some cases, oblique planning alone may be implemented in the system.

The radiotherapy apparatus in the aforesaid embodiment adopts X rays for a radiation source. Alternatively, the radiotherapy apparatus may use any other radiation source for prompt neutrons, gamma rays or the like.

Radiotherapy apparatuses in the aforesaid embodiment and its variants are configured so that opening control data concerning a multileaf collimator or slewing angle control data concerning a patient couch is received online from a CT system for actual control. Alternatively, control data produced by a therapy planner connected offline or transferred from an external discrete therapy planner may be used.

As described previously, according to the present invention, a radiotherapy system includes a radiotherapy planning CT system into which the capabilities of an X-ray CT scanner, a radiotherapy planner, and a simulator, which used to be provided as stand-alone apparatuses or configured as at least a plurality of apparatuses or systems, are integrated and of which patient couch and gantry can be used for diverse purposes. Compared with a conventional radiotherapy system, the radiotherapy system in accordance with the present invention has a hardware system designed more simply and compactly. This results in space saving and easy transport of apparatuses.

In the radiotherapy system according to the present invention, contour data concerning a radiation field which is produced by a radiotherapy planning CT system is fed to a radiotherapy apparatus. The opening of a collimator in the radiotherapy apparatus is automatically controlled according to desired mode. This contributes to a reduction in time required for treatment and improvement of operability.

In the radiotherapy planning CT system according to the present invention, three positioning projectors for marking an isocenter are mounted directly in a gantry. Unlike a conventional structure of mounting projectors on the wall and ceiling, this structure eliminates concern about the misalignment of the positioning projectors and the gantry resulting from external vibrations. Even when the gantry is displaced, realignment is unnecessary. Thus, excellent maintainability ensues.

In the radiotherapy planning CT system according to the present invention, the positions of three positioning projectors and a couchtop are automatically controlled according to determined position data concerning an isocenter in the course of isocenter marking. Time required until marks are traced to draw markers is reduced drastically. Operational efficiency therefore improves. This greatly contributes to a reduction in total treatment time.

Furthermore, the radiotherapy planning CT system in accordance with the present invention makes it possible to select a first planning means (scanoscopic planning) or a second planning means (oblique planning) according to a therapeutic necessity and to duly achieve therapy planning. This is quite useful. Especially, the second planning means realizes more meticulous radiotherapy planning for a target volume because of the employment of transmission and target volume images projected on oblique planes dependent on irradiation angles. Consequently, high-precision treatment can be undertaken on a lesion distinctly distinguished from normal tissues.

In the radiotherapy system according to the present invention, fine adjustment of a radiation field being planned is achieved by moving beam-fan lines delineated. This results in excellent operability and quicker therapy planning.

(The Second Embodiment)

The radiotherapy system including a radiotherapy planner in accordance with the second embodiment of the present invention will be described in conjunction with FIGS. 37 to 45, which is identical in construction to that of the first embodiment.

The operation of the second embodiment will be described in conjunction with FIGS. 37 to 45.

Figure 37:
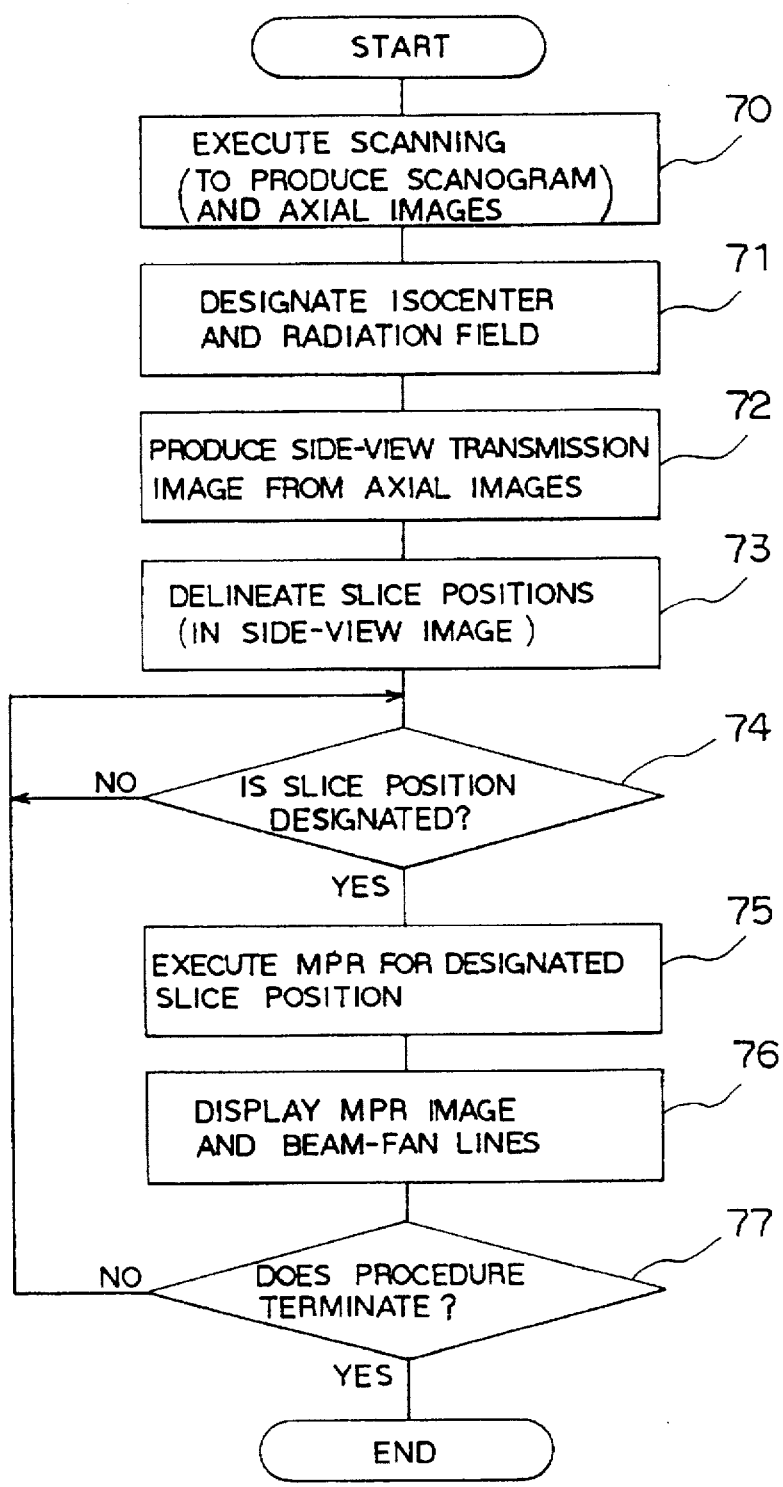
FIG. 37 is a flowchart describing therapy planning executed by a main control unit in the second embodiment.
Figure 38:
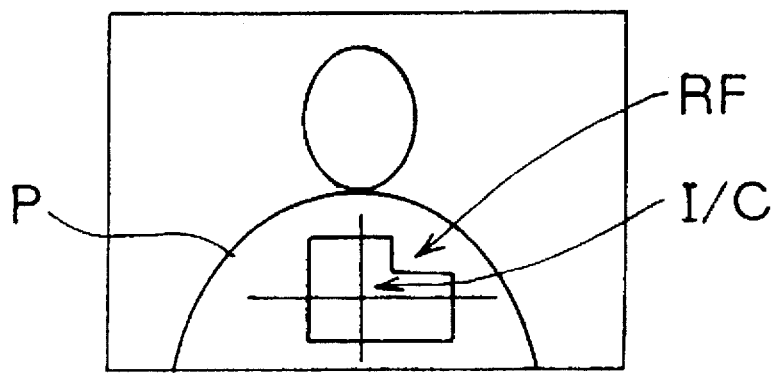
FIG. 38 shows the relationships among a top-view scanogram, an isocenter, and a radiation field.

The main control unit 40 in the CT system 1 carries out therapy planning according to the procedure shown in FIG. 37. Specifically, at step 70, scanning is requested with command information entered at the input unit 48. This results in a top-view scanogram (transmission image rendering a frontal view of a subject) and a plurality of axial images produced by X-ray CT. The plurality of axial images are used to produce voxel data. For example, helical scanning is preferred to produce the plurality of axial images.

At step 71, the top-view scanogram is displayed on the display unit 47. A target volume is outlined in the displayed image by tracing a lesion with a ROI. In line with the contour of the target volume, a radiation field RF is defined and an isocenter I/C is specified (See FIG. 38).

Figure 39:
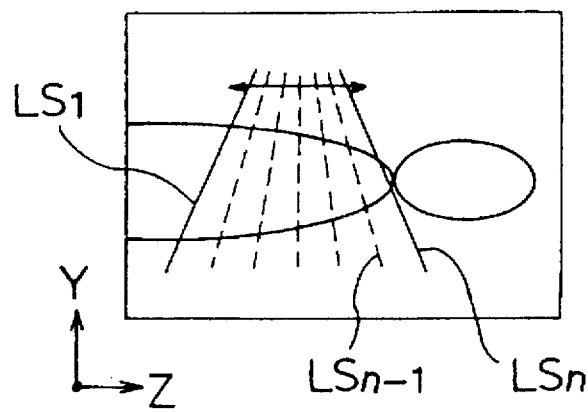
FIG. 39 shows an example of the relationships between a side-view scanogram and slice positions.

Control is then passed to step 72. Data concerning the plurality of axial images that correspond to voxel data are used to reconstruct a side-view transmission image of the subject P (a transmission image rendering a lateral region of the subject). At step 73, the side-view transmission image is displayed with lines LS1, LS2, to LSn for use in specifying the positions of slices convoluted thereto as shown in FIG. 39. The lines for specifying the positions of slices LS1, LS2, to LSn are computed using such data as the size of the radiation field RF and the position of the radiation source and provided as lines linking equidistant points along a body axis or z axis with the radiation source.

Control is then passed to step 74. It is determined whether any slice position in the screen is designated using a pointing device (for example, a mouse, a trackball, a light pen, or a cursor key) serving as the input unit 48. If the result of determination is affirmative (any slice position is designated), multiplanar reconstruction (hereinafter, MPR) is executed for the slice position designated at step 75.

Figure 40:
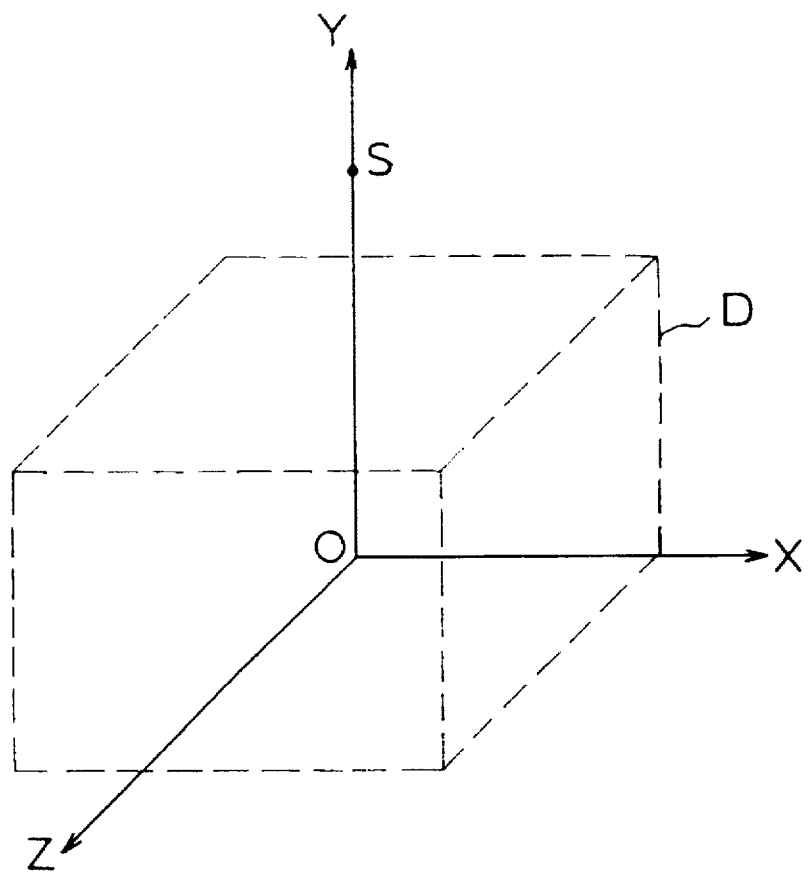
FIG. 40 is an explanatory diagram concerning production of an MPR image.
Figure 41:
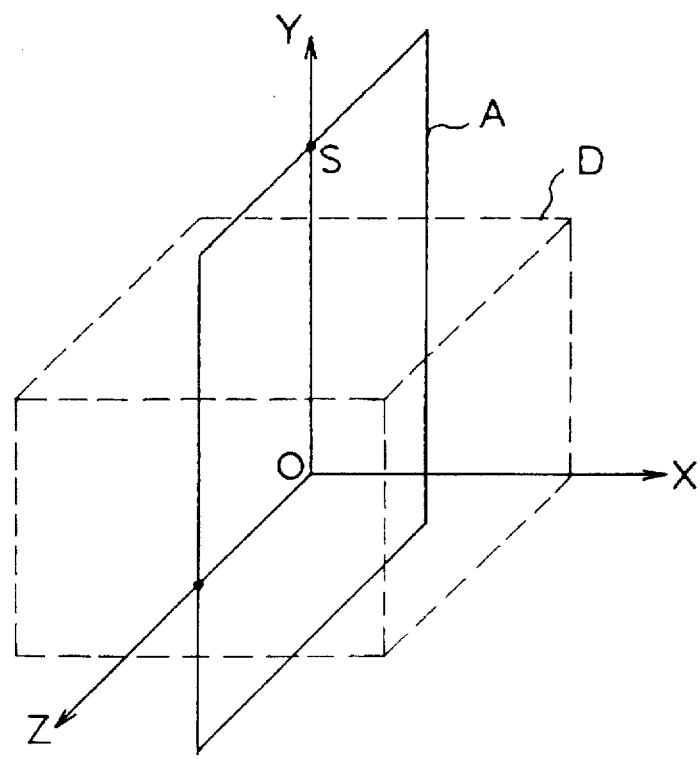
FIG. 41 is an explanatory diagram concerning production of an MPR image.
Figure 42:
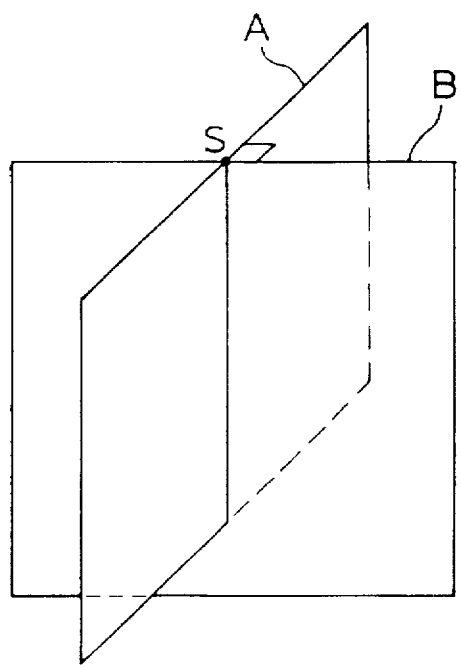
FIG. 42 is an explanatory diagram concerning production of an MPR image.
Figure 43:
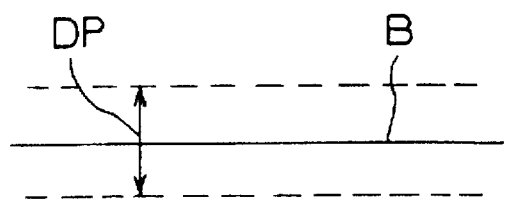
FIG. 43 is an explanatory diagram concerning production of an MPR image.

FIGS. 40 to 43 show a MPR sequence. Specifically, first, the radiation source S is, as shown in FIG. 40, specified on a y axis of a three-dimensional space represented by voxel data D produced from a plurality of axial images. A plane A containing the radiation source S and an origin of the coordinate system is defined. The plane A can be defined arbitrarily according to a desired viewing direction. For example, as shown in FIG. 41, the plane A is a y-z plane. A plane B containing the radiation source S and being orthogonal to the plane A is defined. The plane B can be angled freely according to a designated slice position using a trackball or the like. A desired thickness DP with the defined plane B as a core is determined, and pixel values residing within the thickness DP in the voxel data are added up and used as projection data concerning the plane B (See FIG. 43).

Figure 44:
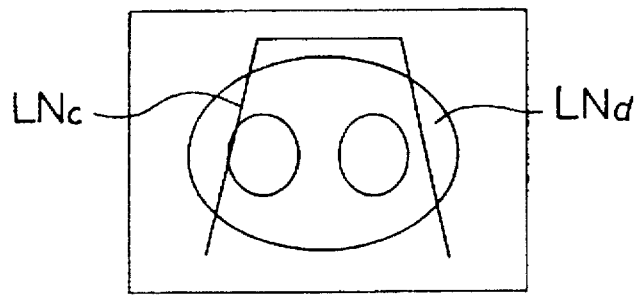
FIG. 44 shows an MPR image and beam-fan lines in the second embodiment.

When MPR is thus completed, control is passed to step 76. The MPR image and beam-fan lines convoluted to the MPR image are displayed. As shown in FIG. 44, beam-fan lines LNc and LNd are superposed on a projection image rendering the plane B. This screen is variable depending on a designated slice position under the constraints imposed by the positions of the radiation source S and plane A. Unless the procedure terminates at step 77, another MPR image and beam-fan lines are displayed according to a newly designated slice position. For reference, the screen containing the side-view scanogram in FIG. 39 corresponds to a screen containing an image rendering the plane A and lines of intersections between the planes A an B.

Figure 45:
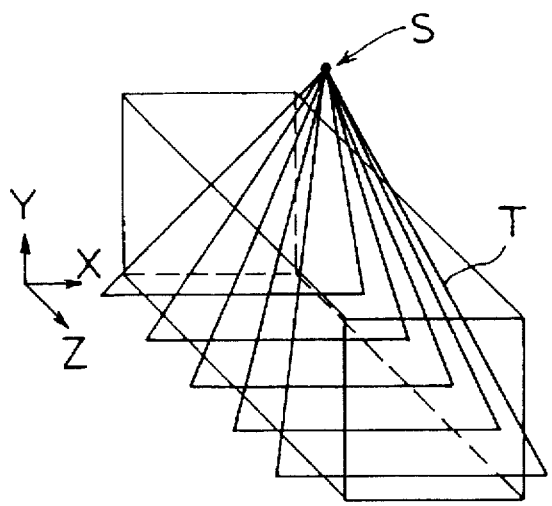
FIG. 45 is an explanatory diagram concerning cross sections along radiation paths in the second embodiment.

According to this embodiment, as shown in FIG. 45, MPR images rendering oblique planes lying along radiation paths T originating from the radiation source S and lining up along the body axis or z axis can be displayed together with beam-fan lines vertically running through each of the MPR images. This is very helpful in identifying a radiation path, thus leading to quick therapy planning with higher precision.

In this embodiment, a side-view scanogram may be produced and used from the beginning.

(The Third Embodiment)

Next, the third embodiment will be described. A radiotherapy apparatus of the second embodiment is responsible for display and correction of a therapy plan. The hardware configuration is identical to that of the first embodiment shown in FIGS. 2 to 8. (The fourth to ninth embodiments described below will also be identical in hardware configuration to the first embodiment.)

The main control unit 40 in the CT system 1 in the second embodiment commands that a therapy planning procedure shown in FIG. 46 be executed. First, (side- and top-view) scanograms rendering a region of the subject P containing a lesion as well as a plurality of CT (axial) images are produced at step 80. Practical therapy planning of step 81 and thereafter is then commenced.

Figure 47:
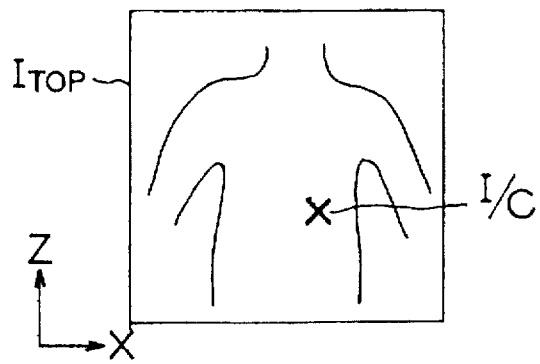
FIG. 47 is an explanatory diagram concerning specification of an isocenter.
Figure 48:
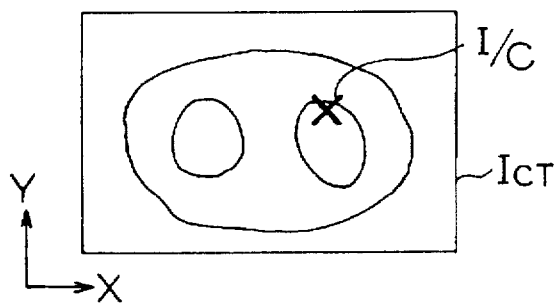
FIG. 48 is an explanatory diagram concerning specification of an isocenter.
Figure 49:
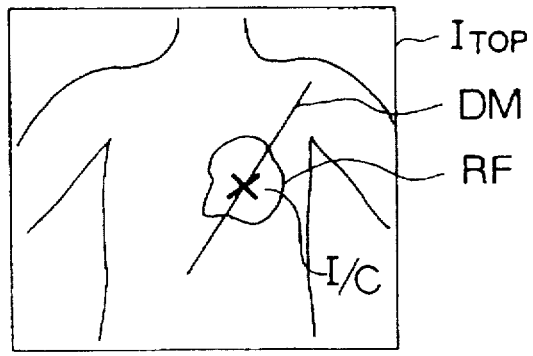
FIG. 49 is an explanatory diagram concerning designation of the contour of a radiation field.

At step 81, a z-coordinate of an isocenter I/C is designated in the top-view scanogram $I_{TOP}$, and x and y coordinates of the isocenter I/C are designated in a CT image $I_{CT}$ (See FIGS. 47 and 48). At step 82, a radiation field RF is outlined and displayed in the top-view scanogram $I_{TOP}$. At this time, since the multileaf collimator 55 is adopted in this embodiment, the radiation field RF can be outlined to have any contour. The contour data is converted into data concerning an opening defined by leaves 56. A rotation direction DM of the whole collimator 55 is computed (See FIG. 49). The rotation direction is determined in consideration of which direction in the x-z plane the collimator 55 should be rotated in order to form an opening having a minimal error from the contour of the radiation field RF. When lead blocks are used instead of the multileaf collimator, a polygon resembling the contour of a radiation field is defined using the lead blocks.

At step 83, a slice position $P_{SL}$ (See FIG. 52) is determined in the top-view scanogram $I_{TOP}$. An associated CT image $I_{CT}$ is selected.

Figure 50:
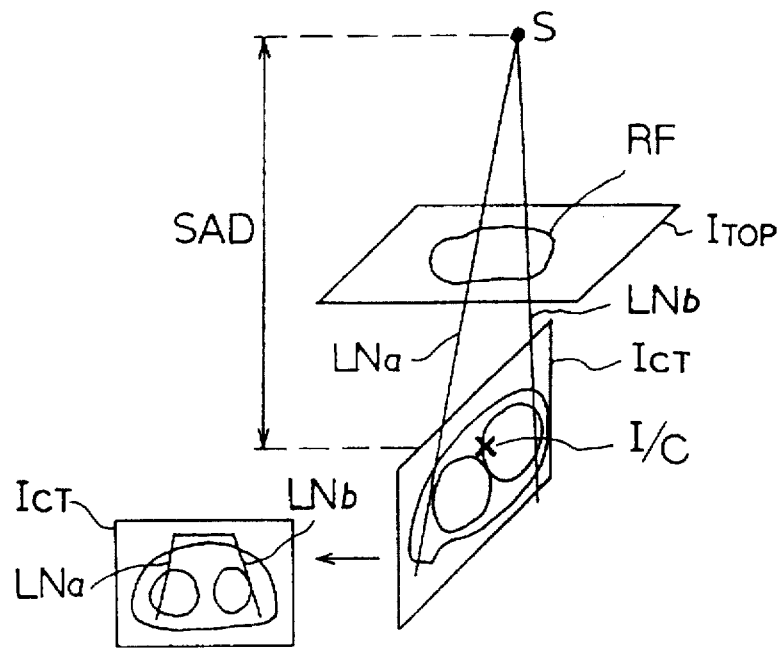
FIG. 50 is an explanatory diagram concerning defining of beam-fan lines in a CT image.
Figure 51:
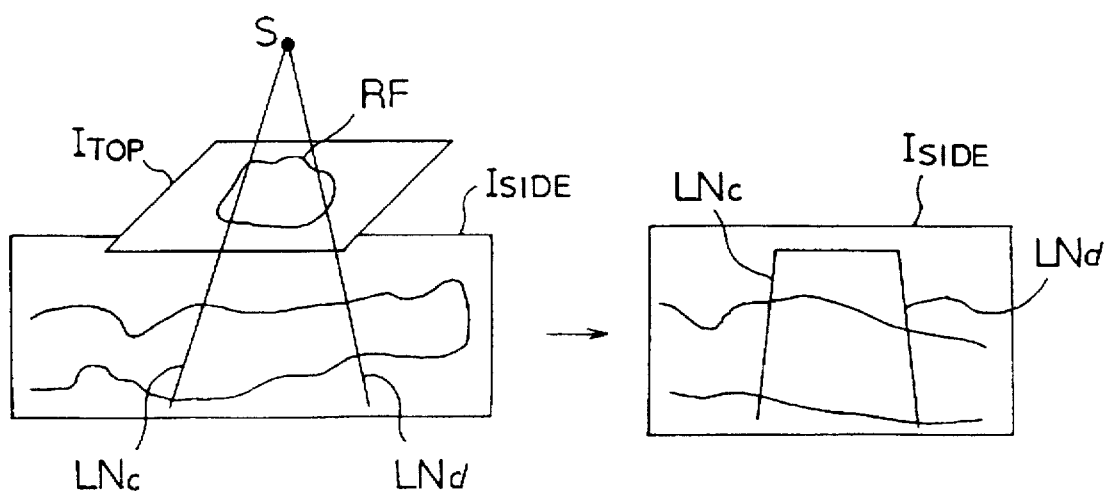
FIG. 51 is an explanatory diagram concerning defining of beam-fan lines in a side-view scanogram.

At step 84, beam-fan lines are superimposed and delineated in the selected and displayed CT image $I_{CT}$. Specifically, as shown in FIG. 50, a width in x-axis direction of the radiation field RF contained in a slice specified with a slice position (z coordinate) and a distance SAD between the radiation source S and isocenter I/C are used to calculate a range exposed to radiation (or beam-fan lines LNa and LNb) in the CT image $I_{CT}$. The beam-fan lines LNa and LNb are then delineated. At step 85, beam-fan lines LNc and LNd are superimposed and delineated in a side-view scanogram $I_{SIDE}$ by performing a similar procedure.

Figure 52:
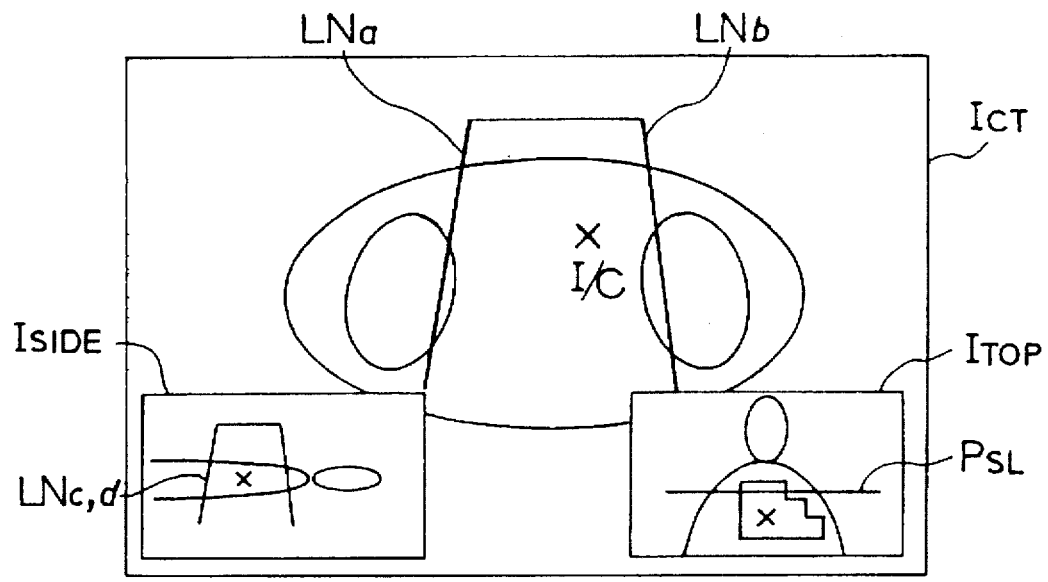
FIG. 52 shows an image with insets.

When images required in this embodiment are thus produced, the side- and top-view scanograms are inset into the CT image at step 86. Consequently, for example, as shown in FIG. 52, the side-view scanogram $I_{SIDE}$ and top-view scanogram $I_{TOP}$ are displayed as insets at the right and left lower corners of the CT image $I_{CT}$ associated with the designated slice position $P_{SL}$. Thus, plan information (including the isocenter I/C, radiation field RF, beam-fan lines LN, and slice position) and image information can be viewed in the same screen simultaneously. Screens need not be changed, though they must be in the prior art. Excellent operability ensues, and operational efficiency improves.

Figure 53:
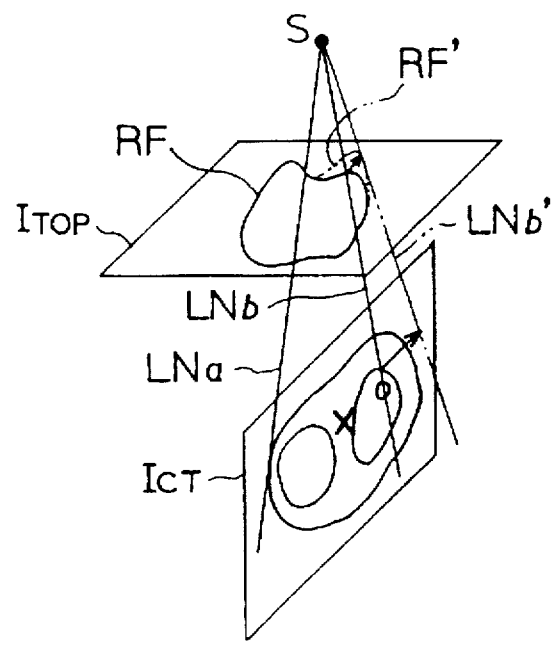
FIG. 53 is an explanatory diagram concerning correction of the contour of a radiation field.

According to the procedure in FIG. 46, it is determined whether the positions of the beam-fan lines LNa and LNb are changed in the CT image $I_{CT}$ with insets displayed using a pointing device (for example, a mouse) (step 87). For example, as shown in FIG. 53, assuming the beam-fan line LNb is moved to the position of a virtual line LNb', correction data concerning the contour of the radiation field RF (See the virtual line RF' in FIG. 53) is computed in order to cope with the change in position of the beam-fan line (step 88). The contour of the radiation field RF is then corrected in the top-view scanogram $I_{TOP}$ with the insets displayed (step 89). Until the procedure terminates, a change in position of a beam-fan line is dealt with (step 90).

Thus, while plan information and image information is being viewed in the same screen, the contour of a radiation field can be corrected by changing the positions of beam-fan lines but not changing the screen. Higher-precision therapy planning can be achieved quickly.

Instead of the side-view scanogram in this embodiment, a cross-sectional image produced by performing MPR or a transmission image reconstructed from a CT image will do. In this embodiment, the subject P is irradiated from above. A top view is therefore used to plan the contour of a radiation field and a side view is used to identify beam-fan lines. When the subject P is laterally irradiated, the top and side views are used for inverse purposes. The display form of a scanogram or the like is not limited to an inset. As far as images concerned are displayed in the same screen, they may be displayed in a multi-window form.

(The Fourth Embodiment)

The fourth embodiment will be described. The operation of this embodiment will be described in conjunction with FIGS. 54 to 59.

Figure 54:
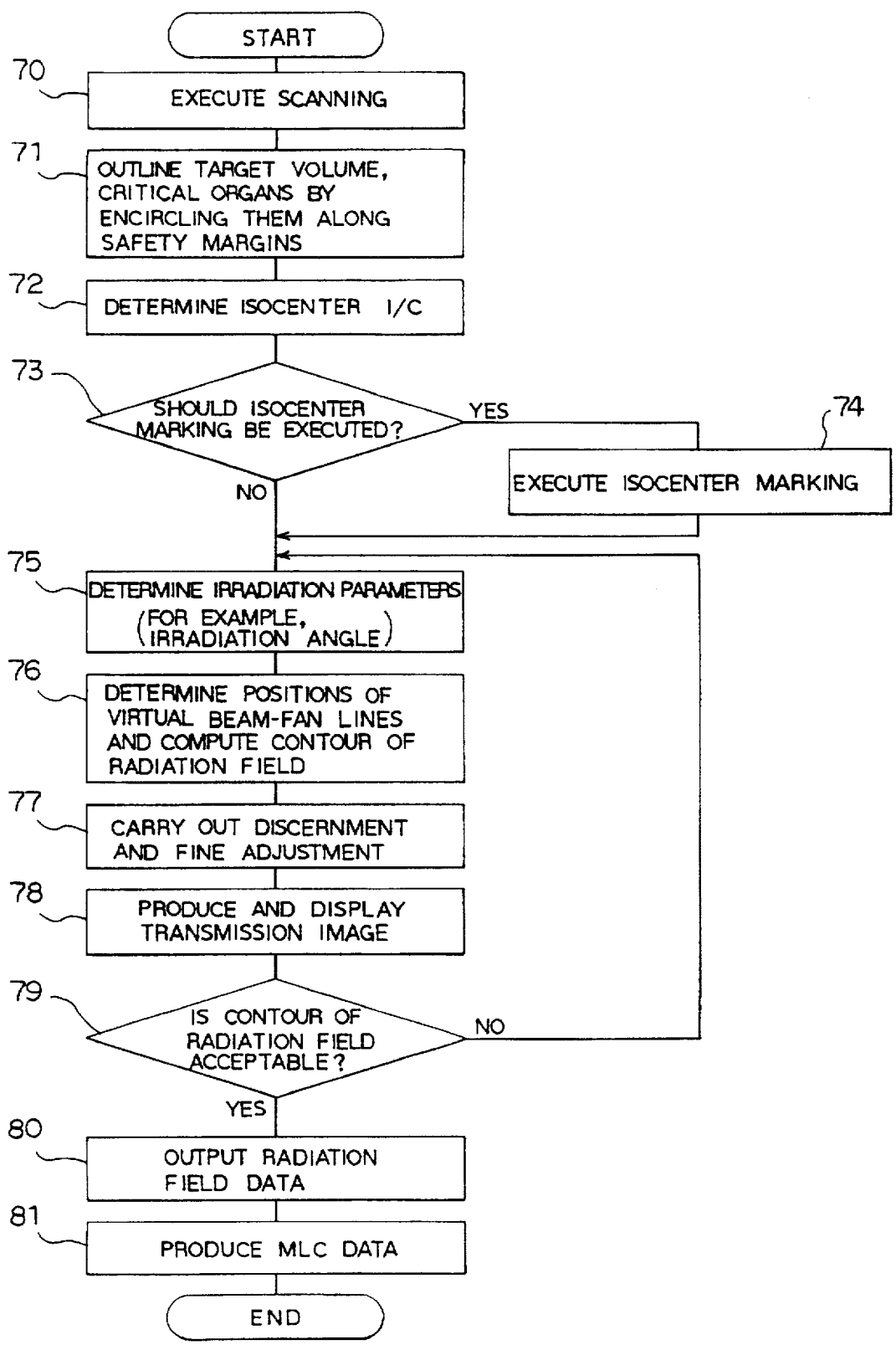
FIG. 54 is a flowchart carried out by a main control unit in the fourth embodiment.

The main control unit 40 in the CT system 1 is constructed so as to carry out the therapy planning procedure described in FIGS. 54 and 55.

To be more specific, at step 70, scanning is executed to produce a plurality of X-ray CT (axial) images rendering a region to be examined in response to a command entered at the input unit 48. When helical scanning is adopted, a plurality of CT images can be produced easily and quickly.

Next, at step 71, the plurality of CT images are used to three-dimensionally outline a target volume (tumor or the like) and critical organs by encircling them along their safety margins with a ROI.

At step 72, an isocenter I/C is determined using the positions of the outlined target volume and critical organs as indices. Two methods described below are available for the determination of an isocenter I/C.

One of the methods is: any one of a plurality of CT (axial) images is selected (whereby a z coordinate in the longitudinal direction of the patient couch is determined); the contours of the outlined target volume and others are then superimposed to and delineated on the axial image; and remaining x and y coordinates are determined with respect to the contours. The other method is: data concerning a plurality of CT (axial) images is used to produce an MPR image; the contours of a target volume and others are superimposed to and delineated on the MPR image; and an isocenter I/C is determined using a cross ROI.

At step 73, the main control unit 40 determines, based on an instruction entered at the input unit 48, whether isocenter I/C marking should be executed. When it is determined that isocenter marking should be executed, the coordinates (x, y, z) of the isocenter I/C in the three-dimensional space are sent to the positioning projector controller 49 at step 74. The three laser-type positioning projectors 27a to 27c project a mark at three points on a patient's body surface according to the planned coordinates (x, y, z) of the isocenter I/C. A Magic Marker or the like is used to trace the marks of projected light and thus draw markers on the body surface. When isocenter marking is thus completed, the patient can be released. Isocenter marking may be achieved by directly specifying an isocenter position or by retrieving locations of markers already drawn into the system and then determining an isocenter position relative to a reference position defined with the marker locations. According to the former method, a patient cannot be released until isocenter marking is completed. By contrast, the latter method makes it possible to release a patient after tentative marking is completed.

Control is then passed to step 75. An axial image rendering a plane closest to a plane containing the isocenter I/C is used to determine irradiation parameters such as a radiation irradiation angle, the number of irradiations, and an irradiation technique. In this case, when a therapy planning physician designates an angle, the main control unit 40 convolutes and superimposes virtual beam-fan lines (border lines of a radiation path) associated with the angle to and on the axial image. The positions of the beam-fan lines are adjusted so that the beam-fan lines will circumscribe the contour of a target volume, whereby an image for use in determining an optimal irradiation angle can be produced. In multi-frame display mode or the like, the irradiation angle can be recognized during changing of axial images or discerning of beam-fan lines.

Thus, an isocenter I/C position and an irradiation angle have been determined. At step 76, the main control unit 40 determines positions of virtual beam-fan lines and computes the contour of a radiation field.

At step 77, discernment and fine adjustment of the beam-fan lines and contour of a radiation field are carried out. This procedure is achieved according to the flowchart of FIG. 55.

Steps $77_1$ to $77_8$ in FIG. 55 relate to discernment and correction using a beam's path (hereinafter BP) image. Steps $77_{10}$ to $77_{16}$ relate to discernment using a beam's eye (hereinafter BE) image which is identical to the target image explained in the first embodiment.

Figure 56:
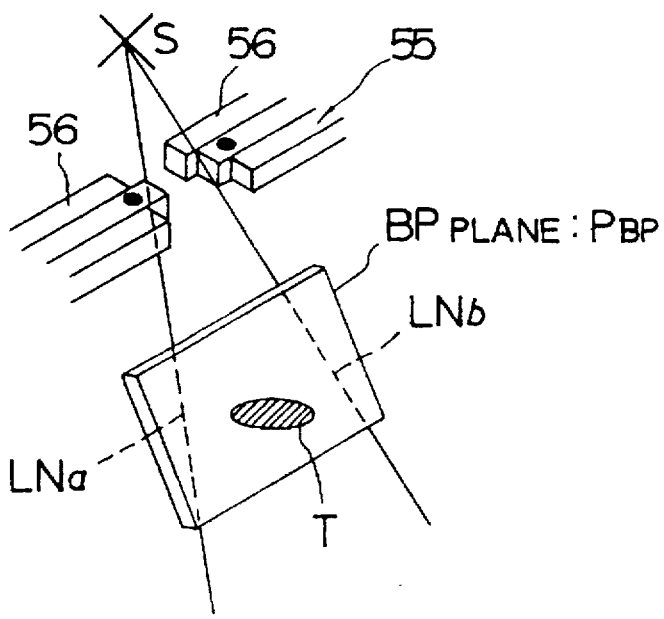
FIG. 56 is an explanatory diagram concerning a beam's path (BP) plane.
Figure 57:
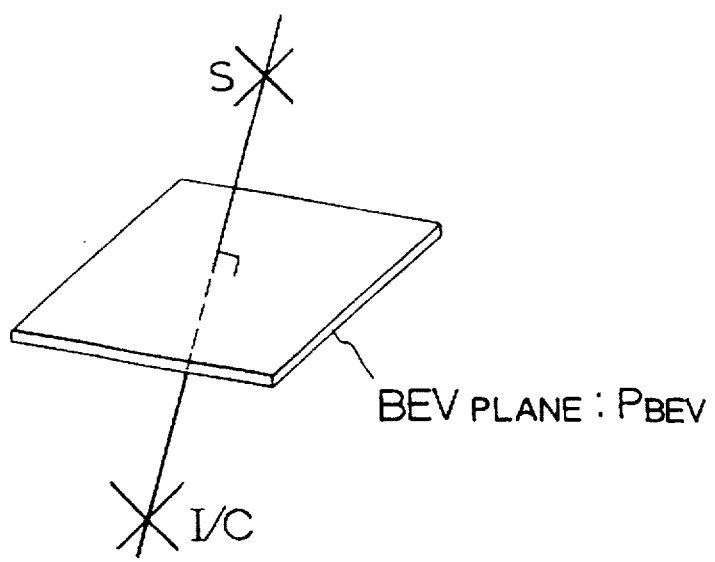
FIG. 57 is an explanatory diagram concerning a beam's eyes view (BE) plane.

The BP image renders, as shown in FIG. 56, a plane $P_{BP}$ that is comparable to an oblique plane of a subject containing a radiation source and lying in parallel with a radiation beam. The plane $P_{BP}$ is determined with a rotation angle of the collimator 55 and a distance of an I/C plane (that is a plane containing the isocenter I/C and being orthogonal to a line linking the radiation source S and isocenter I/C) from the isocenter i/C. The BEV image renders, as shown in FIG. 57, a plane $P_{BE}$ that is comparable to an oblique plane of a subject perpendicular to the line linking the radiation source S and isocenter I/C. The plane $P_{BE}$ is determined uniquely with a distance from the radiation source S.

In FIG. 55, data concerning a rotation angle of the collimator 55 and a distance of the I/C plane from the isocenter I/C, which determines a plane $P_{BP}$, is fetched from the input unit 48 (step $77_1$). Based on this data and known data, MPR is performed to produce a BP image for each portion of a plane $P_{BP}$ allotted to each pair of leaves 56 of the multileaf collimator 55 (step $77_2$). For example, when the multileaf collimator 55 is of what is called "1-cm MLC" type, the BP image is produced at intervals of 1 cm from the isocenter I/C on the I/C plane.

For each plane $P_{BP}$, positions of beam-fan lines T are computed according to the contour of a radiation field (step $77_3$). The beam-fan lines T are then convoluted to and delineated on the BP images rendering the planes $P_{BP}$ (step $77_4$). Thus, the therapy planning physician can discern the positions of beam-fan lines accurately.

Through the screen, when the therapy planning physician determines that fine adjustment is not required (the result of determination made at step $77_5$ is negative), the subsequent BP image is handled for superposition and discernment (steps $77_4$ and $77_5$).

When the result of determination made at step $77_5$ is affirmative; that is, when it is determined that fine adjustment is required, correction values indicating new positions of the beam-fan lines T are entered (step $77_6$). The contour of a radiation field RF defined by each pair of leaves 56 responsible for each portion of each plane $P_{BP}$ is thus modified (step $77_7$). At step $77_8$, it is determined whether handling of BP images is completed. If the result of determination is negative, control is returned to step $77_4$.

Discernment using a BE image is then commenced. For discerning the contour of a radiation field using a BE image, the main control unit 40 retrieves distance data representing a distance from the radiation source 2 from the input unit 48 (step $77_{10}$). MPR is then performed to produce a BE image according to the distance (step $77_{11}$). The contour of the radiation field RF is enlarged or reduced according to the distance of the plane $P_{BE}$ rendered by the produced BE image from the radiation source S (step $77_{12}$). The contour of the radiation field RF is then superimposed to and delineated on the BE image $P_{BE}$ (step $77_{13}$).

The therapy planning physician can now discern through the BE image rendering a plane $P_{BE}$ at an arbitrarily-specified depth whether the contour of the radiation field RF is consistent with that of the target volume (step $77_{14}$). If the discernment concludes that the contour of the radiation field RF is acceptable, it is determined whether discernment is completed (step $77_{15}$). If the result of determination is negative, control is returned to step $77_{10}$. If the result of determination made at step $77_{14}$ is negative (that is, when the contour of the radiation field RF is inconsistent with that of the target volume), for example, a message saying that the beam-fan lines T should be finely adjusted is displayed (step $77_{16}$). Control is then passed to step $77_{15}$. When fine adjustment of beam-fan lines is commanded, the therapy planning physician reruns steps $77_1$ to $77_8$.

When fine adjustment and discernment are thus completed, the main control unit 40 returns control to step 78 in FIG. 54 and processes image data concerning a plurality of CT (axial) images by performing a known MPR sequence so as to produce a transmission image comparable to a projection image produced relative to the radiation source S. The contour of the radiation field RF and others are then superimposed to and delineated on the transmission image. Final discernment can now be carried out. The transmission image can be used as a verification image for treatment. Incidentally, a scanogram can substitute for the transmission image.

If it is determined through the transmission image that the contour of the radiation field RF is unacceptable, control is returned to step 75. The aforesaid procedure is repeated. If the result of determination made at step 79 is negative (it is found through the transmission image when the contour of the radiation field RF is acceptable), finalized radiation field data is supplied (step 80). For reflecting the contour of a radiation field on the radiotherapy apparatus 2, communication may be employed or an OHP film or the like may be used to draw the contour of a radiation field and others (the drawing may be of a reduced size dependent on the size of a tray on which the film is placed).

Finally, the finalized contour of the radiation field RF is used to produce data concerning the angular position of the whole multileaf collimator 55 and the positions of the pairs of leaves 56 as MLC data (step 81).

Figure 58:
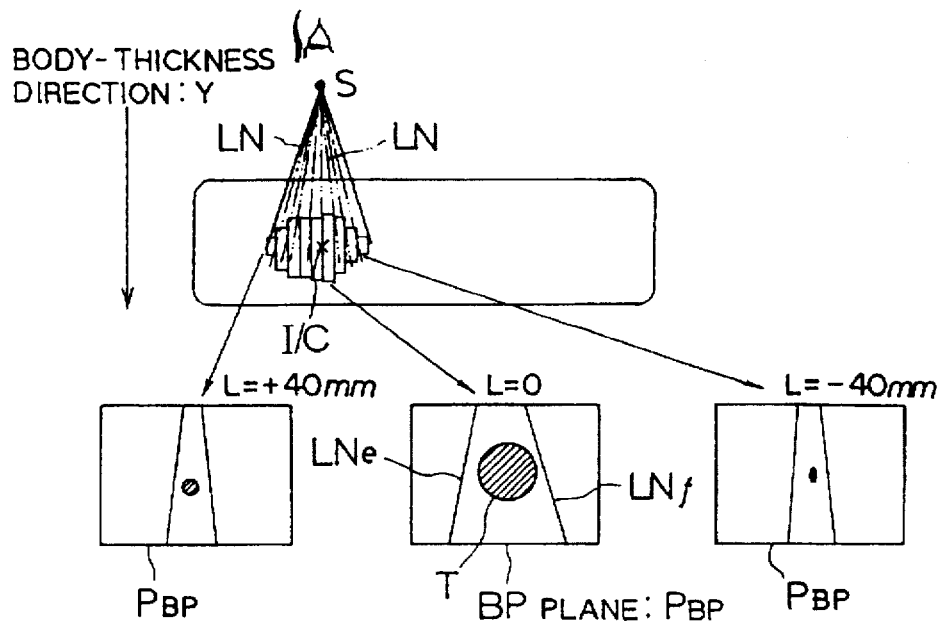
FIG. 58 is an explanatory diagram concerning confirmation of positions of beam fan lines using the BP plane.

When the BP image is used to discern whether beam-fan lines are defined optimally for the contour of a target volume, only a distance L of an I/C plane from an isocenter I/C should be entered together with a rotation angle of the collimator 55. As shown in FIG. 58, assuming that the distance L is set to 0 (on the I/C plane), +40 mm, and −40 mm, a BP image is automatically produced according to each inter-leaf width (for example, 1 cm on the I/C plane) associated with each of the distance values. A contour T of a target volume and beam-fan lines LNe and LNf are superimposed to and delineated on the BP images. When what is called a "1-cm MLC" collimator is employed, the BP image is produced at intervals of 1 cm from the I/C plane. Whether the beam-fan lines LNe and LNf on an oblique plane along a radiation path are appropriate can be discerned for each pair of leaves. Compared with conventional discernment using axial images, discernment can be achieved more reliably. At the same time, the positions of the beam-fan lines LNe and LNf can be corrected if necessary through each BP image. When the positions of the beam-fan lines LNe and LNf are corrected, the contour of the radiation field RF is modified automatically and responsively. Thus, operation is markedly simplified and labor and assigned to a therapy planning physician is greatly lightened.

Figure 59:
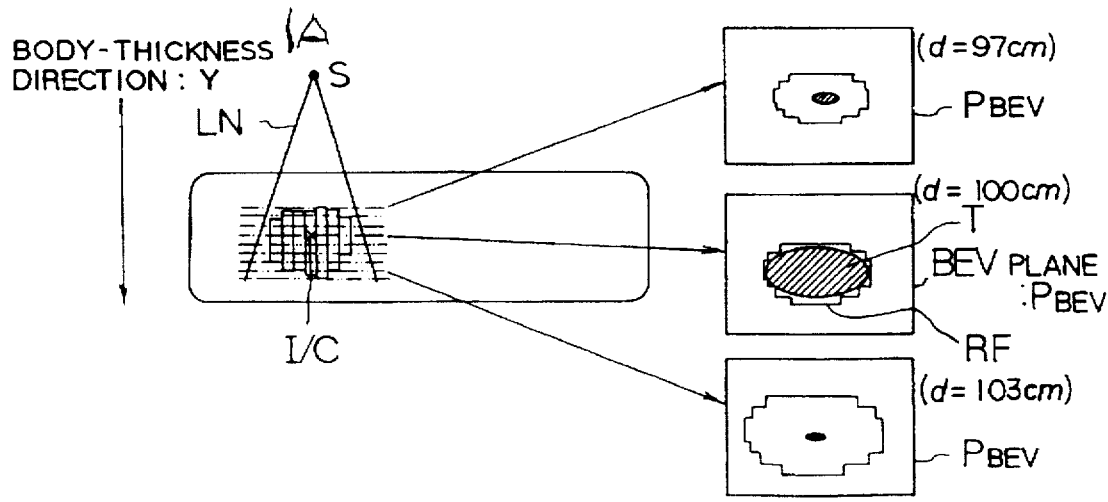
FIG. 59 is an explanatory diagram concerning confirmation of a contour of a radiation field using the BE plane.

Using a BE image, it is easily discernible whether the contour of a radiation field RF is defined optimally for that of a target volume T. As shown in FIG. 59, assuming that a distance d from the radiation source S is set to 97 cm, 100 cm, and 103 cm, a BE image is automatically computed for each of the planes $P_{BP}$ determined with the distance values. An radiation field enlarged or reduced according to the distance values is automatically superimposed to and delineated on each of the BE images. Thus, this sequence is executed merely by designating a value for the distance d. That is to say, the contour of a radiation field can be discerned with enjoyment of excellent operability. When the contour of a radiation field is unacceptable, the positions of beam-fan lines can be finely readjusted for each pair of leaves.

In the aforesaid embodiment, a multileaf collimator is used as a collimator installed in a radiotherapy apparatus. Alternatively, a collimator realized by manually arranging lead blocks will do.

The contents of discernment and correction performed at step 77 in FIG. 54 may be discernment and correction of positions of beam-fan lines, and responsive correction of a contour of a radiation field.

As described so far, according to an embodiment of a radiotherapy apparatus according to the present invention, a BP image rendering a plane containing a radiation source and lying in parallel to a beam fan of radiation emanating from the radiation source is displayed together with the beam-fan lines in a screen. According to another embodiment, when the positions of beam-fan lines are manually corrected through a monitor, the contour of a radiation field is modified automatically and responsively. Beam-fan lines defining a radiation path are displayed in a reliable and easy-to-see fashion. In addition, the contour of a radiation field can be corrected effortlessly. High-precision therapy planning can be achieved with enjoyment of excellent operability.

(The Fifth Embodiment)

Next, the fifth embodiment will be described with reference to FIGS. 60 to 62.

In the fifth embodiment, drilling for three-dimensional image display is employed in radiotherapy planning. Drilling is a three-dimensional image processing technique. As shown in FIG. 60A, a free-shape ROI and a depth h from the surface of an object B are indicated in a surface image of the object B. A cross-sectional image Isec associated with the ROI is synthesized with the surface image (See FIG. 60B).

Conventionally, drilling is designed to be implemented in an X-ray CT scanner. An internal cross section at a designated depth is viewed with parallel lines of sight. A beam viewed from a radiation source in a radiotherapy apparatus is shaped like a cone spreading from one point. The drilling technique therefore cannot be adapted for a radiotherapy planner realized with a CT system in accordance with the present invention.

Figure 61:
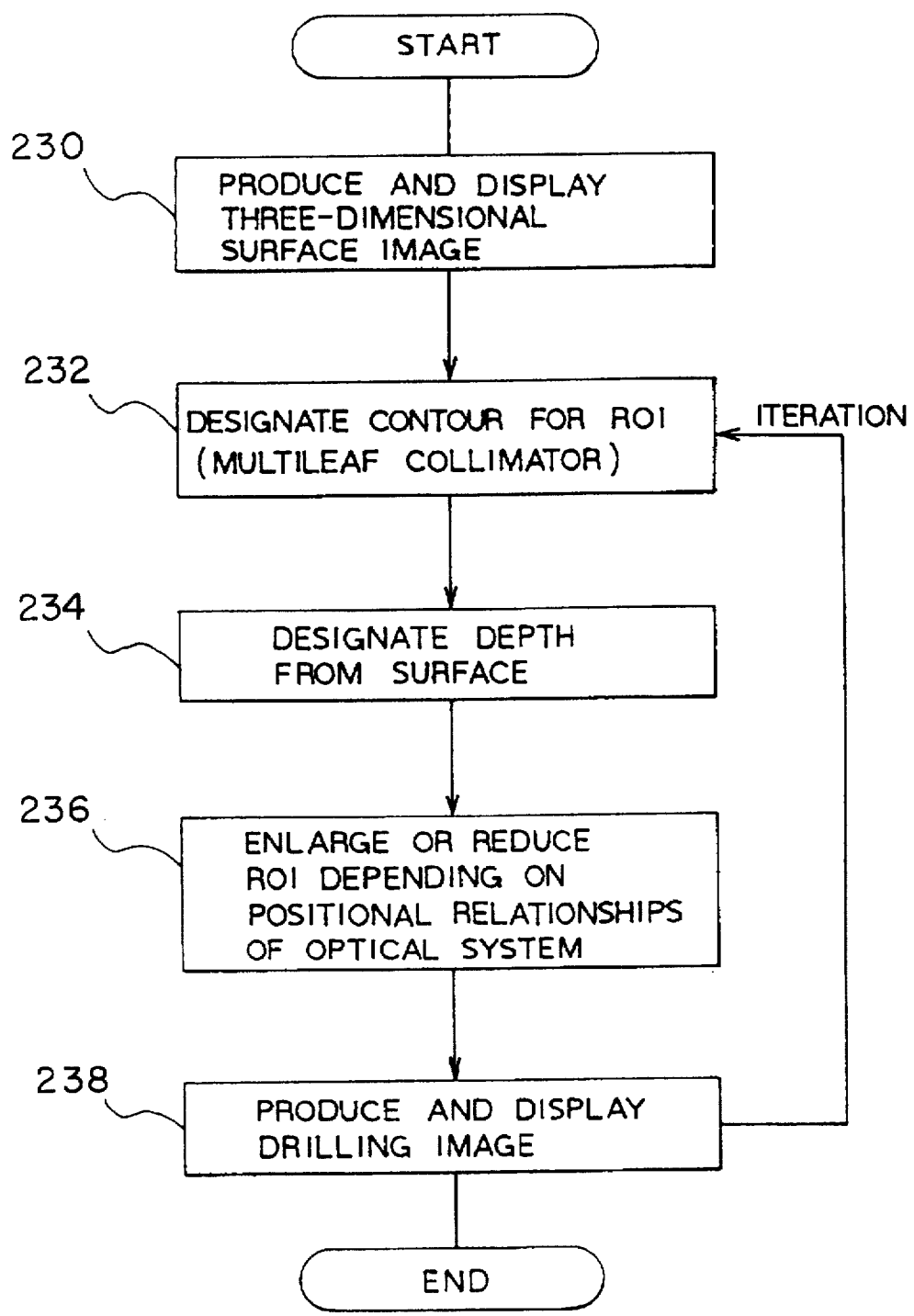
FIG. 61 is a flowchart describing a sequence of drilling to be performed in the course of radiotherapy planning in the fifth embodiment.
Figure 62:
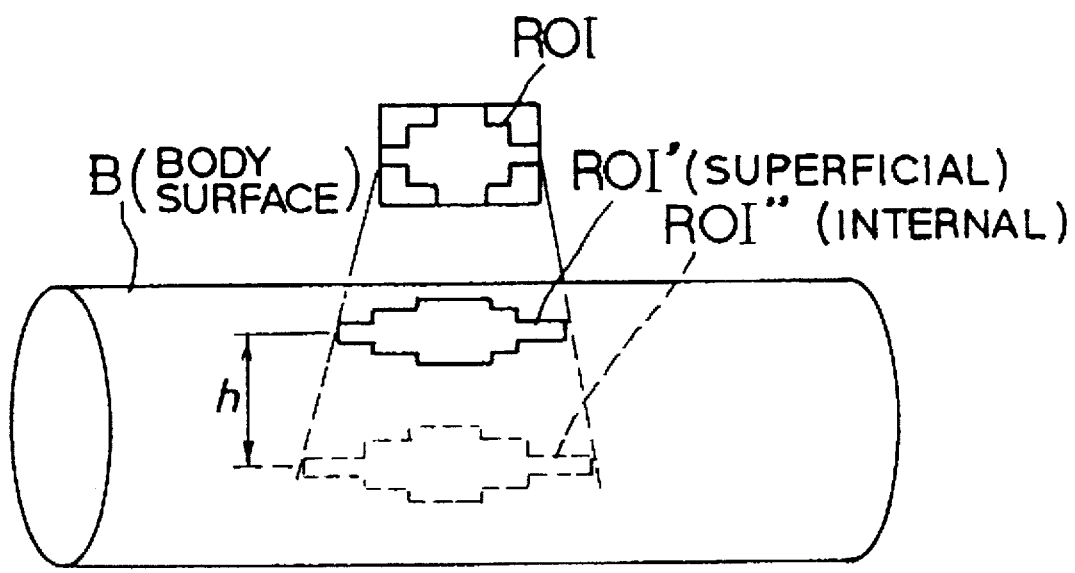
FIG. 62 is an explanatory diagram concerning a change in depth direction of the contour of a ROI during drilling.

The main control unit 40 in the CT system 1 in this embodiment executes the procedure shown in FIG. 61. Note that consecutive axial images produced by performing X-ray CT scanning have been used to produce voxel data.

At step 230, a three-dimensional surface image is produced using the voxel data and then displayed. At step 232, the contour of the opening of the multileaf collimator 55 defined during therapy planning is designated as that of an original ROI. At step 234, a depth h from a body surface to a desired cross section is designated. This designation is achieved by entering, for example, numerical values at the input unit 48 (on the assumption that a region to be observed has already been determined). At step 236, based on the positional relationships of an optical system; that is, a distance from a radiation source to a body surface and the designated depth h, the size of the ROI (size of the opening of the collimator) is automatically corrected (increased or decreased) depending on the depth h (See ROI' and ROI" in FIG. 62). Control is then passed to step 238. Values of pixels whose locations are within a given thickness in the three-dimensional surface image are added up and used as projection data concerning the internal ROI" plane at the designated height h. A drilling image rendering the internal ROI" plane is thus produced and then synthesized with the surface image. Steps 232 to 238 are repeated if necessary.

An axial, coronal, or sagittal plane containing a ROI determined with the opening of a collimator may be designated, and then internal information may be cut out or the luminance of a region surrounding the ROI may be reduced. Thus, only the internal data concerning a subject may be subjected to MPR. Alternatively, the distribution of radiation doses within an automatically-corrected ROI may be computed and rendered.

As mentioned above, according to this embodiment, a ROI interlocked with an opening of a multileaf collimator is designated in the state of therapy planning. Drilling can be executed in a preferable fashion. When a depth for drilling has the same value as a distance from a lesion, information concerning the visualized lesion can be acquired and whether a radiation path leading to the lesion is appropriate or not can be recognized intuitively.

A collimator usable in this embodiment is not limited to a multileaf collimator but may be, for example, a monoblock collimator.

(The Sixth Embodiment)

The sixth embodiment will be described with reference to FIGS. 63 to 71. In this embodiment, a technique for producing a maximum-value projection (MIP) image is introduced to radiotherapy planning.

To begin with, a normal procedure of producing a maximum-value projection image will be described in conjunction with FIGS. 63A to 63D. Thereafter, a procedure of producing a maximum-value projection image for radiotherapy planning will be described in conjunction with FIG. 64.

A normal maximum-value projection image is produced as described below. That is to say, voxel data (whose depth is determined with the same number of pixel values as that of a slice image) is produced using a plurality of consecutive slice images (planar images) such as CT images (See FIGS. 63A and 63B). The voxel data is then processed to analyze pixel values set in array on respective lines corresponding to parallel X rays generated in a desired direction (See FIG. 63C). Maximum ones of the pixel values detected along the respective lines are computed and the pixels with the maximum values are displayed as a fluoroscopic image projected on a plane (See FIG. 63D). The displayed image is a maximum-value projection image. Any fluoroscopic direction can be designated. A plurality of consecutive slice images may be not only CT images but also MR tomographic images or NMR tomographic images (of axial, coronal, sagittal, or oblique planes). If only trajectories of fluoroscopic X rays can be identified in a tomographic image, production of voxel data can be excluded from the foregoing procedure.

Figure 64:
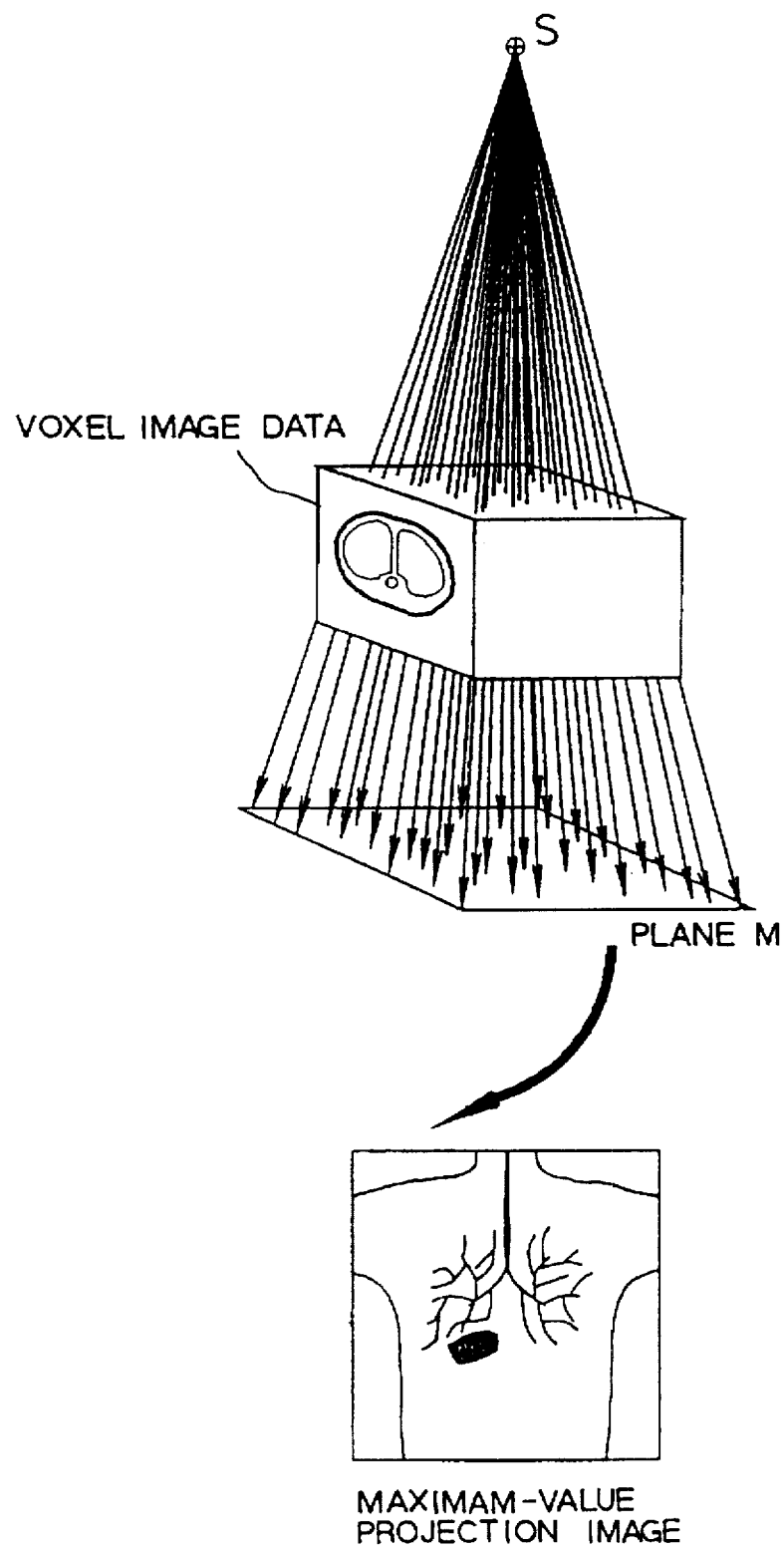
FIG. 64 is an explanatory diagram concerning production of a maximum-value projection image during radiotherapy planning.
Figure 65:
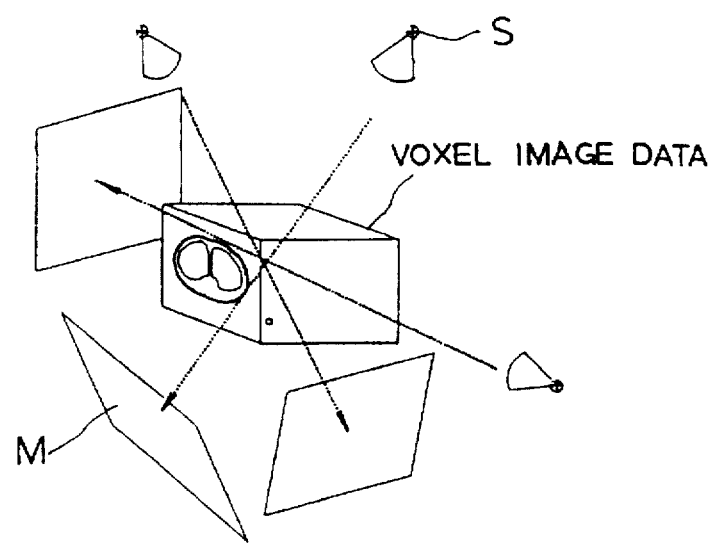
FIG. 65 shows various directions of projecting a fluoroscopic image corresponding to a maximum-value projection image.

A procedure of producing a maximum-value projection data for radiotherapy planning is identical to the aforesaid procedure until the step of producing voxel data. For radiotherapy planning, when voxel data is produced, as shown in FIG. 64, a plurality of fluoroscopic X rays spreading like a pyramid from the radiation source S (one point) to a volume represented by the voxel data are determined. Maximum pixel values on respective lines corresponding to the fluoroscopic X rays are accumulated for a plane M and the pixels with the maximum values are displayed as a planar maximum-value projection image. This production procedure is carried out by, as shown in FIG. 65, changing the angle of the radiation source S and the angle of the plane M opposed to the radiation source S, whereby maximum-value projection images comparable to fluoroscopic images projected at various angles can be produced.

Figure 66:
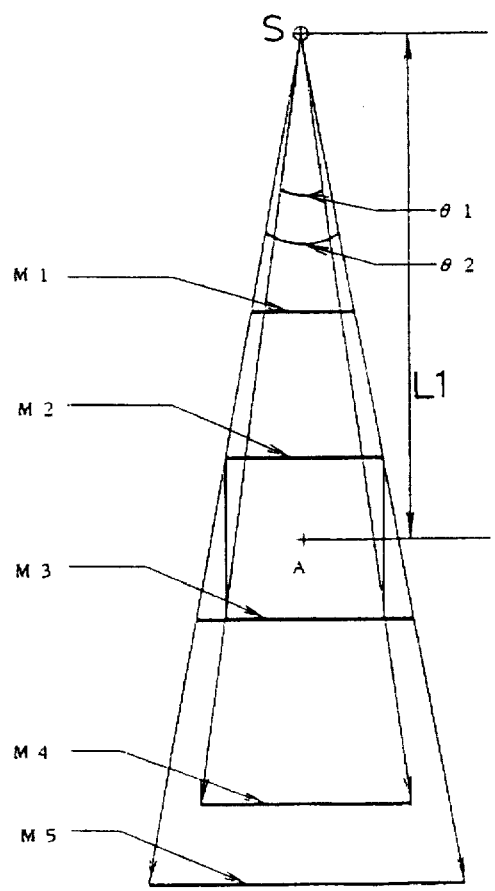
FIG. 66 is an explanatory diagram concerning positional relationships among maximum-value projection images and pixel sizes.

Maximum-value projection images for radiotherapy planning are produced as mentioned above. Positional relationships of maximum-value projection images practically used for therapy planning as well as pixel sizes of pixels residing in maximum-value projection images will be described in conjunction with FIG. 66. In FIG. 66, point S indicates the position of a radiation source. Point A indicates an isocenter. Distance L1 indicates a distance from the radiation source S to the isocenter. Points A and S and distance L1 have fixed or variable values inherent to a radiotherapy planner. M1 denotes a position of a shadow tray. M2 denotes a position of the top of a volume represented by voxel data or a position of a body surface. M3 denotes a position of the bottom of the volume or a position of a patient couch. M4 and M5 denote positions of X-ray film cassettes in an X-ray apparatus. The apex angle of a beam fan formed by radiation emanating from point S varies between an angle θ2 associated with the largest voxel size and an angle θ1 associated with the size of a voxel comparable to a volume transmitted by radiation.

For producing a maximum-value projection image, voxel data is processed to produce a maximum-value projection image (for each of positions M1 to M5) comparable to fluoroscopic images projected from point S (source) separated by a distance L1 from the isocenter A in a volume represented by the voxel data.

A pixel size set for producing or displaying a maximum-value projection image (dependent on a distance from point S set for producing a maximum-value projection image) is indicated in each of maximum-value projection images produced as images projected on planes at the positions M1 to M5 in FIG. 66. Whichever one of the planes is selected depends on a therapy planning technique.

FIGS. 67 to 69 show the first to fourth practical examples of a facility for producing maximum-value projection images in the sixth embodiment. High-speed processors shown in the drawings are newly added to the console configuration shown in FIG. 4. An input unit and an image display unit correspond to the input unit 48 and display unit 47 respectively (different reference numerals are assigned for better description).

A facility of the first practical example shown In FIG. 67 includes a high-speed processor 220 capable of producing a maximum-value projection image in any fluoroscopic angular direction shown in FIG. 64. The high-speed processor 220 receives definition data DF (the values of L1, θ1 or θ2, and M1 to M5 in FIG. 66) and slice images SL. The processor 220 executes processing illustrated in FIGS. 64 and 66 so as to produce a maximum-value projection image IM. The projection image IM is fed to an image display unit 220 and then displayed. Data required for rotating the maximum-value projection image is fed to the processor 220 using an input unit 224 (keyboard, mouse, or trackball), if necessary. The maximum-value projection image is then reconstructed according to the data. A radiation field is outlined over the displayed maximum-value projection image using the input unit 224.

A facility of a practical example shown in FIG. 68 includes not only the high-speed processor 220 but also another high-speed processor 226.

The high-speed processor 226 is designed to perform various kinds of image processing on a plurality of consecutive slice images to be used for producing voxel data. One kind of image processing (1) is such that slice images produced with a contrast medium administered and slice images produced without it are used to produce subtraction images, and the subtraction images are used to produce a maximum-value projection image. This image processing provides an image rendering only a region, to which a contrast medium has been administered, in a enhanced fashion. Another image processing (2) is such that images resulting from the processing (1) are inverted to negative images, and the negative images are used to produce a maximum-value projection image. This image processing provides an image rendering a region, to which a contrast medium has not been administered, in a enhanced fashion. Yet another image processing (3) is such that a slice image, of which specified range is assigned pixel values representing high luminance and which is often employed in a handy display, is used to produce a maximum-value projection image. This image processing provides an image rendering a region comparable to the specified range in an enhanced fashion. Another image processing (4) is such that images rendering specified areas in slice images are used to produce a maximum-value projection image. This image processing provides an image rendering the specified areas alone. Thus, highly-discernible images that cannot be yielded by plan X-ray irradiation can be provided.

For executing the above image processing, a command designating a desired kind of image processing (preprocessing) selected from the above (1) to (4), a processing direction, and other data are entered at the input unit 224 and then sent to the high-speed processor 226. The processor 226 then executes designated image processing (subtraction image production, inverse image production, high-luminance image production, or specified-area image production) for original slice images SL. Resultant slice images SL' are then sent to the high-speed processor 220. The processors 220 produces a maximum-value projection image IM according to the processing illustrated in FIGS. 64 and 66 as mentioned above, and displays it. The input unit 224 is used to outline a radiation field in the maximum-value projection image IM and rotate the maximum-value projection image in irradiation directions employed in a radiotherapeutic irradiation technique (rotation irradiation or conformation irradiation). A radiation field is then defined for each of the irradiation directions.

The high-speed processors 226 and 220 in the front and back stages may be configured in the same processor.

Figure 70:
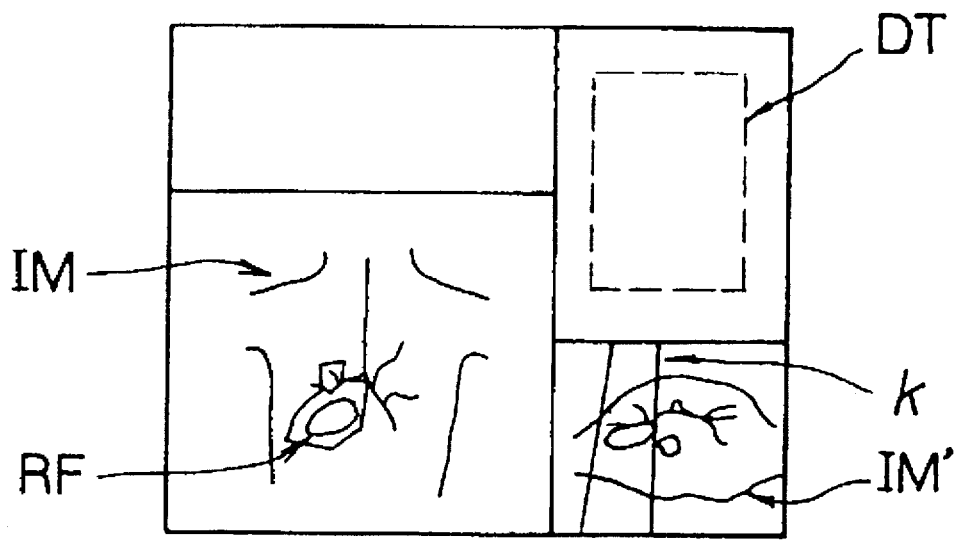
FIG. 70 shows an example of a screen in the third example.
Figure 71:
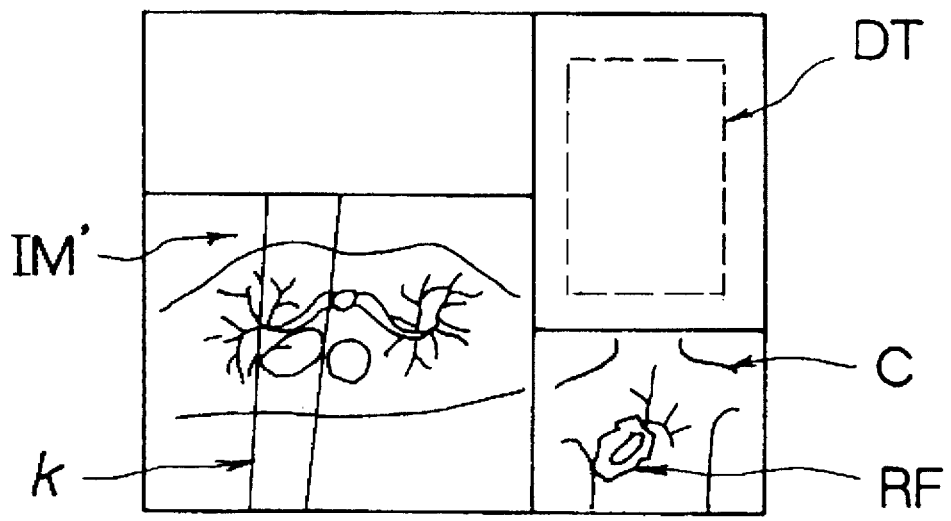
FIG. 71 shows another example of a screen in the third example.

In a facility shown in FIG. 69, therapy plan data DT and slice images SL or SL', which are produced according to the process described in conjunction with FIG. 67 or 68, are fed to the high-speed processor 220. The high-speed processor 220 uses the slice images SL or SL' to produce a maximum-value projection image IM'. The therapy plan data and maximum-value projection image IM' are used to display a fluoroscopic image rendering the lateral part of a radiation field in the display unit 222. For "lateral" in the lateral part, the direction described in conjunction with FIGS. 67 and 68 is regarded as a longitudinal direction. A trajectory k of radiation passing through the radiation field is delineated in the maximum-value projection image IM'. The trajectory k is identified in the maximum-value projection image IM'. If normal tissues may be exposed to radiation, the trajectory k is corrected in the maximum-value projection image IM. FIGS. 70 and 71 show examples of screens, which enable identification and setting (correction) at the same time, on the image display unit 222. In FIGS. 70 and 71, DT denotes therapy plan data (for example, a radiation field number, a pixel size for each image, and coordinates and an angle at which each image is displayed). RF denotes a radiation field.

As mentioned above, in the sixth embodiment, a maximum-value projection image can be rotated. This means that an image can be produced in any desired direction. Using a maximum-value projection image, a radiation field for rotation or conformation irradiation can be defined and identified. Even when some organs must not be exposed to radiation, an irradiation direction need not be set in each axial image but should merely be set in a maximum-value projection image in the same manner as in a scanogram (X-ray image). CT scanning of a lesion should therefore be performed only once. This results in a reduced X-ray exposure and obviates the necessity of setting an irradiation direction in each axial image. A load to an operator therefore shrinks. Other advantages are that: a plan can be checked three-dimensionally; (rotation or conformation) irradiation planning is simplified; and views that are unavailable in a scanogram or X-ray image can be provided.

(The Seventh Embodiment)

A radiotherapy system including a radiotherapy planner in accordance with the seventh embodiment of the present invention will be described in conjunction with FIGS. 72 to 77.

The operation of the seventh embodiment will be described in conjunction with FIGS. 72 to 76.

Figure 72:
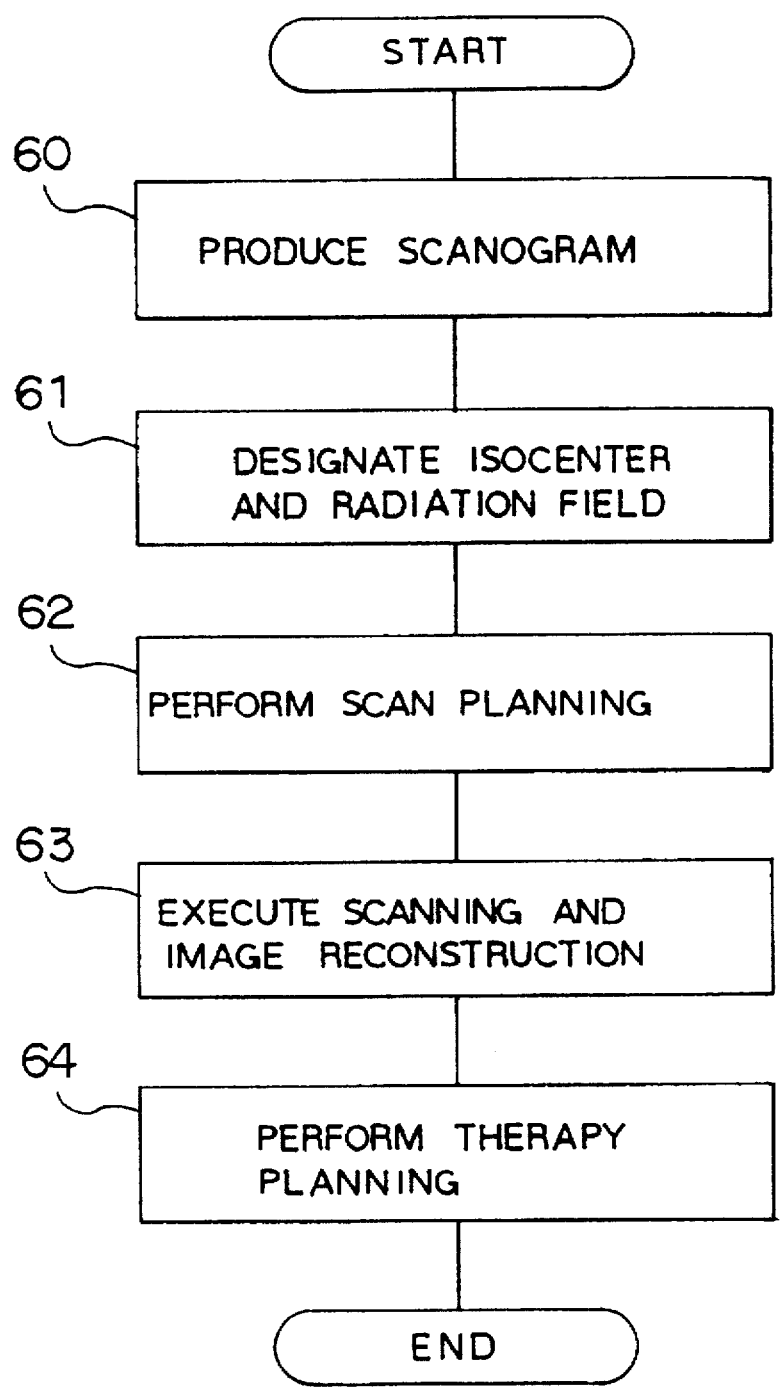
FIG. 72 is a flowchart describing therapy planning executed by a main control unit in the seventh embodiment.
Figure 73:
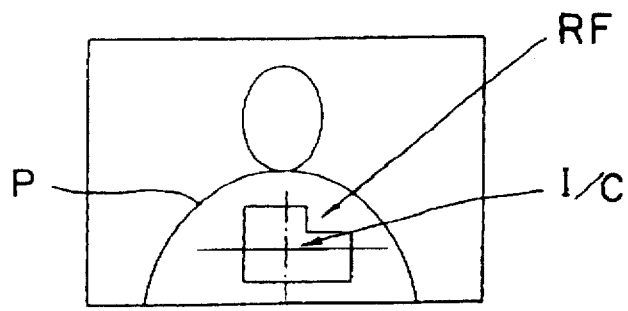
FIG. 73 shows the relationships among a scanogram, an isocenter, and a radiation field.
Figure 74:
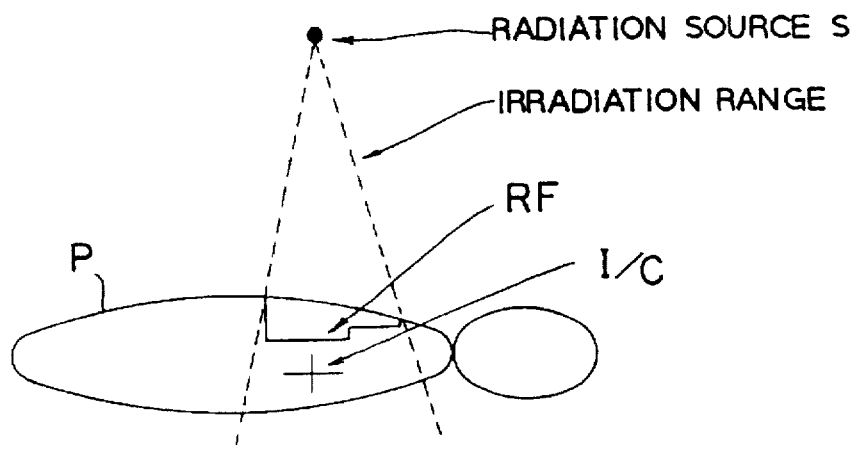
FIG. 74 shows the relationships among a radiation source, an isocenter, and a radiation field.

The main control unit 40 in the CT system 1 executes therapy planning according to the procedure shown in FIG. 72. First, at step 60 in FIG. 72, the main control unit 40 commands that a scanogram of the subject P be produced. The scanogram is, as shown in FIG. 73, displayed on the display unit 47. A radiation field RF covering a lesion is defined in the scanogram using a ROI manipulated at the input unit 48. Likewise, an isocenter I/C corresponding to a rotation center for radiotherapy is specified (at this time, when a depth must be specified, axial images are used in addition). FIG. 74 is a conceptual diagram showing the relationships of a radiation source S with the radiation field RF and isocenter I/C.

Figure 75:
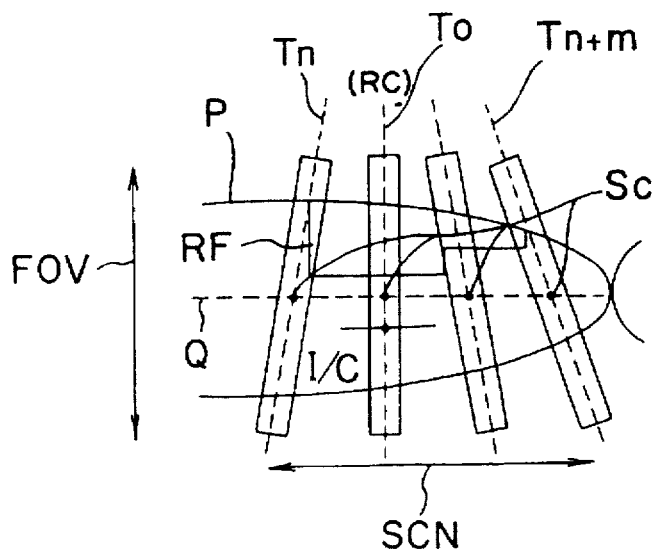
FIG. 75 is an explanatory diagram concerning an example of a slice.
Figure 76:
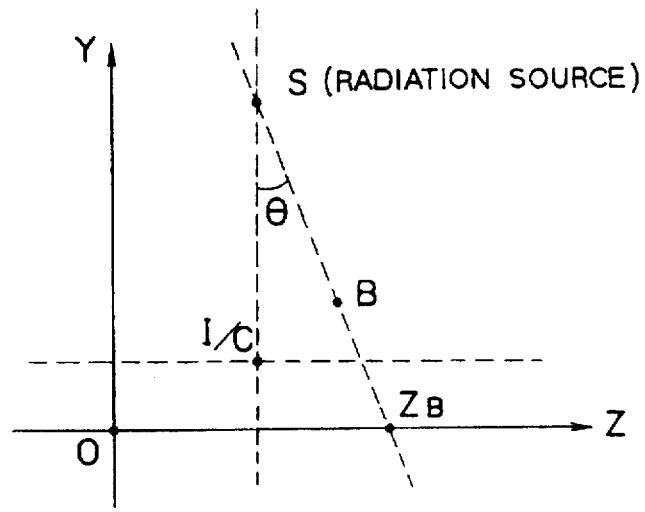
FIG. 76 is an explanatory diagram concerning calculation of a tilt angle of a gantry and a movement of a couchtop.

Control is then passed to step 61. Scan planning is carried out in terms mainly of the isocenter I/C. Specifically, as shown in FIG. 75, a radiation path To linking the radiation source S and isocenter I/C is defined, and a scan center Sc for the radiation path is specified. An axis Q is defined to pass through the scan center Sc and be orthogonal to the radiation path To. Values FOV and SCN defining an FoV (Field of View) range in which images are to be reconstructed are entered at the input unit 48. When a coordinate axis and a range to be scanned are thus determined, particular scanning plan information is acquired. First, scan planning (for helical scanning, only a position of reconstruction is planned) is performed so that a reconstruction center Rc along the radiation path To will be consistent with the isocenter I/C. For visualizing regions away from the isocenter I/C in a body-axis (z-axis) direction, scan planning is performed so that the gantry will be tilted in line with radiation paths Tn, etc., and Tn+m leading to the regions. Assuming that, as shown In FIG. 76, a straight line SB links a region to be observed B and the radiation source S, the position of a couchtop is determined in terms of an intersection $Z_B$ of the line SB with the z-axis. An angle θ in FIG. 76 is regarded as a tilt angle. Thus, control data for use in controlling the gantry 11 and couchtop 12a is computed.

When scan planning is thus completed, control is passed to step 63. The patient couch control unit 41 and gantry control unit 42 are driven according to plan data, so that scanning and image reconstruction will be carried out. At step 64, based on resultant reconstructed images, radiotherapy planning is carried out: an irradiation technique is determined; a radiation field is finely adjusted; and beam-fan lines are identified. The plan data is used for treatment accomplished by means of the radiotherapy apparatus 2.

Figure 77:
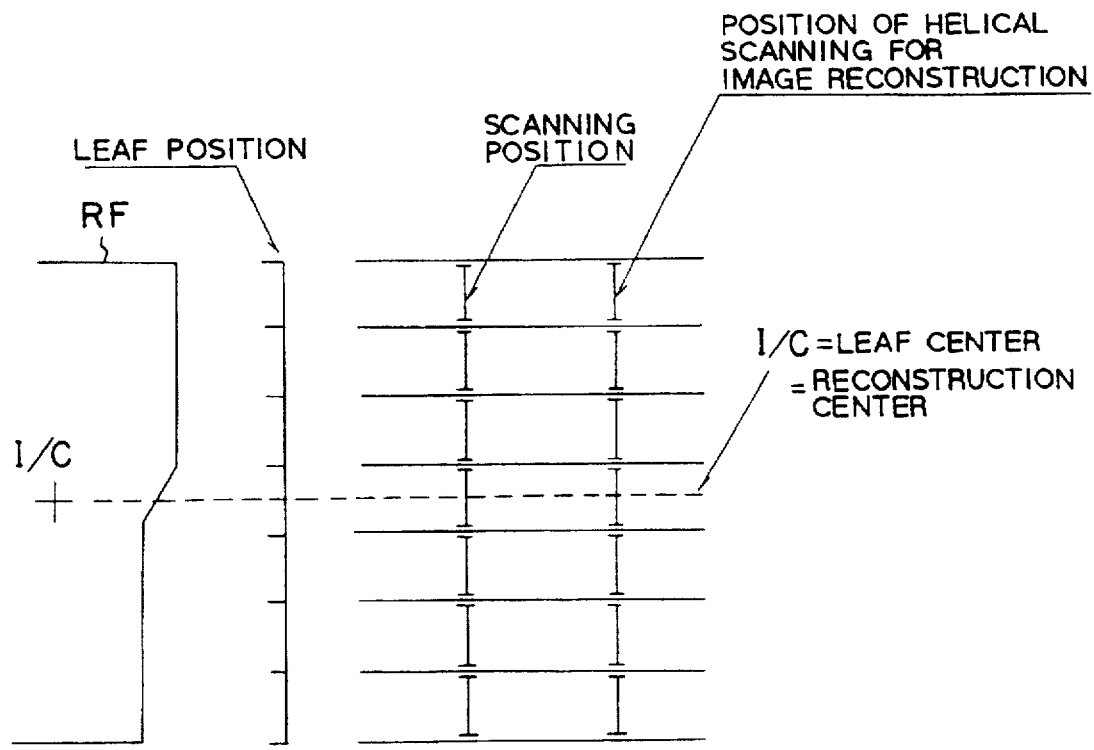
FIG. 77 is an explanatory diagram concerning an example of slices determined in consideration of a leaf thickness.

As for scanning, only a region of interest such as an edge of a radiation field or a critical organ may be scanned, or scanning may be performed equidistantly. For equidistant scanning, as shown in FIG. 77, scan planning may be achieved in consideration of the thickness of each leaf 56 (for example, 1 cm on a body surface) of the multileaf collimator 55. Specifically, for scanning a region containing the isocenter I/C, the isocenter I/C, the center of a leaf, and a reconstruction center are aligned with one another. In addition, a slice thickness is set to the same value as the leaf thickness (or the slice thickness may be an integral multiple of the leaf thickness).

For irradiating a subject through the lateral region, scan planning and scanning are carried out so that the gantry or patient couch will be moved.

As mentioned above, scanning can be carried out in consideration of an isocenter and an irradiation angle. In resultant images, therefore, a slice position (eventually, a slice thickness) is consistent with an isocenter and a leaf position (eventually, a leaf thickness) of a multileaf collimator. Thus, images rendering a position and angle of an isocenter which are helpful in actual therapy planning can be produced quickly. Therapy planning can therefore be achieved more accurately.

(The Eighth Embodiment)

Figure 78:
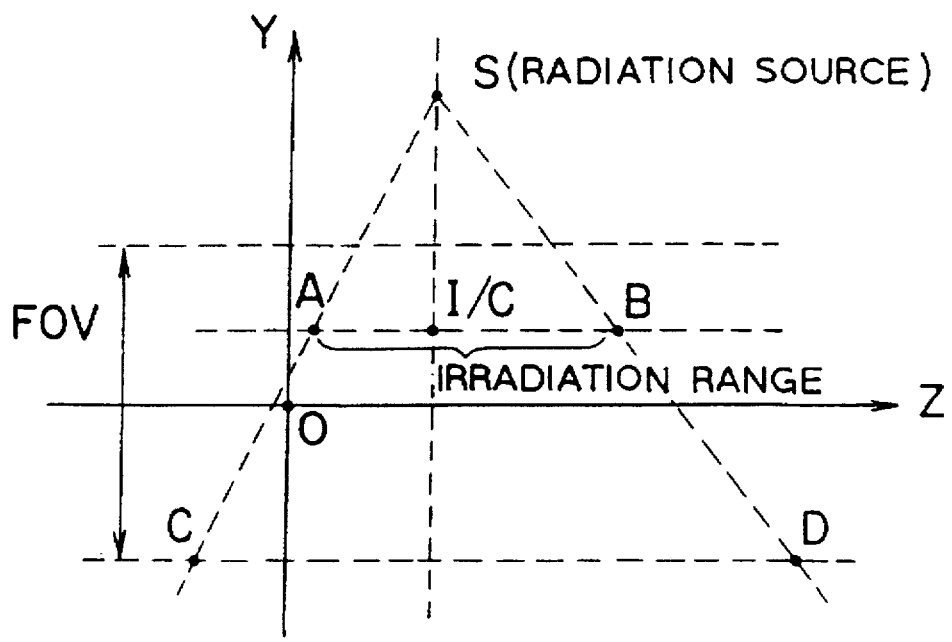
FIG. 78 is an explanatory diagram concerning a range of reconstruction of images acquired by helical scanning in the eighth embodiment.

The eighth embodiment of the present invention will be described in conjunction with FIGS. 78 and 79. The hardware configuration of this embodiment is identical to that of the first embodiment, of which description will therefore be omitted.

In the eighth embodiment, helical scanning and image reconstruction are carried out in consideration of an isocenter I/C. The main control unit 40 in the console 13 performs the calculation graphically shown in FIG. 78.

To be more specific, a scanogram is produced in the same manner as the one described in terms of the seventh embodiment. After an isocenter I/C and a radiation field RF are set, scan planning is commenced (See the procedure of steps 60 to 62 in FIG. 72). Scan planning is carried out so that an image whose reconstruction center is consistent with the isocenter I/C will be produced. In addition, an FoV range Is determined. By determining the FoV range as shown in FIG.

78, both limits of scan are defined. Lines SA and SB linking points A and B, which define a range in a body-axis (z-axis) direction of the radiation field RF, with the radiation source S can be drawn. Intersections of lines SA and SB with the lower limit of the FoV range shall be regarded as points C and D. A region between points C and D is regarded as a reconstruction range.

Based on the reconstruction parameters calculated as mentioned above, helical scanning is performed. Resultant projection data is reconstructed, and therapy planning is carried out.

Figure 79:
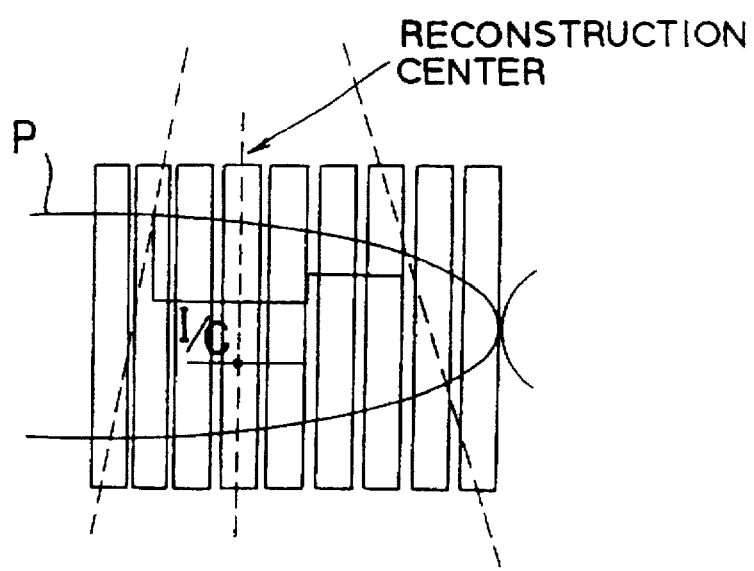
FIG. 79 is an explanatory diagram concerning an example of slices on which helical scanning is performed for image reconstruction.

Consequently, as shown in FIG. 79, part of the projection data corresponding to an irradiation range is reconstructed with the reconstruction center consistent with the isocenter.

As mentioned above, since image reconstruction is performed with an isocenter as a reconstruction center in the course of therapy planning, this embodiment enables more accurate therapy planning similar to the seventh embodiment.

(The Ninth Embodiment)

The ninth embodiment of the present invention will be described with reference to FIGS. 80 to 84. The hardware configuration in this embodiment is identical to the one in the seventh embodiment.

The ninth embodiment is preferable where voxel data produced by helical scanning or the like is available. A volume that is exposed to radiation by a pair of leaves 56 of the multileaf collimator 55 is rendered by performing multiplanar reconstruction (MPR). An opening provided by the pair of leaves that is an interleaf opening is also delineated.

Figure 80:
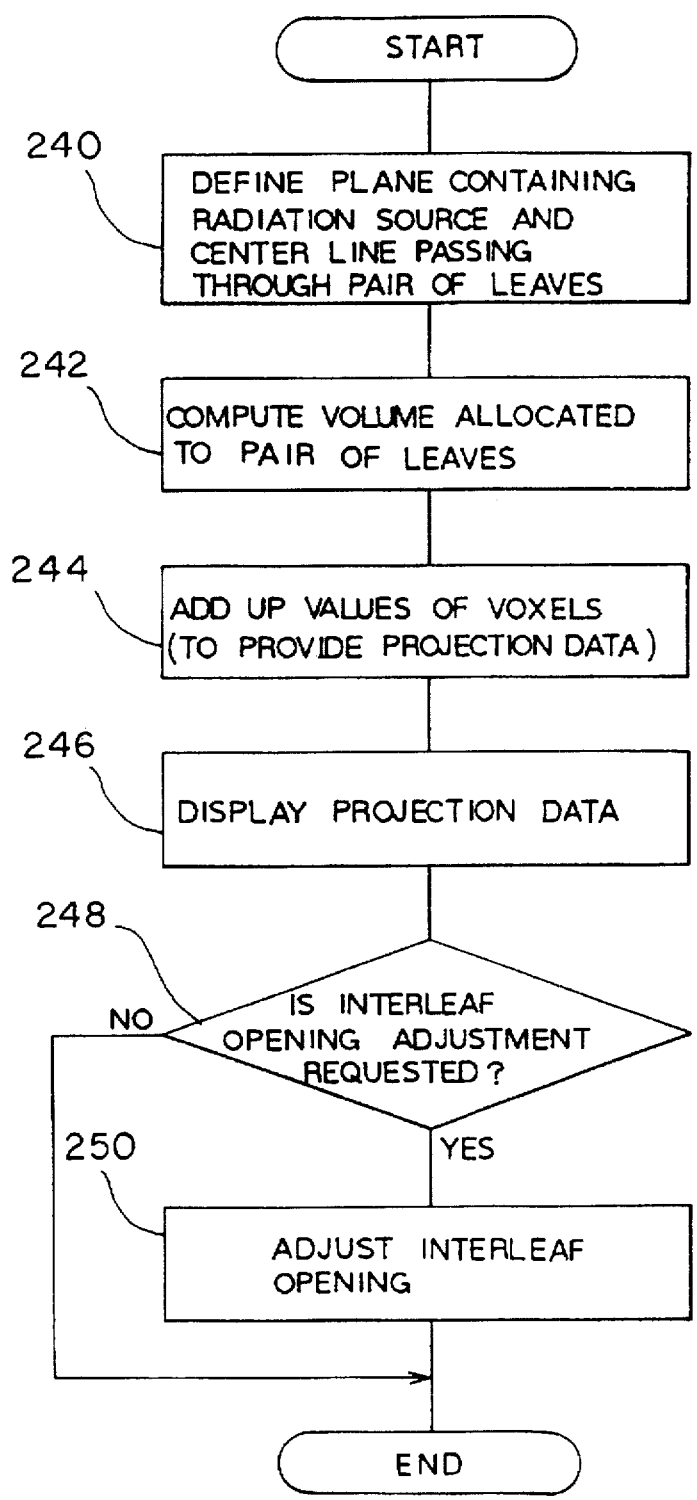
FIG. 80 is a flowchart describing a sequence of displaying an MPR image for each volume allocated to a pair of leaves which is executed by a main control unit in the ninth embodiment.
Figure 81:
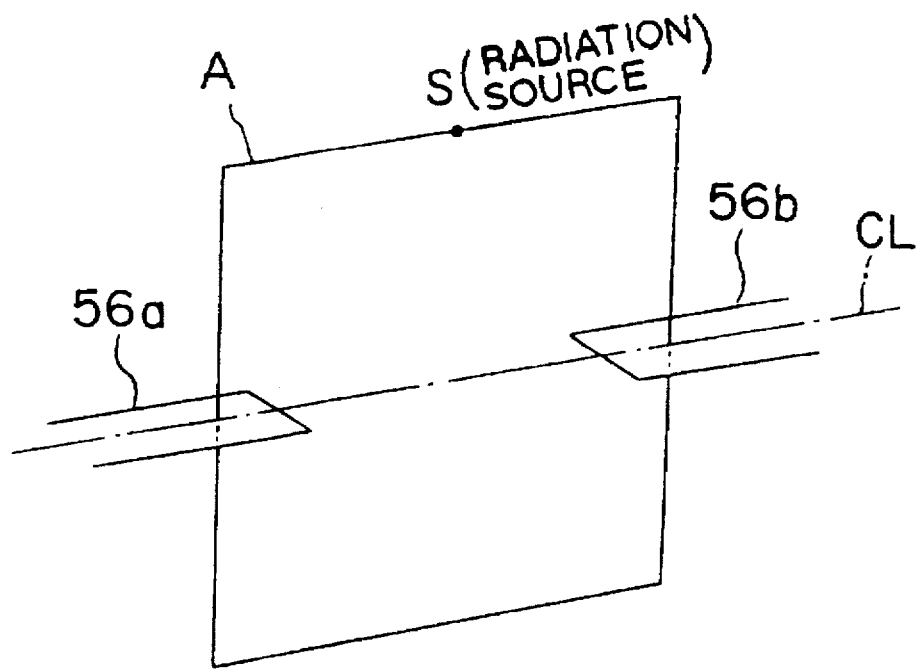
FIG. 81 is an explanatory diagram concerning a step of the sequence of displaying an MPR image.
Figure 82:
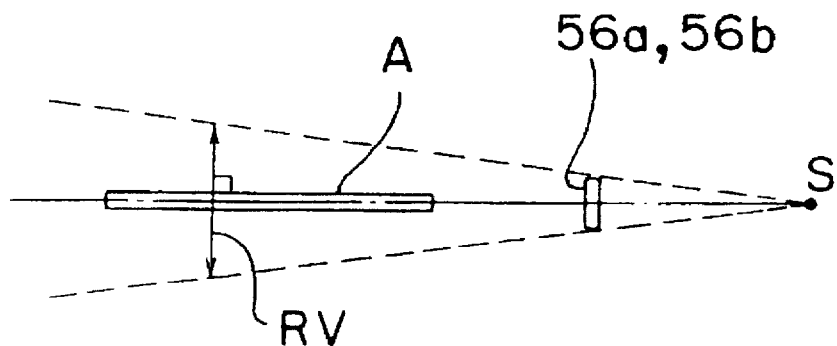
FIG. 82 is an explanatory diagram concerning a step of the sequence of displaying an MPR image.
Figure 83:
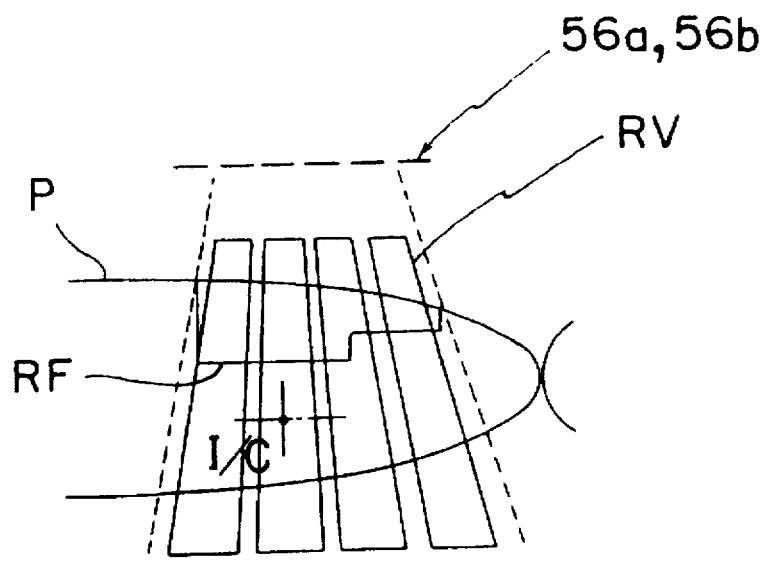
FIG. 83 is an explanatory diagram concerning a volume allocated to a pair of leaves in the ninth embodiment.
Figure 84:
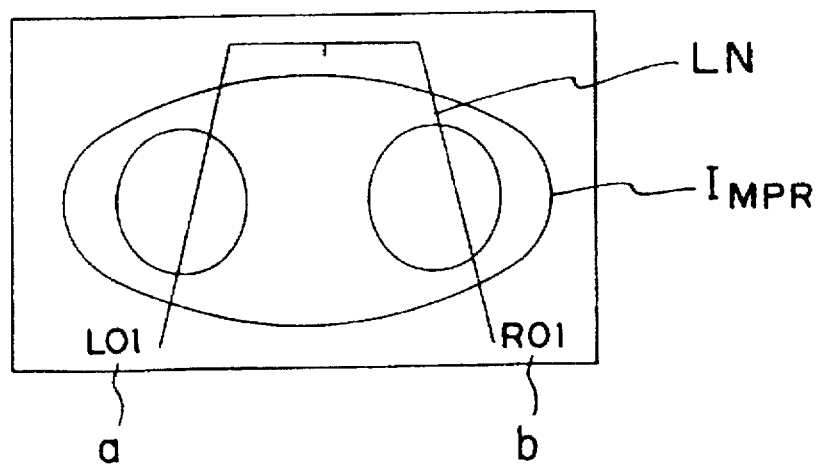
FIG. 84 shows a screen displaying an example of an MPR image.

For rendering a volume allocated to a pair of leaves by MPR, the main control unit 40 executes the sequence shown in FIG. 80. Specifically, at step 240, plane A is defined to contain, as shown in FIG. 81, a center line CL, which passes through a pair of leaves 56a and 56b selected at the input unit 48 (for example, a trackball), and the radiation source S. At step 242, a volume RV that is exposed to radiation by the pair of leaves 56a and 56b is, as shown in FIG. 82, computed on the basis of environment data. FIG. 83 shows an array of volumes allocated to a plurality of pairs of leaves. Control is then passed to step 244. Pixel values residing in voxel data representing the volume RV are added up and used as projection data concerning plane A. At step 242, the projection data concerning plane A (MPR image $I_{MPR}$) is, as shown in FIG. 84, displayed together with beam-fan lines defining an irradiation range (that is an interleaf opening) LN and the responsible leaf numbers a and b.

When the MPR image $I_{MPR}$ is displayed it is determined, based on operational information provided through a pointing device (for example, a mouse or light pen) serving as an input unit whether, the interleaf opening is acceptable. When interleaf opening adjustment is commanded, the interleaf opening (beam-fan lines LN) is adjusted promptly according to the operational information. The foregoing display and adjustment are carried out for each pair of leaves (See FIG. 83).

As a result, an image rendering a volume that is exposed to radiation by a pair of leaves of a multileaf collimator can be checked shortly. In addition, an interleaf opening can be adjusted shortly. This contributes to high-precision fast therapy planning.

As described so far, according to the present invention, for producing images employed in therapy planning, scan planning is performed in consideration of an isocenter and a reconstruction center and then X-ray scanning is carried out. Alternatively, scanning is performed so that a CT image rendering an isocenter will be produced, that the isocenter and reconstruction center will be consistent with each other, and that a gantry will be tilted to have the same angles as radiation paths in order to visualize regions away from the isocenter. This leads to more accurate radiotherapy planning.

For the sake of completeness it should be mentioned that the embodiment examples shown above are not definitive lists of possible embodiments. The expert will appreciate that it is possible to combine the various construction details or to supplement or modify them by measures known from the prior art without departing from the basic inventive principles.

What is claimed is:

1. A radiotherapy system comprising:

a radiotherapy planning CT system for producing data including contour data of a radiation field required for radiotherapy of a lesion of a subject using an image formed by irradiating the subject with X rays;

a radiotherapy apparatus incorporating a radiation source producing radiation and a multileaf-type collimator for limiting a path of the radiation in conformity with the radiation field, said collimator having a plurality of leaves independently movable from each other and forming an opening corresponding to the radiation field;

means for producing data of the opening; and means for controlling limiting positions of the plurality of leaves in accordance with the data of the opening, wherein said opening data producing means includes an element for selecting of a circumscription mode, an inscription mode, and a middle-point mode, said circumscription mode being a state in which limiting ends of the plurality of leaves circumscribe a border of the radiation field, said inscription mode being a state in which the limiting ends inscribe the border, and said middle-point mode being a state in which each middle-point of the limiting ends intersects the border, and an element for calculating the data of the opening in compliance with the selected mode.

2. The radiotherapy system according to claim 1, wherein said opening data producing means is included in the radiotherapy planning CT system.

3. A radiotherapy apparatus in which radiation from a radiation source is limited into a given size of a radiation field by an adjustable opening of a multileaf-type collimator and the limited radiation is directed onto a subject laid on a slewing couch, the apparatus comprising:

means for receiving at least one of a control data of the opening and a control data of a slewing angle of the couch, the control data being produced outside the radiotherapy apparatus; and means for controlling at least one of the multileaf collimator and the couch on the basis of the received control data.

* * * * *

UNITED STATES PATENT AND TRADEMARK OFFICE
CERTIFICATE OF CORRECTION

PATENT NO. : 5,734,692
DATED : March 31, 1998
INVENTOR(S) : Yasuhiro SEKI

It is certified that error appears in the above-identified patent and that said Letters Patent is hereby corrected as shown below:

Title page, Item [57], in the Abstract, line 1, after "comprising:", insert -- a --.

Claim 1, Column 38, line 37, after "selecting", insert -- at least one --.

Signed and Sealed this

Sixteenth Day of March, 1999

Q. TODD DICKINSON

*Attest:*

*Attesting Officer*   *Acting Commissioner of Patents and Trademarks*